US008129086B2

(12) United States Patent
Hatakeyama et al.

(10) Patent No.: US 8,129,086 B2
(45) Date of Patent: Mar. 6, 2012

(54) POLYMERIZABLE COMPOUND, POLYMER, POSITIVE RESIST COMPOSITION, AND PATTERNING PROCESS USING THE SAME

(75) Inventors: Jun Hatakeyama, Jyoetsu (JP); Takeru Watanabe, Jyoetsu (JP); Seiichiro Tachibana, Jyoetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 367 days.

(21) Appl. No.: 12/453,665

(22) Filed: May 18, 2009

(65) Prior Publication Data

US 2009/0297979 A1 Dec. 3, 2009

(30) Foreign Application Priority Data

Jun. 3, 2008 (JP) ................................. 2008-146205

(51) Int. Cl.
*G03F 7/00* (2006.01)
*G03F 7/004* (2006.01)
*G03F 7/40* (2006.01)
*C08F 32/00* (2006.01)
*C08F 20/10* (2006.01)

(52) U.S. Cl. ...................... 430/270.1; 430/330; 430/905; 430/913; 522/108; 526/280; 526/281; 526/308; 526/309; 526/326

(58) Field of Classification Search ............... 430/270.1, 430/905, 913, 330; 522/108; 526/309, 326, 526/280, 281, 308
See application file for complete search history.

(56) References Cited

U.S. PATENT DOCUMENTS

| | | | | |
|---|---|---|---|---|
| 5,391,650 | A | * | 2/1995 | Brennan et al. ............... 525/523 |
| 5,965,325 | A | * | 10/1999 | Matsuo et al. ............ 430/287.1 |
| 6,323,295 | B1 | * | 11/2001 | Muhlebach et al. .......... 526/171 |
| 6,448,420 | B1 | | 9/2002 | Kinsho et al. |
| 6,630,280 | B1 | | 10/2003 | Fujimori et al. |
| 6,753,125 | B2 | * | 6/2004 | Choi et al. ................. 430/270.1 |
| 7,012,123 | B2 | * | 3/2006 | Ishizawa et al. ............. 526/284 |
| 7,491,483 | B2 | * | 2/2009 | Hatakeyama et al. ..... 430/270.1 |
| 7,510,820 | B2 | * | 3/2009 | Hatakeyama et al. ........ 430/323 |
| 7,887,991 | B2 | * | 2/2011 | Hatakeyama et al. ..... 430/270.1 |
| 7,923,195 | B2 | * | 4/2011 | Hatakeyama et al. ..... 430/270.1 |
| 2001/0034000 | A1 | * | 10/2001 | Matsuo et al. ................. 430/326 |
| 2007/0231708 | A1 | | 10/2007 | Matsumaru et al. |
| 2008/0166655 | A1 | | 7/2008 | Ogata et al. |
| 2008/0199806 | A1 | * | 8/2008 | Hatakeyama et al. ..... 430/270.1 |
| 2010/0129738 | A1 | * | 5/2010 | Takemura et al. ................. 430/5 |

FOREIGN PATENT DOCUMENTS

| | | |
|---|---|---|
| CA | 2049772 A1 | 2/1992 |
| JP | A-4-230645 | 8/1992 |
| JP | A-11-322656 | 11/1999 |
| JP | A-2000-327633 | 11/2000 |
| JP | A-2005-84365 | 3/2005 |
| JP | A-2006-45311 | 2/2006 |
| JP | A-2006-96965 | 4/2006 |
| JP | A-2006-169302 | 6/2006 |
| JP | A-2006-178317 | 7/2006 |
| JP | B2-3865048 | 1/2007 |
| JP | B2-3963625 | 6/2007 |
| JP | 2007171895 A * | 7/2007 |
| WO | WO 2004/074242 A2 | 9/2004 |

OTHER PUBLICATIONS

Hillman et al.; "A novel apparatus for the uniform heating of substrates during post expose bake;" *Proceedings of SPIE*; 2003; pp. 1319-1326; vol. 5039.
Matsuzawa et al.; "Theoretical Calculation of Photoabsorption of Various Polymers in an Extreme Ultraviolet Region;" *Japan Journal of Applied Physics*; Dec. 1999; pp. 7109-7113; vol. 38, No. 12B.
Connor et al.; "Benzyl Chloromethyl Ether [Benzene, (chloromethyoxy)methyl-];" *Organic Syntheses. Coll.*; 1988; pp. 101-103; vol. 6.
Kishikawa et al.; "Assessment of trade-off between resist resolution and sensitivity for optimization of hyper-NA immersion lithography;" *Proceedings of SPIE*; 2007; vol. 6520.

* cited by examiner

*Primary Examiner* — Amanda C. Walke
(74) *Attorney, Agent, or Firm* — Oliff & Berridge, PLC

(57) ABSTRACT

A polymer suitable as a base resin for a positive resist composition, in particular a chemically amplified positive resist composition, having a higher resolution, a larger exposure allowance, a smaller sparse-dense size difference, a better process applicability, a better pattern configuration after exposure, and in addition, a further excellent etching resistance, than a conventional positive resist. A positive resist composition using the same, a patterning process, and a novel polymerizable compound to obtain the polymer. A polymer has a hydrogen atom of at least a carboxyl group is substituted by an acid labile group represented by the following general formula (2), a positive resist composition using the same, a patterning process, and a novel polymerizable compound to obtain a polymer like this.

20 Claims, No Drawings

POLYMERIZABLE COMPOUND, POLYMER, POSITIVE RESIST COMPOSITION, AND PATTERNING PROCESS USING THE SAME

BACKGROUND OF THE INVENTION

1. Field of the Invention

The present invention relates to a polymer suitable as a base resin for a positive resist composition, especially for a chemically amplified resist composition, a positive resist composition using the same, a patterning process, and a polymerizable compound to obtain the polymer thereof.

2. Description of the Related Art

As LSI progresses toward a high integration and a further acceleration in speed, a finer pattern rule is rapidly progressing. In particular, the expansion of a flash memory market and the enlargement of a memory capacity lead the finer pattern rule. Mass production of a 65-nanometers node device by a miniaturized fine line of an ArF lithography is currently in practice and preparation of the mass production of a 45-nanometers node device by a next generation ArF-immersion lithography is now progressing. As the candidates for the post next generation technology, a 32-nanometers node, an immersion lithography by a ultra high NA lens comprising a liquid having a higher refractive index than water, a high-refractive lens and a high-refractive resist, an extreme ultraviolet (EUV) lithography of 13.5-nanometers wavelength, and a double exposure (a double patterning lithography) of an ArF lithography, and the like are being studied.

In a high energy beam of an extremely short wavelength such as an EB (an electronic beam) and an X-ray, a light element such as a hydrocarbon used in a resist has almost no absorption, and thus a resist composition based on polyhydorxystyrene has been studied.

An EB resist has been practically used for a mask drawing. In recent years, a mask production technology has been considered to be a problem. A reduced projection exposure system with a one-fifth reduction ratio had been used from the time of a g-beam exposure, but an effect of the size misalignment of a mask on a size change of a pattern on a wafer becomes a problem because an enlarged chip size, a projection lens with an enlarged diameter, and also a one-fourth reduction ratio have been employed. In addition, as the pattern miniaturization progresses, it is pointed out that a size misalignment on a wafer is becoming larger than a size misalignment of a mask. A Mask Error Enhancement Factor (MEEF) is calculated by using a mask size change as a denominator and a size change on a wafer as a numerator. In the pattern of a 45-nanometers class, it is not a rare case that MEEF is 4 or more. If the reduction ratio is one-fourth and MEEF is 4, it can be said that the precision equivalent to that of a substantially same magnitude mask is necessary in the mask production.

To improve a precision of a line width in a mask production, exposure instruments using a laser beam to an electronic beam (EB) have been used. In addition, because a further miniaturization becomes possible by raising an acceleration voltage of an electron gun, a voltage of 10 to 30 keV, and of 50 keV becomes a mainstream recently, and the study is progressing toward 100 keV further.

Here, as an increase in the acceleration voltage, a tendency to a lower sensitivity of a resist becomes a problem. A higher acceleration voltage enables to improve a degree of resolution and a size controlling because the effect of a front scattering in a resist film becomes smaller, leading to an improvement in a contrast of an electronic drawing energy, but a sensitivity of a resist is decreased because an electron passes through a resist film freely. Because a mask exposure instrument exposes a light directly for drawing with one stroke, a decrease in the resist sensitivity leads to a decrease in productivity and thus is not desirable. In view of a request for a higher sensitivity, a chemically amplified resist is being studied.

As a miniaturization of a pattern of an EB lithography for a mask production progresses, a move to a thinner resist is progressing in order to prevent a pattern fall due to a high aspect ratio at the time of development from occurring. In the case of a optical lithography, the move to a thinner resist contributes greatly to an improvement in the resolution. This is owing to a progress in flattening of a device by introduction of a CMP and the like. In the mask production, a substrate is flat, thus a film thickness of the substrate to be processed (for instance, Cr, MoSi and $SiO_2$) is determined by the light shielding rate and the phase difference control. In order to make it thinner, an improvement in a dry-etching resistance of a resist is necessary.

Meanwhile, it is generally assumed that there is a relationship between a resist carbon density and a dry-etching resistance. In the EB drawing not affected by an absorption, a resist based on a novolak polymer having a good etching resistance has been developed.

In addition, it is reported that an absorption of a carbon atom is small in a soft X-ray (EUV) exposure using a 5-20 nanometers wavelength which is expected, along with an $F_2$ exposure, as a promising exposure method in a fine processing using a 70 nanometers wavelength or in a process that follows thereafter. A higher carbon density is effective not only for improvement in the dry-etching resistance but also for increase in a transmittance in the region of a soft X-ray wavelength (N. Matsuzawa et al., Jpn. J. Appl. Phys. Vol. 38, p 7109-7113 (1999)).

As a miniaturization of the patterning processing progresses, an indistinct image due to diffusion of an acid became a problem (SPIE Vol. 5039, p 1 (2003)). To secure the degree of resolution in a fine pattern in the post 45 nanometers size, it is proposed that not only an improvement in the dissolution contrast, which has been proposed in the past, but also a suppression of diffusion of an acid are important (SPIE Vol. 6520, 65203L-1 (2007)). However, in a chemically amplified resist, there has been a problem in that a sensitivity and a contrast are markedly decreased if diffusion of an acid is suppressed to the maximum extent by lowering the temperature of a post exposure bake (PEB) and shortening the time of a PEB, because a sensitivity and a contrast are increased by diffusion of an acid.

SUMMARY OF THE INVENTION

The present invention was made in view of the above situation, and has an object to provide a polymer suitable as a base resin for a positive resist composition, particularly a chemically amplified positive resist composition, having a higher sensitivity and resolution, a better pattern configuration after exposure, and in addition, an further excellent etching resistance than a conventional positive resist composition, a positive resist composition using the same, a patterning process, and a novel polymerizable compound to obtain the polymer as mentioned above.

The present invention provides a polymerizable compound represented by the following general formula (1) to address the problem as mentioned above:

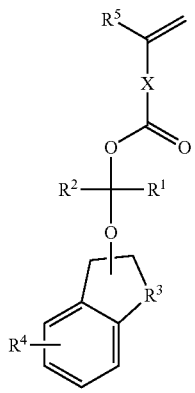

(1)

wherein, each of $R^1$ and $R^2$ independently represents any of a hydrogen atom, or a linear, a branched, or a cyclic alkyl group having 1 to 6 carbon atoms; $R^3$ represents a methylene group or an ethylene group; $R^4$ represents any of a hydrogen atom, an alkyl group having 1 to 30 carbon atoms, an alkyl group a part of or all of whose hydrogen atoms are substituted by a halogen atom, an alkoxy group, an alkanoyl group, an alkoxycarbonyl group, an aryl group having 6 to 10 carbon atoms, a halogen atom, or a cyano group; $R^5$ represents a hydrogen atom or a methyl group; X represents any of a single bond, —C(=O)—O—$R^6$—, a phenylene group, or a naphthylene group; and $R^6$ represents any of a linear, a branched, or a cyclic alkylene group having 1 to 10 carbon atoms, and optionally containing an ester group, an ether group, or a lactone ring.

The present invention further provides a polymer whose hydrogen atom of at least a carboxyl group is substituted by an acid labile group represented by the following general formula (2):

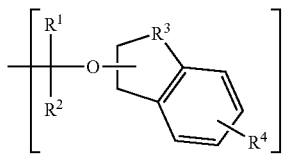

(2)

wherein, each of $R^1$ and $R^2$ independently represents any of a hydrogen atom, a linear, a branched, or a cyclic alkyl group having 1 to 6 carbon atoms; $R^3$ represents a methylene group or an ethylene group; and $R^4$ represents any of a hydrogen atom, an alkyl group having 1 to 30 carbon atoms, an alkyl group a part of or all of whose hydrogen atoms are substituted by a halogen atom, an alkoxy group, an alkanoyl group, an alkoxycarbonyl group, an aryl group having 6 to 10 carbon atoms, a halogen atom, or a cyano group.

In this case, it is preferable that the polymer contain at least a repeating unit "a" represented by the following general formula (3):

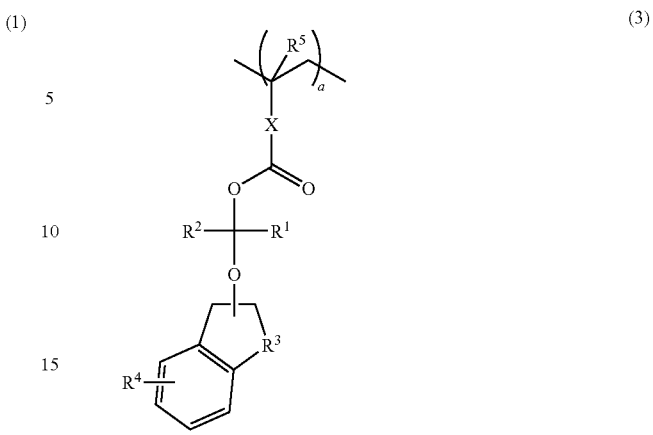

wherein, $R^1$ to $R^4$ represent the same meanings as before; $R^5$ represents a hydrogen atom or a methyl group; X represents any of a single bond, —C(=O)—O—$R^6$—, a phenylene group, or a naphthylene group; and $R^6$ represents any of a linear, a branched, or a cyclic alkylene group having 1 to 10 carbon atoms, and may contain an ester group, an ether group, or a lactone ring.

In this case, it is preferable that the polymer contain a repeating unit "a" represented by the general formula (3) accounting for 5 to 70 mole % of all the repeating units, and its weight-average molecular weight is 1,000 to 500,000.

Further, the repeating unit "a" represented by the general formula (3) is preferably a repeating unit a1 or a repeating unit a2 shown in the following general formula (4):

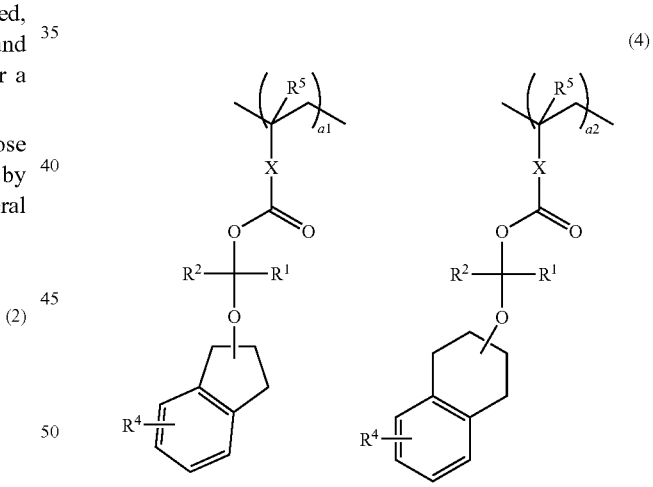

wherein, $R^1$, $R^2$, $R^4$, $R^5$, and X represent the same meanings as before, and $0.05 \leq a1+a2 \leq 0.75$.

Further, the polymer is preferably a copolymer of, in addition to the repeating unit "a" represented by the general formula (3), a repeating unit "b" which is an adhesion group having any of a hydroxy group, a lactone ring, an ether group, an ester group, a carbonyl group, or a cyano group, with the weight-average molecular weight of 1,000 to 500,000, and $0<a<1.0$, $0<b<1.0$, and $0.05 \leq a+b \leq 0.7$.

The present invention provides a positive resist composition containing as a base resin any of the polymers as mentioned above.

The positive resist composition of the present invention has an extremely high contrast of an alkaline-dissolution rate before and after an exposure of a high-energy beam, and thus has a high sensitivity and resolution. In addition, it has a small line edge roughness because swelling in a development is suppressed, a small residue after an etching, and a high etching resistance. Because of these properties, it has an extremely high practicality and is suitable for a micropatterning material in the VLSI manufacture or a photo mask patterning material.

The positive resist composition of the present invention is preferably a chemically amplified resist composition containing further an organic solvent and an acid generator.

When the polymer of the present invention is used as a base resin, and in addition, contains further an organic solvent and an acid generator, a dissolution rate of the polymer into a developer is accelerated by an acid-catalyzed reaction in an exposed area. Therefore, a chemically amplified positive resist composition having an extremely high sensitivity, usable as a micropatterning material for the VLSI manufacture and the like, which are required in recent years, may be obtained.

In this case, the positive resist composition of the present invention may further contain a dissolution inhibitor.

As remarked above, by adding a dissolution inhibitor into the positive resist composition, it is possible to further increase the difference of the dissolution rates between an exposed area and a non-exposed area, leading to further improvement in the degree of resolution.

The positive resist composition of the present invention may contain further a basic compound and/or a surfactant as an additive.

As remarked above, by adding a basic compound, it is possible, for instance, to suppress a diffusion rate of an acid in a resist film, leading to further improvement in the degree of resolution. By adding a surfactant, it is possible to further improve or control coating properties of the resist composition.

The positive resist composition of the present invention may be used as a patterning process on a semi-conductor substrate, on a mask substrate, and the like by performing at least a step of applying the positive resist composition on a substrate; a step of conducting heat-treatment; a step of exposing a high-energy beam; and a step of developing by using a developer.

It is obvious that the development may be done after the exposure followed by the heat-treatment, and that other processes such as an etching process, a resist-removing process, and a washing process may also be done.

The positive resist composition of the present invention has a high resolution, a large exposure allowance, a small sparse-dense size difference, a good process applicability, and a good pattern configuration after exposure. In addition, it suppresses an acid diffusion rate and shows an excellent etching resistance in particular. Accordingly, a positive resist composition particularly suitable for a micropatterning material of the VLSI manufacture or a photo mask and as a patterning material for an EUV exposure, in particular, a chemically amplified positive resist composition may be obtained.

In addition, according to the present invention, a novel polymerizable compound to obtain the polymer of the present invention may be provided.

DETAILED DESCRIPTION OF THE INVENTION

Inventors of the present invention carried out an extensive investigation with a purpose to obtain a positive resist composition having a high sensitivity and resolution, a large exposure allowance, a small sparse-dense size difference, a good process applicability, a good etching configuration, and an excellent etching resistance, all of which are desired in recent years. As a result, the present inventors found that a polymer containing a carboxyl group which is substituted by an acid labile group having a structure formed of a 1,2,3-indanyl group or a 1,2-tetrahydronaphthyl group, in particular a polymer obtained by substituting a (meth)acrylate by the above-mentioned acetal group, is useful as a base resin for a positive resist composition, in particular a chemically amplified positive resist composition. Based on that information the present invention was accomplished.

The present inventors considered firstly to increase the carbon density of the resist in order to improve the etching resistance. The carbon density of the benzene ring is 92% while that of the naphthalene ring is 94%, thus it is expected that the resist composition containing the naphthalene ring may improve its dry etching resistance. In its nature, the naphthalene ring has a high absorption of a light so that the material containing it has not received so much attention in the past, but was assumed to be a promising composition in the exposure of an extremely short wavelength where there is no effect by the absorption.

In addition, it is expected that an indene copolymer disclosed in the Japanese Patent Publication No. 3865048 and an acenaphthylene copolymer disclosed in the Japanese Patent Laid-Open (kokai) No. 2006-169302 may improve the etching resistance owing to not only a high carbon density but also a rigid main chain structure due to a cycloolefin structure.

Further, it is shown that the etching resistance is also improved by an acetal group having a cyclic structure such as a balky acetal group disclosed in the Japanese Patent Publication No. 3963625 and the Japanese Patent Laid-Open (kokai) No. 2006-96965.

Accordingly, the present inventors found that a positive resist composition, in particular a chemically amplified positive resist composition, suitable particularly for a micropatterning material of the VLSI manufacture or a photo mask, having a remarkably high contrast of alkali-dissolution rates before and after the exposure, a high sensitivity and resolution, a good pattern configuration after exposure, and in addition, an excellent etching resistance, could be obtained by using a polymer obtained by copolymerizing a (meth)acrylate, which is substituted by an acid labile group in order to improve the dissolution contrast and to increase the etching resistance by lowering the acid diffusion, as a base resin for a positive resist composition, in particular, for a chemically amplified positive resist composition.

The positive resist composition of the present invention shows particularly a high dissolution contrast of a resist film, a high sensitivity and resolution, a large exposure allowance, an excellent process applicability, a good pattern configuration after the exposure, particularly a small size difference between a dense pattern and a sparse pattern, and a further excellent etching resistance.

Accordingly, the composition has an extremely high practicality because of these excellent characteristics and is very useful as a resist composition for the VLSI manufacture and as a mask patterning.

In the following, the present invention will be further explained specifically.

The positive resist composition in the present invention is characterized in that a resist composition contains, as a base resin, a polymer whose hydrogen atom of at least a carboxyl group is substituted by an acid labile group represented by the following general formula (2):

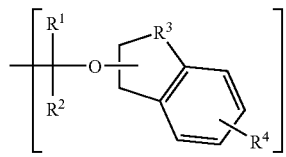

(2)

wherein, each of $R^1$ and $R^2$ independently represents any of a hydrogen atom, a linear, a branched, or a cyclic alkyl group having 1 to 6 carbon atoms; $R^3$ represents a methylene group or an ethylene group; and $R^4$ represents any of a hydrogen atom, an alkyl group having 1 to 30 carbon atoms, an alkyl group a part of or all of whose hydrogen atoms are substituted by a halogen atom, an alkoxy group, an alkanoyl group, an alkoxycarbonyl group, an aryl group having 6 to 10 carbon atoms, a halogen atom, or a cyano group.

Here, it is preferable that the polymer contain at least a repeating unit "a" represented by the following general formula (3)

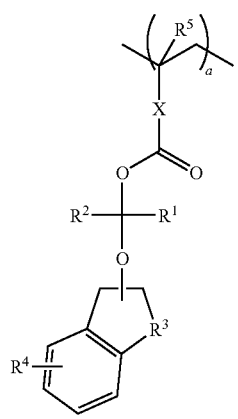

(3)

wherein, $R^1$ to $R^4$ represent the same meanings as before; $R^5$ represents a hydrogen atom or a methyl group; X represents any of a single bond, —C(=O)—O—$R^6$—, a phenylene group, or a naphthylene group; and $R^6$ represents any of a linear, a branched, or a cyclic alkylene group having 1 to 10 carbon atoms, and optionally containing an ester group, an ether group, or a lactone ring.

In this case, it is preferable that the polymer contain a repeating unit "a" represented by the general formula (3) accounting for 5 to 70 mole % of all the repeating units and have the weight-average molecular weight of 1,000 to 500,000.

Further, the repeating unit "a" represented by the general formula (3) may be a repeating unit a1 or a2 as shown in the following general formula (4):

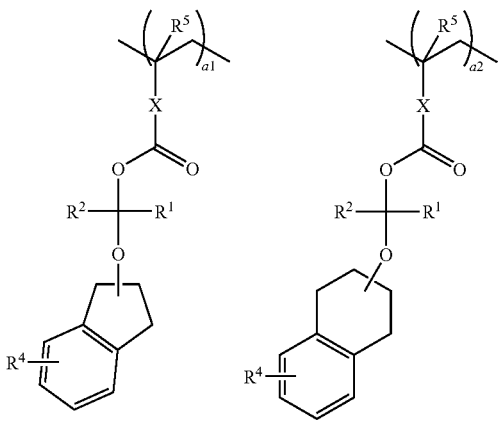

(4)

wherein, $R^1$, $R^2$, $R^4$, $R^5$, and X represent the same meanings as before, and $0.05 \leq a1+a2 \leq 0.75$.

The polymerizable compound (monomer) to obtain the repeating unit represented by the general formula (3) is shown by the following general formula (1):

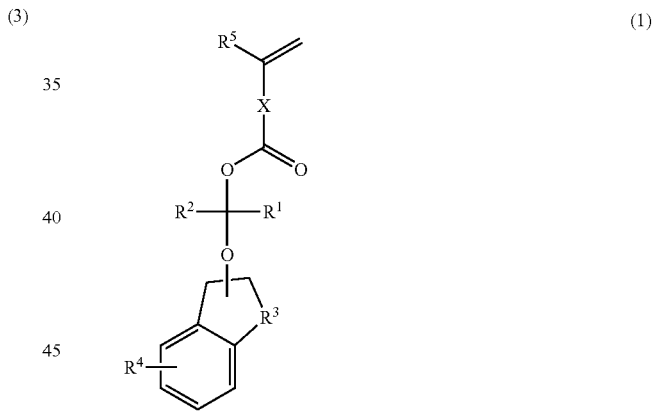

(1)

wherein, each of $R^1$ and $R^2$ independently represents any of a hydrogen atom, or a linear, a branched, or a cyclic alkyl group having 1 to 6 carbon atoms; $R^3$ represents a methylene group or an ethylene group; $R^4$ represents any of a hydrogen atom, an alkyl group having 1 to 30 carbon atoms, an alkyl group a part of or all of whose hydrogen atoms are substituted by a halogen atom, an alkoxy group, an alkanoyl group, an alkoxycarbonyl group, an aryl group having 6 to 10 carbon atoms, a halogen atom, or a cyano group; $R^5$ represents a hydrogen atom or a methyl group; X represents any of a single bond, —C(=O)—O—$R^6$—, a phenylene group, or a naphthylene group; and $R^6$ represents any of a linear, a branched, or a cyclic alkylene group having 1 to 10 carbon atoms, and may contain an ester group, an ether group, or a lactone ring.

Specific examples of this polymerizable compound may be shown as following.

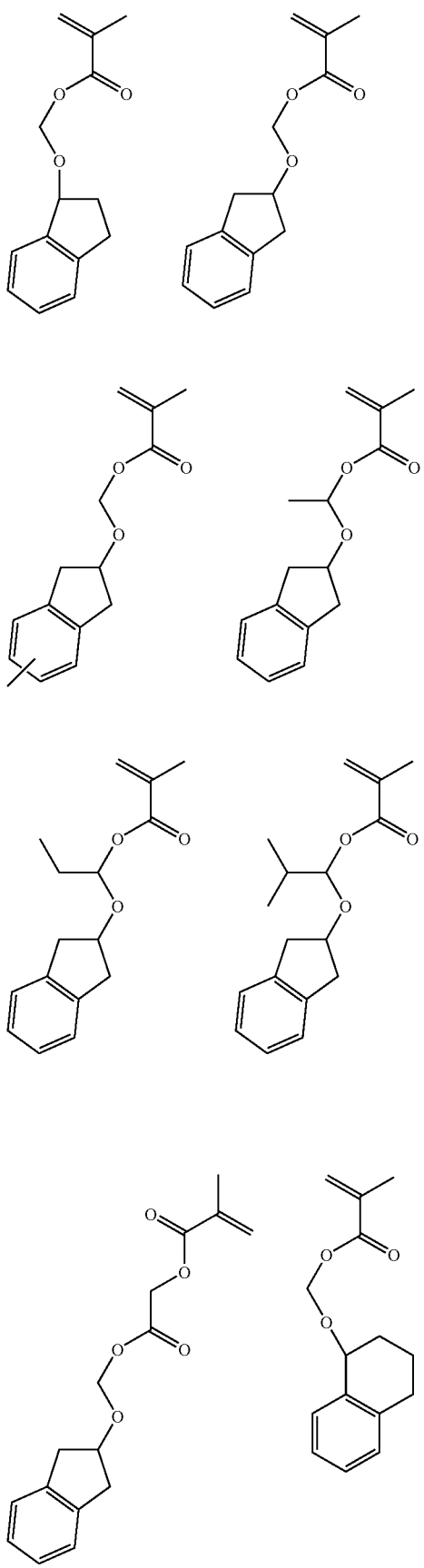

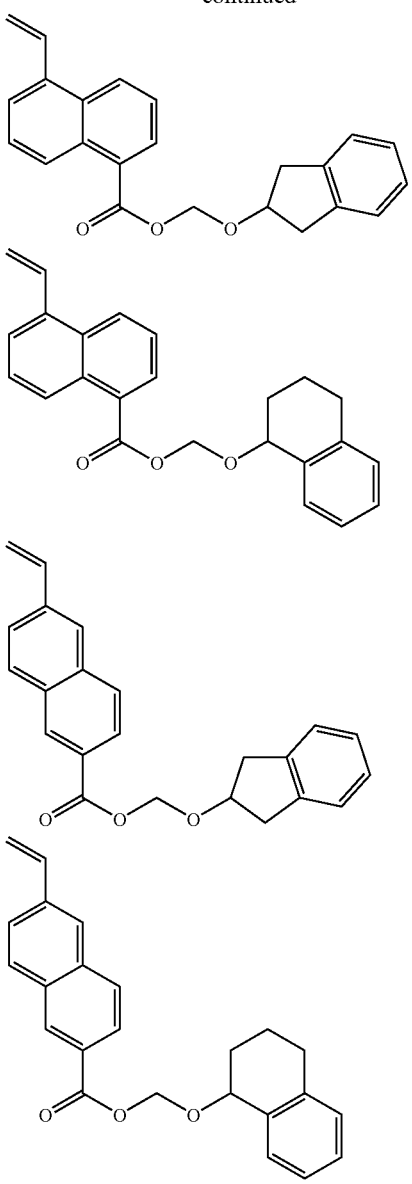

In production of a polymerizable acid labile ester compound of the present invention represented by the general formula (1), an appropriate method for producing the compounds thereof is preferably selected depending on individual structures. Specifically, it may be produced by the following synthetic methods for example, but not restricted to these methods in this invention. In the following, the detailed explanation will be made.

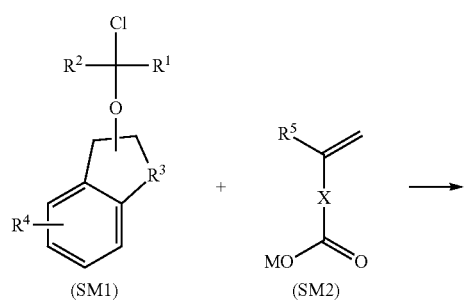

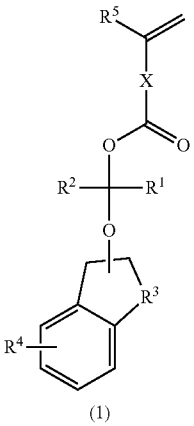

Wherein, $R^1$ to $R^5$ and X represent the same meanings as before; and M represents a cation such as a metal ion and an ammonium ion.

A reaction is shown by the above reaction formula. The formula is an esterification reaction using a 1-chloroalkyl ether compound (SM1) and a carboxylate compound (SM2). It may be performed by a conventional method of an esterification reaction using a carboxylate and a 1-chloroalkyl ether compound. As the carboxylate compound (SM2), commercially available carboxylate compounds, such as various carboxylate metal salts, may be used as they are, or after the carboxylate compound is prepared by using a polymerizable carboxylic acid and a basic compound in a reaction system. An amount of the carboxylate compound (SM2) is preferably 0.5 to 10 mole, in particular, 1.0 to 3.0 mole, relative to 1 mole of the 1-chloroalkyl ether compound (SM1). When the use amount is less than 0.5 mole, a large amount of a raw material remains, thereby sometimes decreasing in a yield greatly. When the use amount is more than 10 mole, the cost of raw materials is increased and a yield based on a reactor is reduced, and thus it is sometimes disadvantageous in terms of a cost. Examples of the basic compound usable to prepare the carboxylate compound from the polymerizable carboxylic acid and the basic compound in a reaction system include amines such as ammonia, triethylamine, pyridine, lutidine, collidine, and N,N-dimethylaniline; hydroxy compounds such as sodium hydroxide, potassium hydroxide, and tetramethylammonium hydroxide; carbonate such as potassium carbonate and sodium hydrogencarbonate; metals such as sodium; metal hydrides such as sodium hydride; metal alkoxides such as sodium methoxide and potassium t-butoxide; organometallic compounds such as butyl lithium and bromo ethyl magnesium; and metal amides such as lithium diisopropylamide. They may be used singly, or in a combination of two or more kinds. An amount of the base is preferably 0.2 to 10 mole, and in particular 0.5 to 2.0 mole, relative to 1 mole of the polymerizable carboxylic acid. When the use amount is less than 0.2 mole, a large amount of the carboxylic acid is wasted, and thus it is sometimes disadvantageous in term of a cost. When the use amount is more than 10 mole, side reactions are increased, thereby sometimes decreasing the yield greatly.

Examples of solvents used in the above reaction include hydrocarbons such as toluene, xylene, hexane, and heptane; chlorinated solvents such as methylene chloride, chloroform, and dichloroethane; ethers such as diethyl ether, tetrahydrofurane, and dibutyl ether; ketones such as acetone and 2-buthanone; esters such as ethyl acetate and butyl acetate; nitriles such as acetonitrile; alcohols such as methanol and ethanol; non-protonic polar solvents such as N,N-dimethylformamide, N,N-dimethylacetamide, and dimethyl sulfoxide; and water. They may be used singly, or in a combination of two or more kinds. In the reaction, a correlative-transfer catalyst such as tetrabutylammonium hydrogen sulfide may be added as a catalyst. In that case, an amount of the phase-transfer catalyst is preferably 0.0001 to 1.0 mole, in particular, 0.001 to 0.5 mole, relative to 1 mole of the 1-chloroalkyl ether compound (SM1). When the use amount is less than 0.0001 mole, sometimes the effect of the addition is not realized. When the amount is more than 1.0 mole, a raw material cost is increased, and thus it is sometimes disadvantageous in terms of a cost.

A temperature of the esterification reaction is preferably −70° C. to a boiling point of a solvent used. Although it can be selected appropriately depending on reaction conditions, in general, temperature between 0° C. to a boiling point of a solvent used is particularly preferable. When the reaction temperature is too high, sometimes side reactions are prominent. Thus, to obtain a high yield, it is important to carry out the reaction at a temperature as low as possible in the range where the reaction may proceed at a practical rate. A time of the reaction is determined preferably by monitoring a progress of the reaction by a thin-layer chromatography, a gas chromatography, and the like in order to obtain a higher yield, but is usually about 30 minutes to about 40 hours. The reaction is carried out by mixing raw materials, the 1-chloroalkyl ether compound (SM1) and the carboxylate compound (SM2), in a solvent. After the reaction, a target polymerizable acid labile ester compound represented by the general formula (1) is obtained by a usual aqueous work-up or by filtering out a salt formed by the reaction and removal of the solvent. The target compound may be purified by a conventional method such as chromatography, distillation, and recrystallization, depending on individual physical properties of an objective compound shown in the general formula (1).

The 1-chloroalkyl ether compound (SM1), a raw material for the esterification reaction, may be obtained by a conventional method for a 1-chloroalkyl-etherification of an aralkyl alcohol. Specifically it can be synthesized by the method according to, for example, Organic Synthesis Collective Volume 6, p. 101 to p. 103 (1988).

Specific examples of the monomer to obtain the repeating unit "b" which is the adhesion group having a hydroxy group, a lactone ring, an ether group, an ester group, a carbonyl group, and a cyano group, include compounds as shown below.

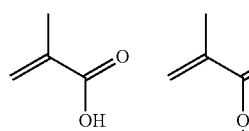

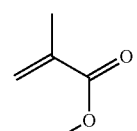

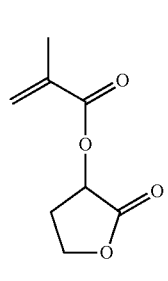

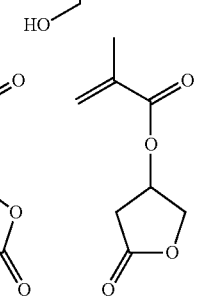

-continued

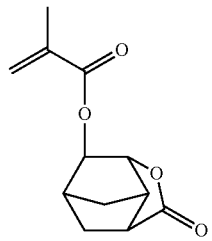 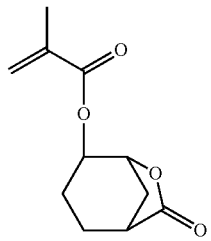

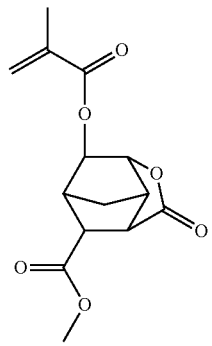 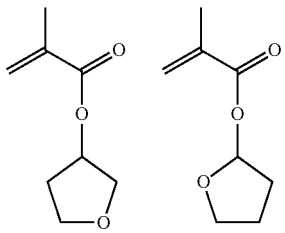

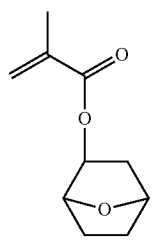 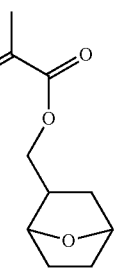

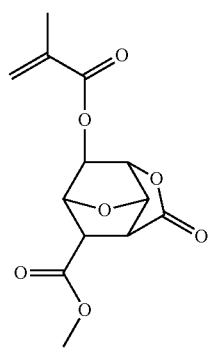 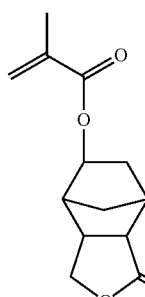

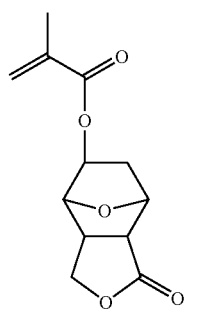 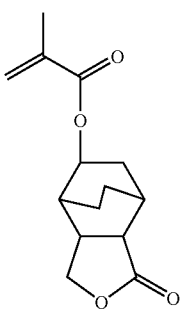

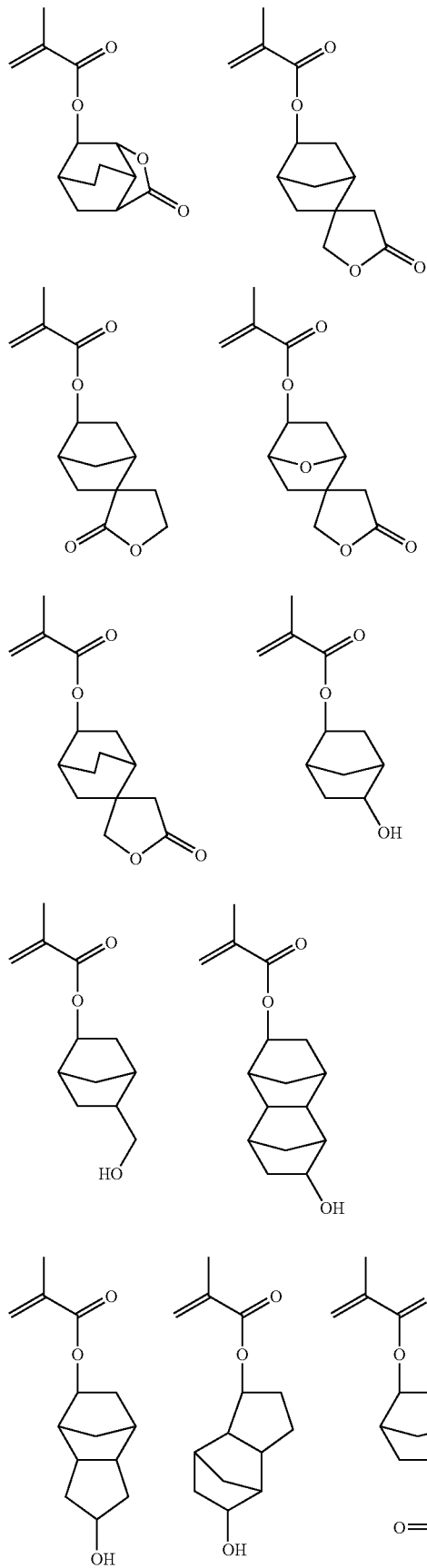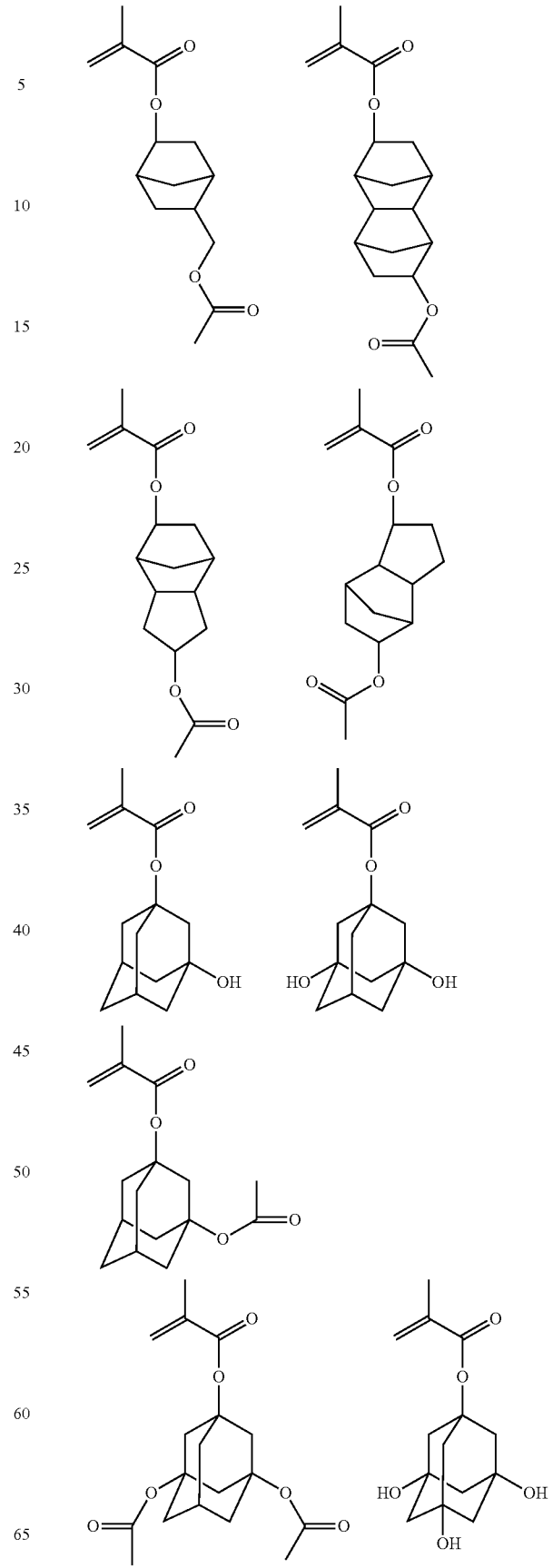

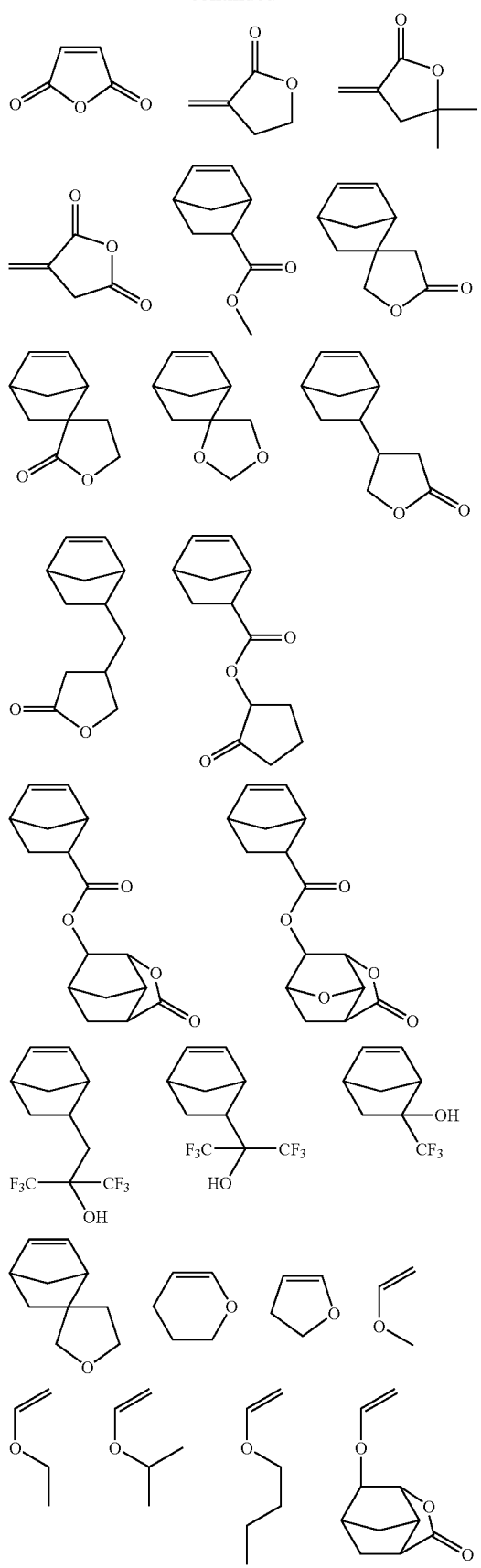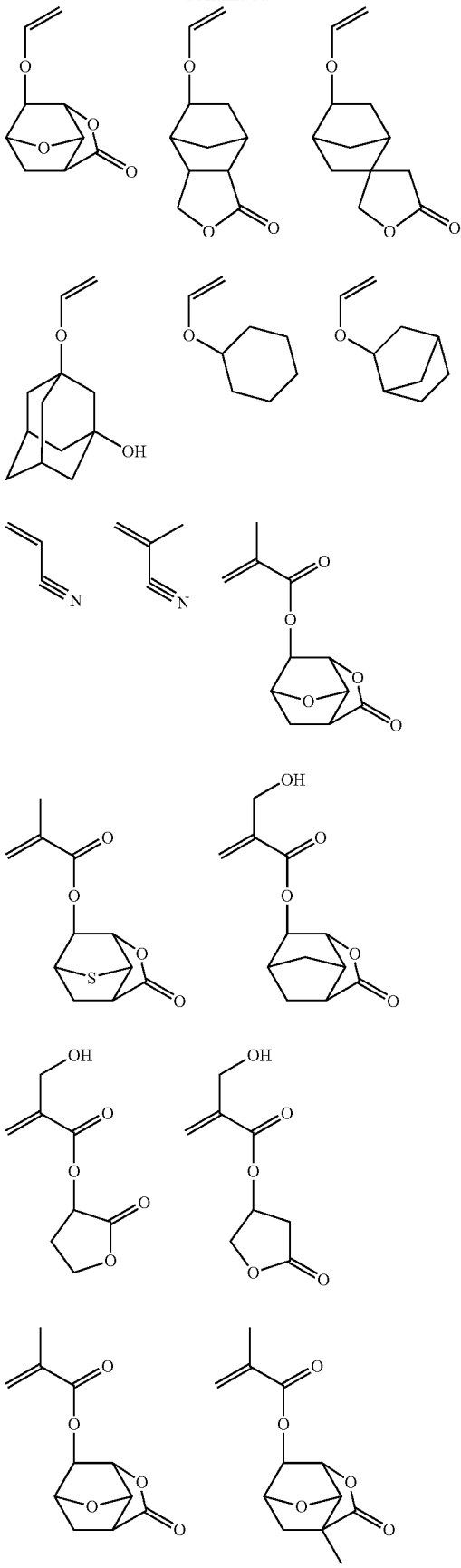

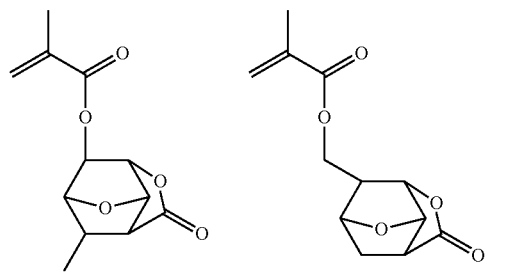
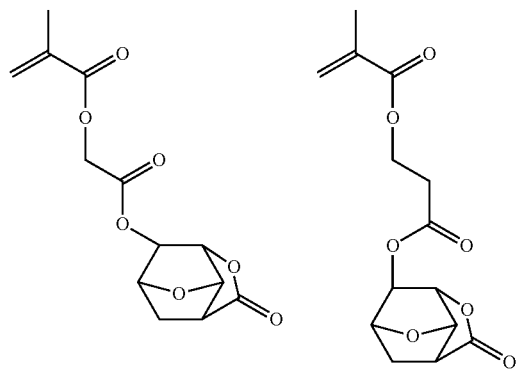
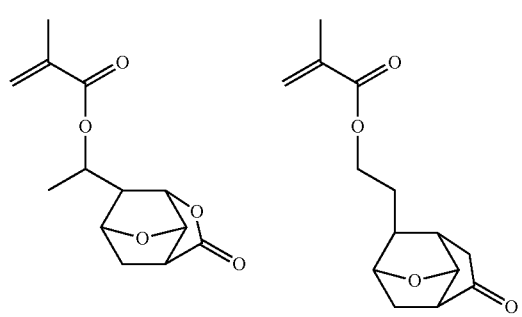
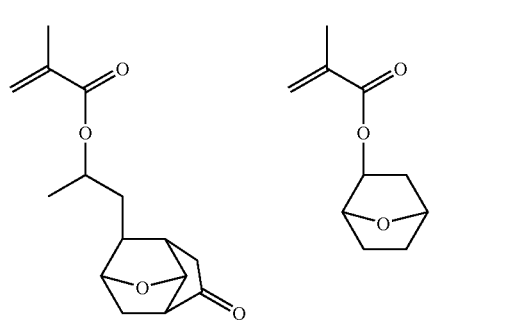
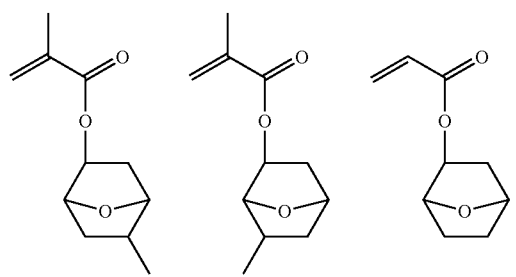
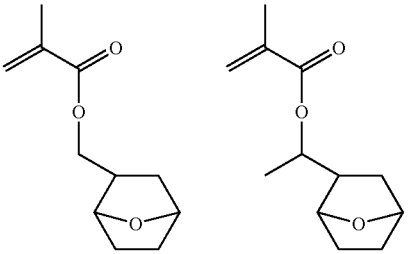
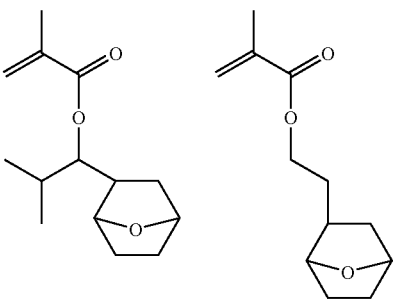
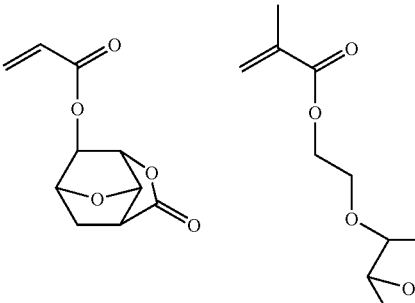
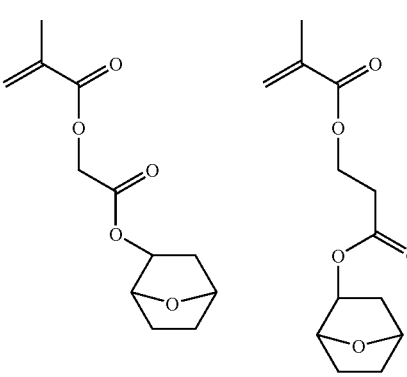
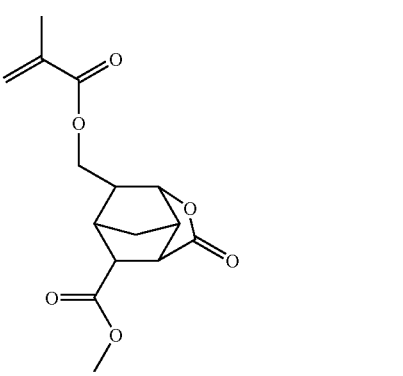

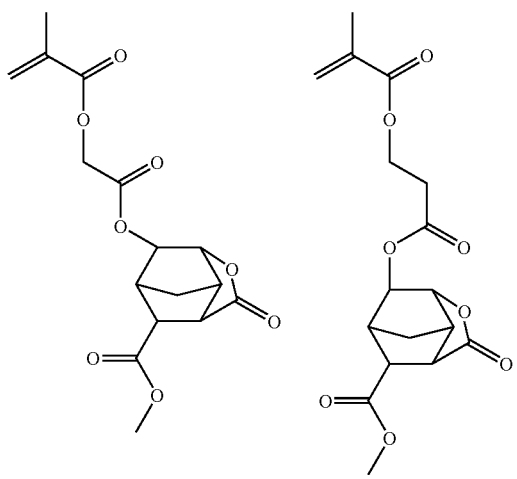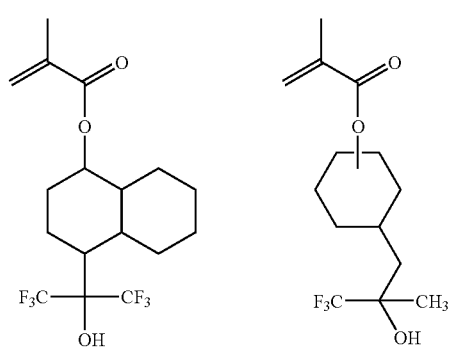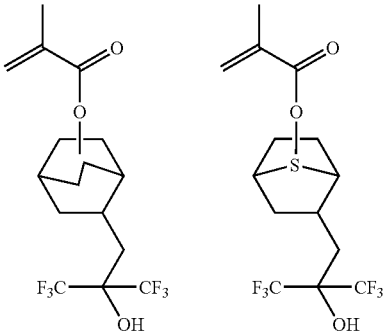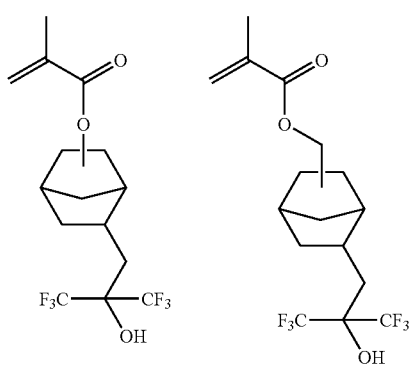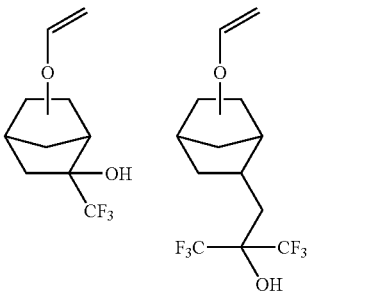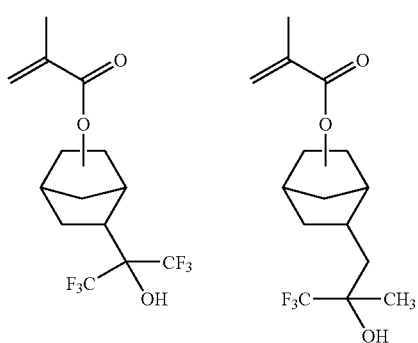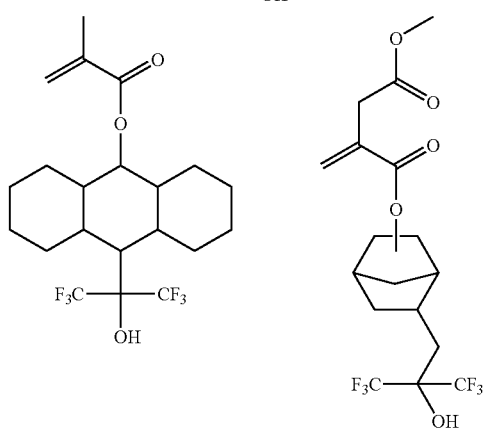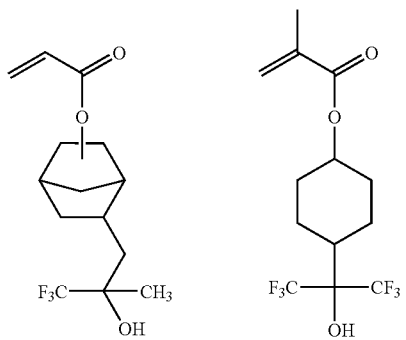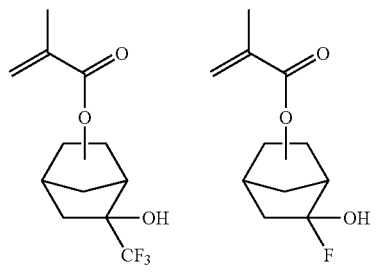

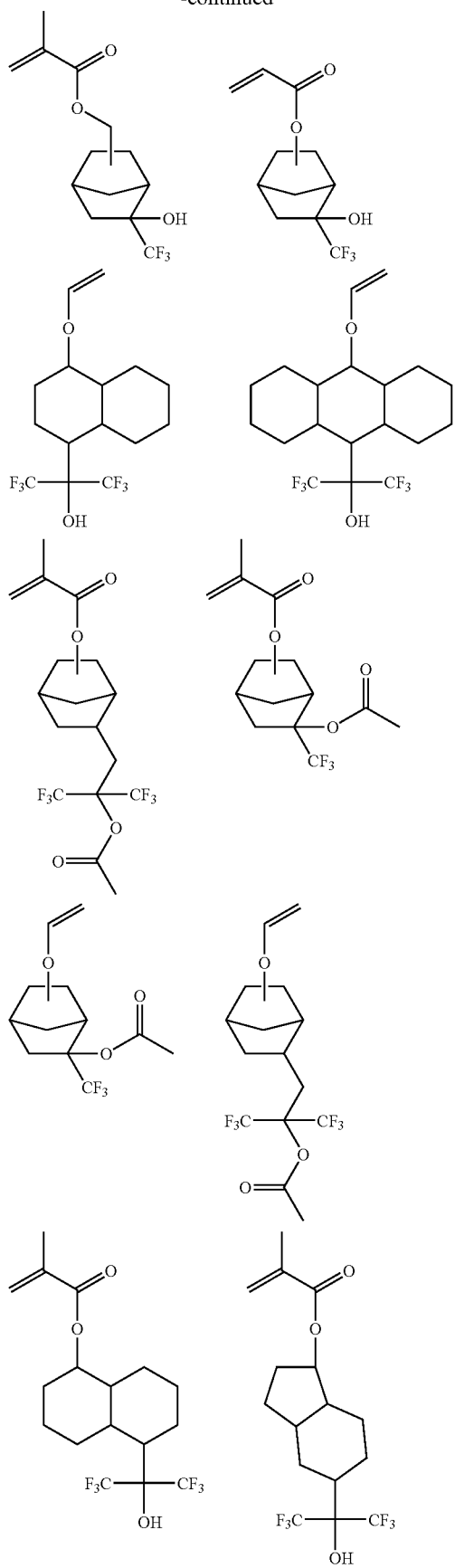
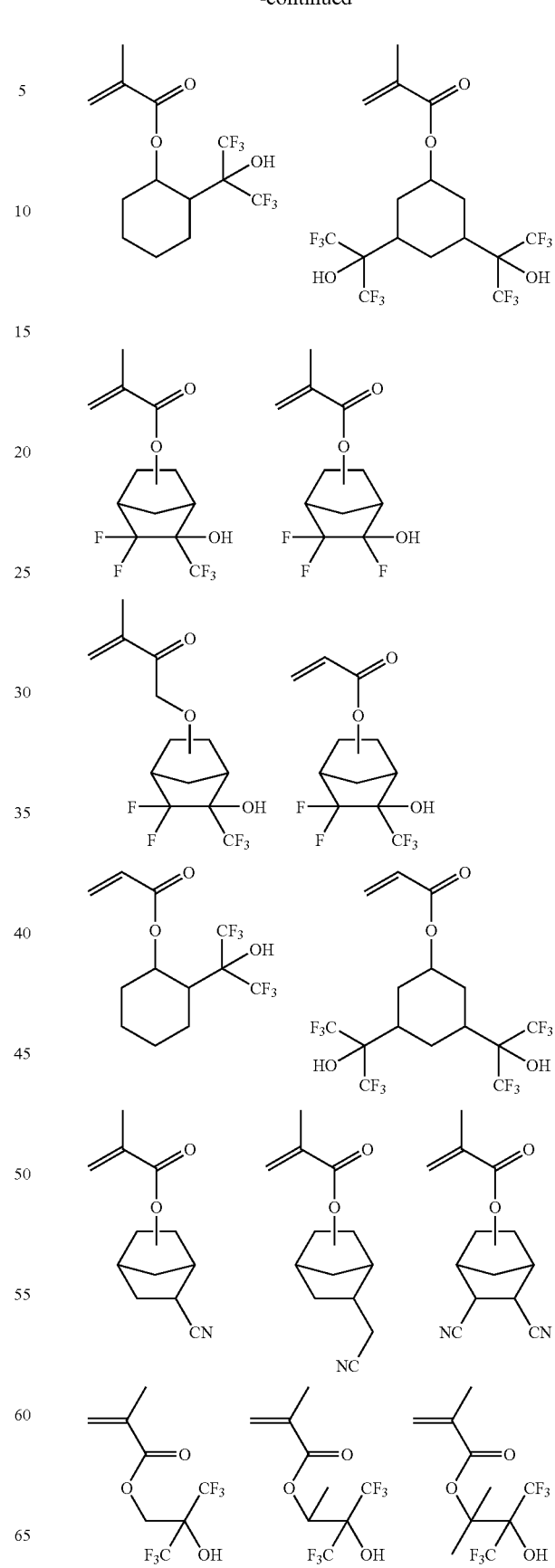

25
-continued
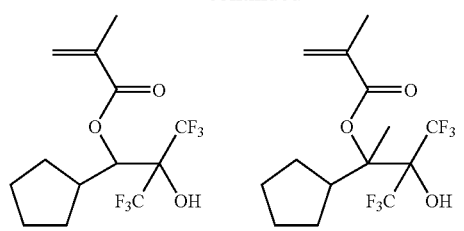
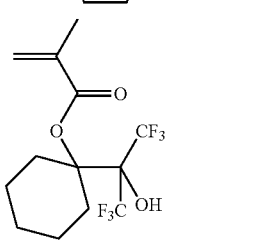
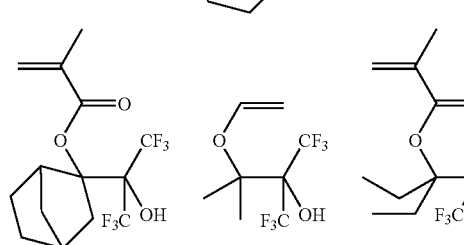
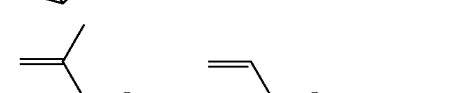
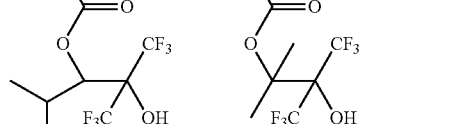
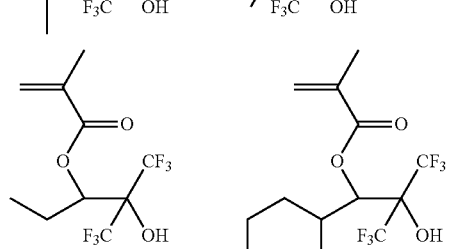
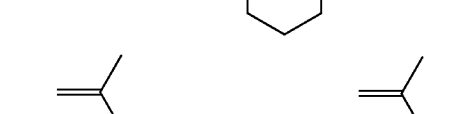
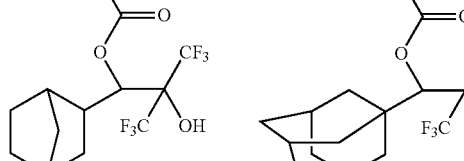
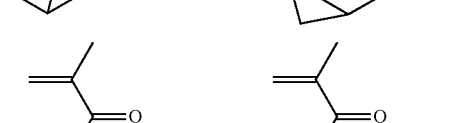
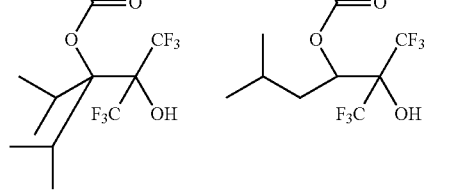
26
-continued
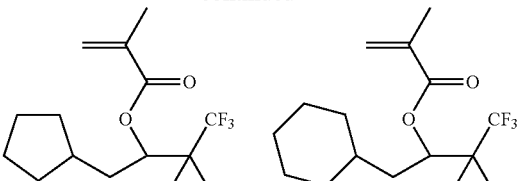
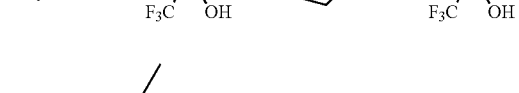
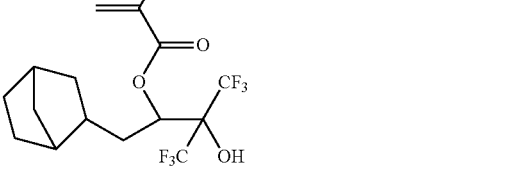
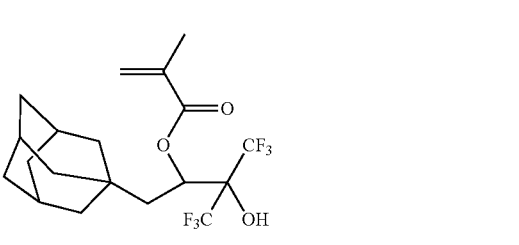
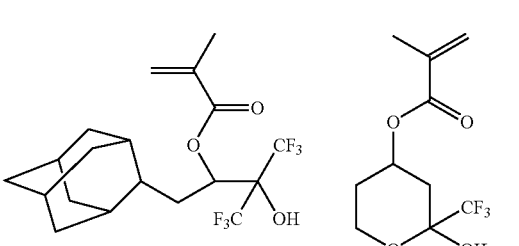
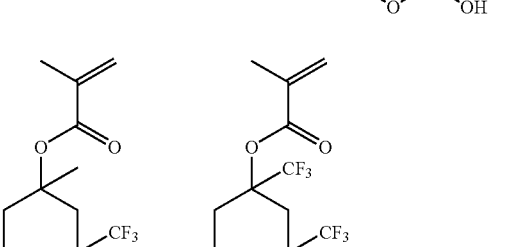
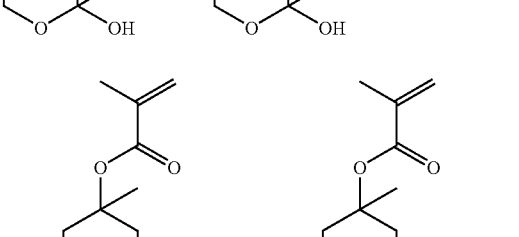
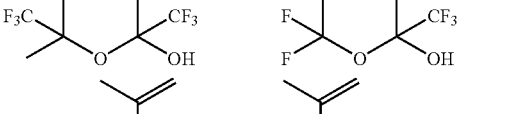
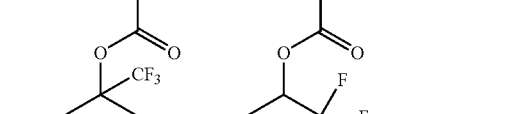
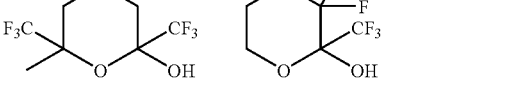

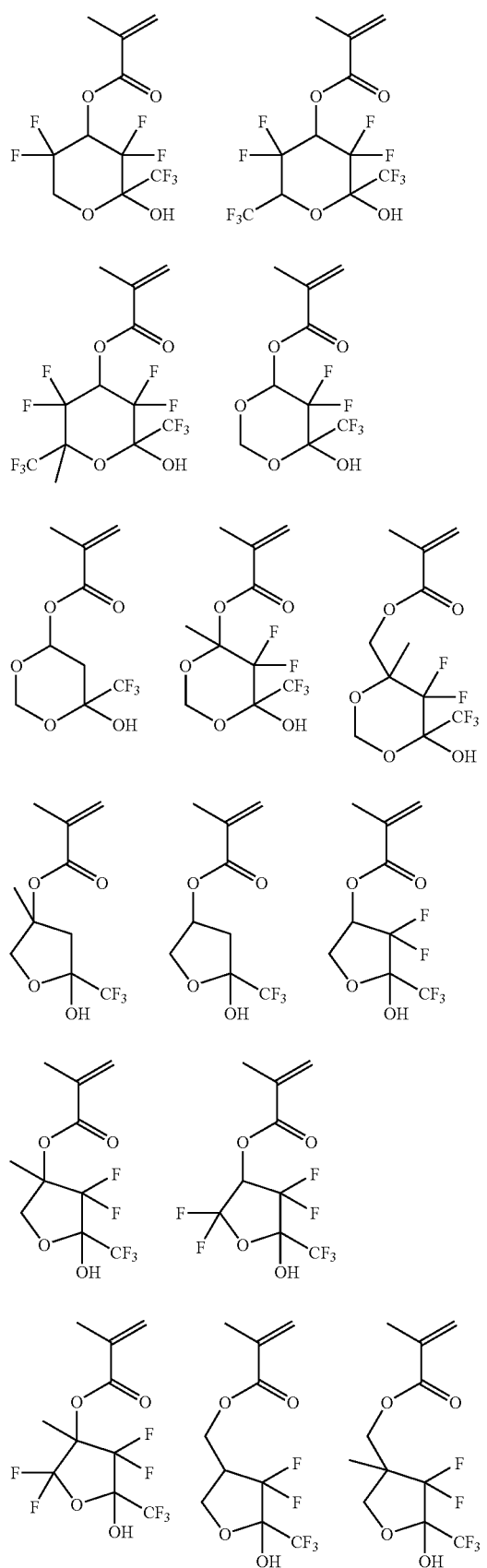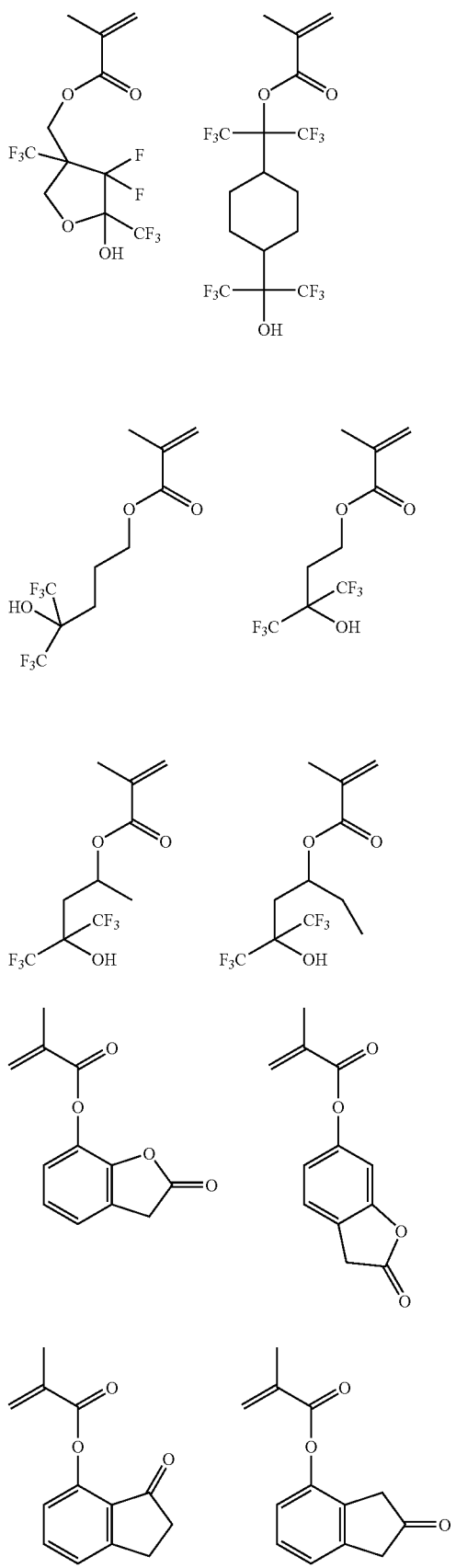

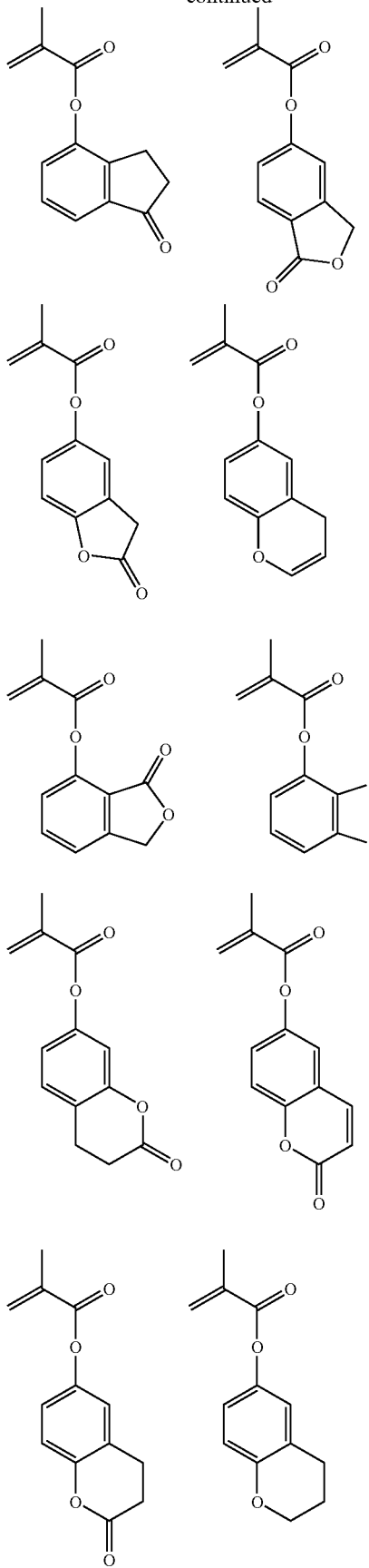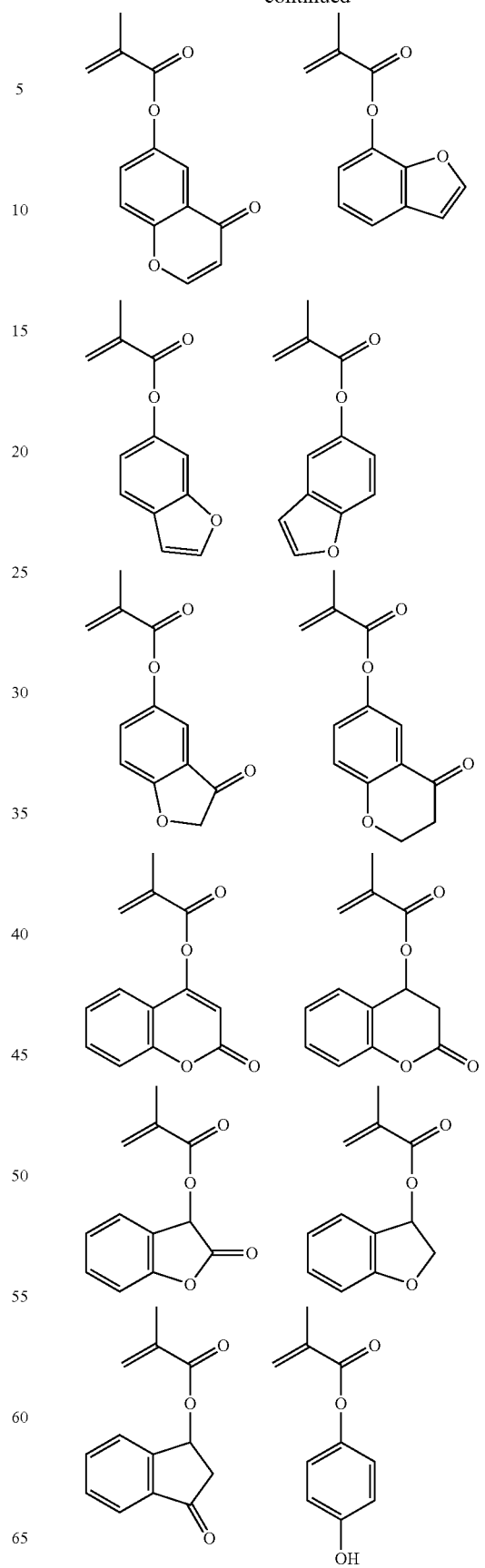

-continued

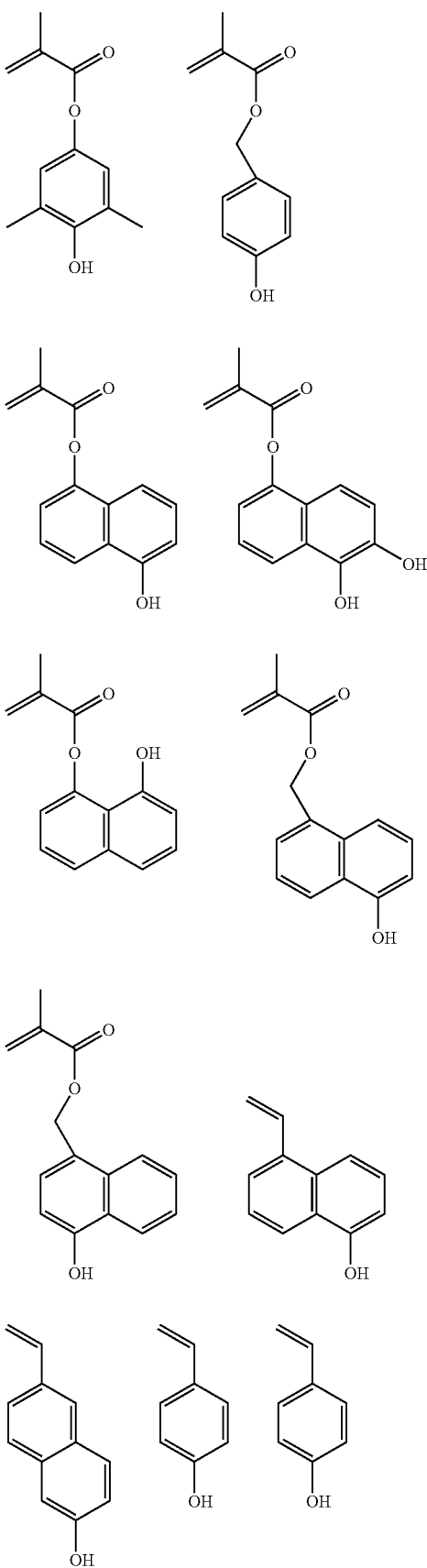

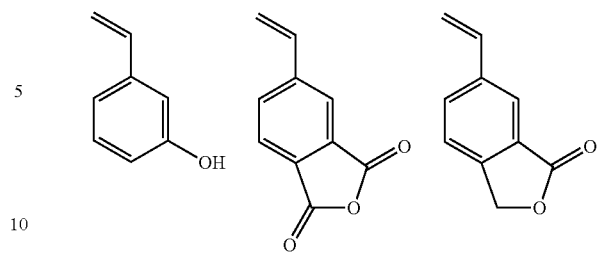

In the case of a monomer containing a hydroxy group, the hydroxy group may be substituted by an acetal group such as an ethoxyethoxy group, which is easily deprotected by an acid during polymerization, and then be deprotected by a weak acid and water after the polymerization. It may also be possible to be substituted by an acetyl group, a formyl group, a pivaloyl group, and the like, and then hydrolyzed by a base after the polymerization.

The repeating unit "a" containing the acid labile group represented by the general formula (2) may be copolymerized with a repeating unit "c" represented by the following general formula (4') such as an indene c1, an acenaphtylene c2, a chromone c3, a coumarin c4, and a norbornadiene c5.

(4')

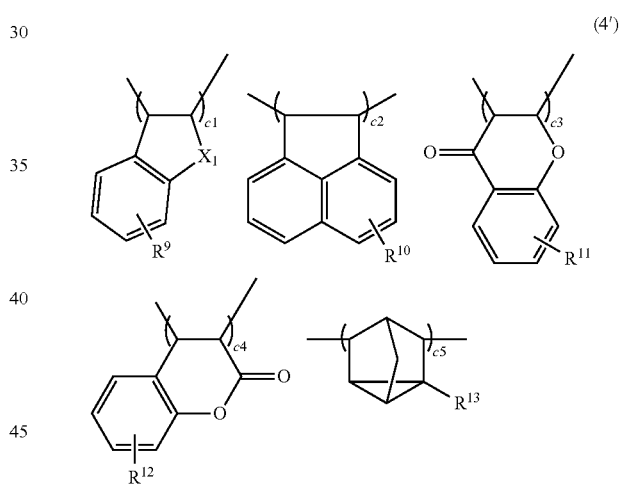

Wherein, each of $R^9$ to $R^{13}$ represents a hydrogen atom; an alkyl group having 1 to 30 carbon atoms; an alkyl group, a hydroxy group, an alkoxy group, an alkanoyl group, or an alkoxycarbonyl group a part or all of whose hydrogen atoms are substituted by a halogen atom; an aryl group having 6 to 10 carbon atoms; a halogen atom; or a 1,1,1,3,3,3-hexafluoro-2-propanol group. $X_1$ represents a methylene group, an oxygen atom, or a sulfur atom.

The polymer of the present invention contains the repeating unit "a" having an acid labile group as the essential requirement, but it may also be copolymerized additionally with a repeating unit "d", a (meth)acrylic ester substituted by the acid labile group, and a repeating unit "e", substituted by an acid labile group $R^{17}$ other than the group shown by the general formula (2), represented by the following general formula (5).

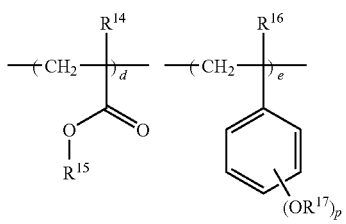

(5)

Wherein, $R^{14}$ and $R^{16}$ represent a hydrogen atom or a methyl group; $R^{15}$ represents an acid labile group; $R^{17}$ represents the acid labile group other than the group shown by the general formula (2); and p represents 1 or 2.

Examples of the copolymerizable repeating units other than repeating units "a", "b", "c", "d", and "e" include styrene, vinyl naphthalene, vinyl anthracene, vinyl pyrene, indole, norbornene, tricyclodecene, tetracyclododecene, methylene indane, (meth)acrylates containing a lactone group, (meth)acrylic acid, 3-hydroxyadamantane (meth) acrylic ester, maleic anhydride, itaconic anhydride, maleimides, and vinyl ethers.

It may also possible to copolymerize an acid generator of onium salt containing a polymerizable olefin group. In Japanese Patent Laid-Open (kokai) No. H4-230645, Japanese Patent Laid-Open (kokai) No. 2005-84365, and Japanese Patent Laid-Open (kokai) No. 2006-045311, a sulfonium salt containing a polymerizable olefin generating specific sulfonic acid and an iodonium salt are proposed. In Japanese Patent Laid-Open (kokai) No. 2006-178317, a sulfonium salt whose sulfonic acid is directly bonded to a main chain is proposed.

In the present invention, repeating units g1, g2, or g3, which contain a sulfonium salt represented by the following general formula (6), may be copolymerized.

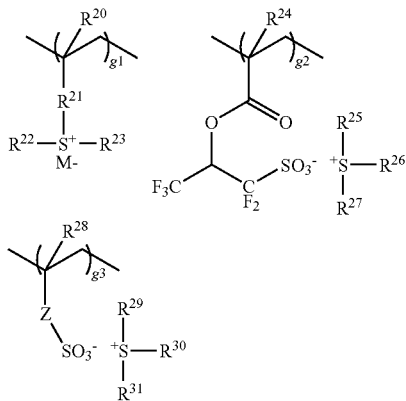

(6)

Wherein, $R^{20}$, $R^{24}$, and $R^{28}$ represent a hydrogen atom or a methyl group; $R^{21}$ represents a phenylene group, an —O—$R^{28'}$— group, or a —C(=O)—Y—$R^{28'}$—group; Y represents an oxygen atom or an NH group; and $R^{28'}$ represents a linear, a branched, or a cyclic alkylene group having 1 to 6 carbon atoms, a phenylene group, or a alkenylene group, optionally containing a carbonyl group, an ester group, an ether group, or a hydroxy group. $R^{22}$, $R^{23}$, $R^{25}$, $R^{26}$, $R^{27}$, $R^{29}$, $R^{30}$, and $R^{31}$ represent the same or a different linear, branched, or cyclic alkyl group having 1 to 12 carbon atoms, optionally containing a carbonyl group, an ester group, or an ether group, or represent an aryl group having 6 to 12 carbon atoms, an aralkyl group having 7 to 20 carbon atoms, or a thiophenyl group; Z represents a single bond, a methylene group, an ethylene group, a phenylene group, a fluorinated phenylene group, an —O—$R^{32}$— group, or a —C(=O)-$Z_1$-$R^{32}$— group; $Z_1$ represents an oxygen atom or an NH group; $R^{32}$ represents a linear, a branched, or a cyclic alkylene group having 1 to 6 carbon atoms, a phenylene group, or a alkenylene group, optionally containing a carbonyl group, an ester group, an ether group, or a hydroxy group; and M⁻ represents a non-nucleophilic counter ion.

The M⁻ non-nucleophilic counter ion may be exemplified by a halide ion such as a chloride ion and a bromide ion; a fluoroalkyl sulfonate such as triflate, 1,1,1-trifluoroethane sulfonate, and nonafluorobutane sulfonate; an aryl sulfonate such as tosylate, benzene sulfonate, 4-fluorobenzene sulfonate, and 1,2,3,4,5-pentafluorobenzene sulfonate; an alkyl sulfonate such as mesylate and butane sulfonate; an imidic acid such as bis(trifluoromethylsulfonyl)imide, bis(perfluoroethylsulfonyl)imide, and bis(perfluorobutylsulfonyl) imide; and a methide acid such as tris(trifluoromethylsulfonyl)methide and tris(perfluoroethylsulfonyl)methide.

Many groups may be selected for the acid labile groups of $R^{15}$ and $R^{17}$ in the general formula (5). They may be the same or different, and in particular a group substituted by the following formulae (A-1) to (A-3) may be exemplified.

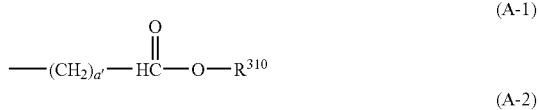

(A-1)

(A-2)

(A-3)

In the formula (A-1), $R^{310}$ represents a tertiary alkyl group having 4 to 20 carbon atoms, preferably 4 to 15 carbon atoms, a trialkyl silyl group whose each alkyl group has 1 to 6 carbon atoms, an oxoalkyl group having 4 to 20 carbon atoms, or a group represented by the above general formula (A-3). Specific examples of the tertiary alkyl group include a tert-butyl group, a tert-amyl group, a 1,1-diethylpropyl group, a 1-ethylcyclopentyl group, a 1-butylcyclopentyl group, a 1-ethylcyclohexyl group, a 1-butylcyclohexyl group, a 1-ethyl-2-cyclopentenyl group, a 1-ethyl-2-cyclohexenyl group, and a 2-methyl-2-adamantyl group. Specific examples of the trialkyl silyl group include a trimethyl silyl group, a triethyl silyl group, and a dimethyl-tert-butyl silyl group. Specific examples of the oxoalkyl group include a 3-oxocyclohexyl group, a 4-methyl-2-oxooxane-4-yl group, and a 5-mehtyl-2-oxooxolane-5-yl group. Here, a' represents an integer of 0 to 6.

In the formula (A-2), each of $R^{311}$ and $R^{32'}$ independently represents any of a hydrogen atom, or a linear, a branched, or a cyclic alkyl group having 1 to 18 carbon atoms, preferably 1 to 10 carbon atoms such as, specifically, a methyl group, an ethyl group, a propyl group, an isopropyl group, a n-butyl group, a sec-butyl group, a tert-butyl group, a cyclopentyl group, a cyclohexyl group, a 2-ethylhexyl group, and a n-octyl group; and $R^{33}$ represents a monovalent hydrocarbon group having 1 to 18 carbon atoms, preferably 1 to 10 carbon atoms, which may contain a hetero atom such as an oxygen atom, including a linear, a branched, or a cyclic alkyl group, a part of whose hydrogen atoms may be substituted by a hydroxy group, an alkoxy group, an oxo group, an amino group, an alkylamino group, and the like. Specific example of them may be a substituted alkyl group and the like as shown below.

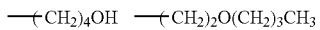

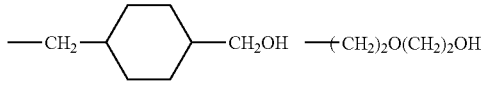

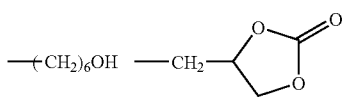

Further, $R^{311}$ and $R^{32'}$, $R^{311}$ and $R^{33}$, and $R^{32'}$ and $R^{33}$ may be bonded to form a ring together with the carbon atoms to which they are bonded. When forming the ring, each of $R^{311}$, $R^{32'}$, and $R^{33}$ represents a linear or a branched alkylene group having 1 to 18 carbon atoms, preferably 1 to 10 carbon atoms. The ring has preferably 3 to 10 carbon atoms, in particular, 4 to 10 carbon atoms.

Specific examples of the acid labile group in the formula (A-1) include tert-butoxy carbonyl group, a tert-butoxy carbonyl methyl group, a tert-amyloxy carbonyl group, a tert-amyloxy carbonyl methyl group, a 1,1-diethylpropyloxy carbonyl group, a 1,1-diethylpropyloxy carbonyl methyl group, a 1-ethylcyclopentyloxy carbonyl group, a 1-ethylcyclopentyloxy carbonyl methyl group, a 1-ethyl-2-cyclopentenyloxy carbonyl group, a 1-ethyl-2-cyclopentenyloxy carbonyl methyl group, a 1-ethoxyethoxy carbonyl methyl group, a 2-tetrahydropyranyloxy carbonyl methyl group, and a 2-tetrahydrofuranyloxy carbonyl methyl group.

Further, there may also be mentioned substituent groups represented by the following formulae (A-1)-1 to (A-1)-10.

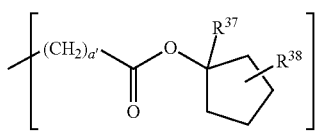
(A-1)-1

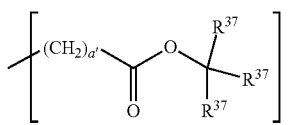
(A-1)-2

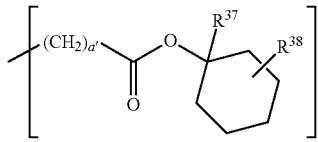
(A-1)-3

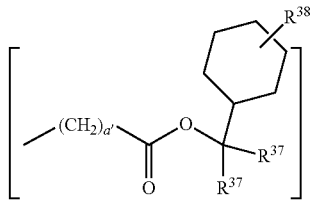
(A-1)-4

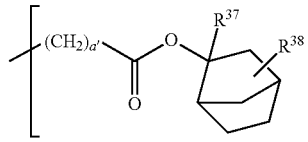
(A-1)-5

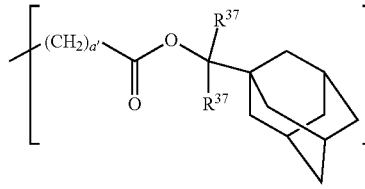
(A-1)-6

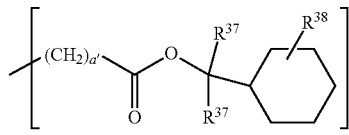
(A-1)-7

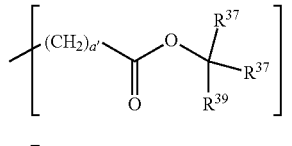
(A-1)-8

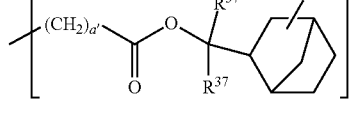
(A-1)-9

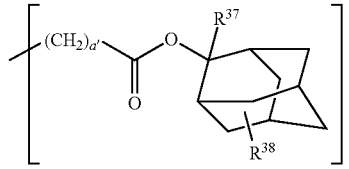
(A-1)-10

Here, a' represents the same meaning as before. Each of $R^{37}$ represents the same or different linear, branched, or cyclic alkyl group having 1 to 10 carbon atoms, or an aryl group having 6 to 20 carbon atoms; and $R^{38}$ represents a hydrogen atom, or a linear, a branched, or a cyclic alkyl group having 1 to 10 carbon atoms.

Further, each of $R^{39}$ represents the same or different linear, branched, or cyclic alkyl group having to 10 carbon atoms, or an aryl group having 6 to 20 carbon atoms.

Among the acid labile groups represented by the formula (A-2), the linear or the branched group may be exemplified by the groups shown by the following formulae (A-2)-1 to (A-2)-23.

—CH$_2$—O—CH$_3$ (A-2)-1

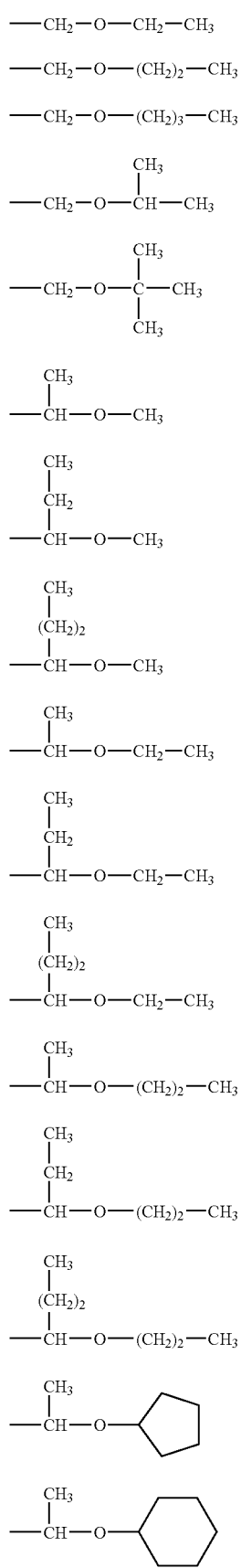
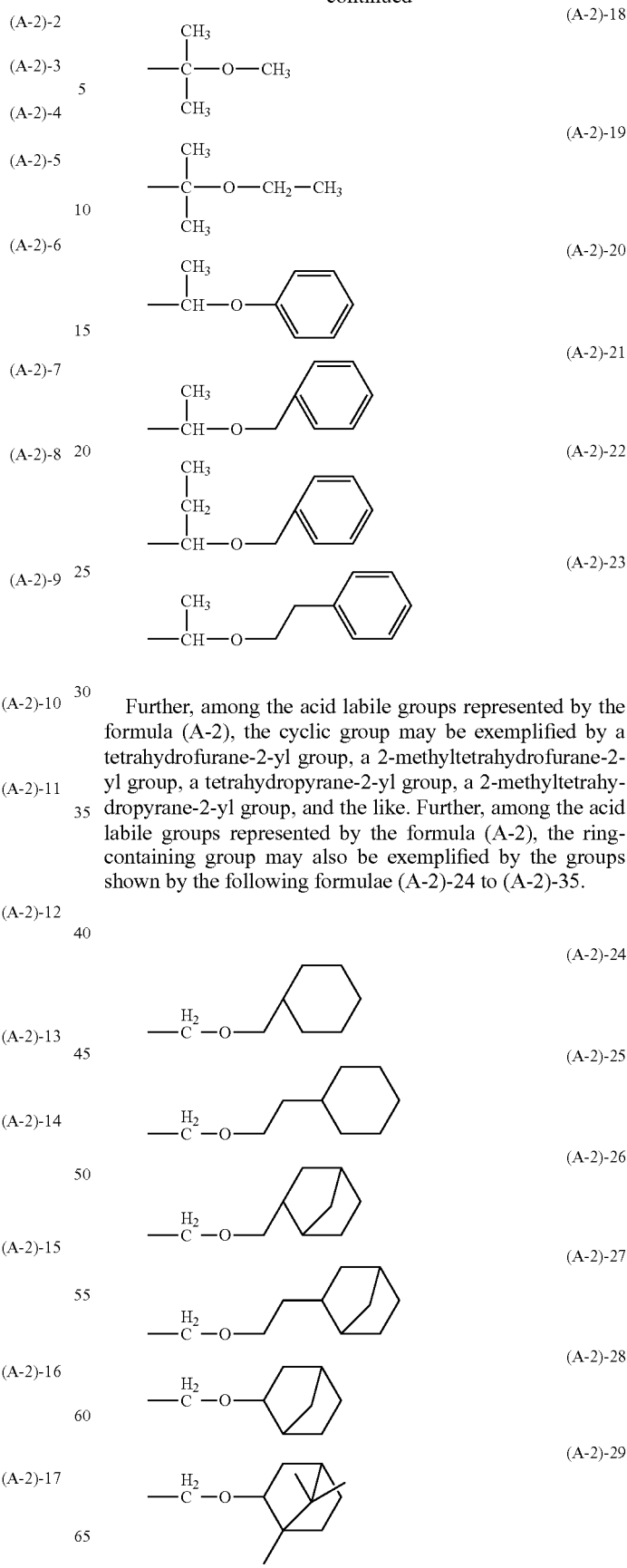

Further, among the acid labile groups represented by the formula (A-2), the cyclic group may be exemplified by a tetrahydrofurane-2-yl group, a 2-methyltetrahydrofurane-2-yl group, a tetrahydropyrane-2-yl group, a 2-methyltetrahydropyrane-2-yl group, and the like. Further, among the acid labile groups represented by the formula (A-2), the ring-containing group may also be exemplified by the groups shown by the following formulae (A-2)-24 to (A-2)-35.

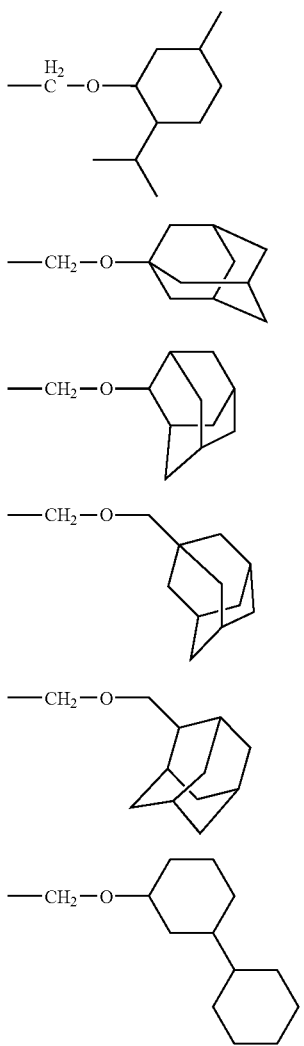

In addition, a base resin may be crosslinked intramolecularly or intermolecularly by the acid labile group represented by the following general formula (A-2a) or (A-2b).

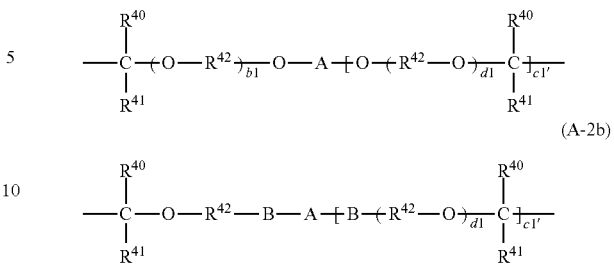

Wherein, each of $R^{40}$ and $R^{41}$ represents a hydrogen atom, or a linear, a branched, or a cyclic alkyl group having 1 to 8 carbon atoms. Here, $R^{40}$ and $R^{41}$ may be bonded to form a ring together with the carbon atoms to which they are bonded. When forming the ring, each of $R^{40}$ and $R^{41}$ represents a linear or a branched alkylene group having 1 to 8 carbon atoms; $R^{42}$ represents a linear, a branched, or a cyclic alkylene group having 1 to 10 carbon atoms; each of b1 and d1 represents 0 or an integer of 1 to 10, preferably 0 or an integer of 1 to 5; and c1' represents an integer of 1 to 7. Further, A represents an aliphatic or an alicyclic saturated hydrocarbon group with a (c1'+1)-valency having 1 to 50 carbon atoms, an aromatic hydrocarbon group, or a heterocyclic group. These groups may be intervened by a hetero atom, or a part of the hydrogen atoms attached to their carbon atom may be substituted by a hydroxy group, a carboxyl group, a carbonyl group, or a fluorine atom. Also, B represents a —CO—O— group, a —NHCO—O— group, or a —NHCONH— group.

In this case, A is preferably a linear, a branched, or a cyclic alkylene group with a valency of 2 to 4 having 1 to 20 carbon atoms, an alkyl triyl group, an alkyl tetrayl group, or an arylene group having 6 to 30 carbon atoms. These groups may be intervened by a hetero atom, and a part of the hydrogen atoms attached to their carbon atom may be substituted by a hydroxy group, a carboxyl group, an acyl group, or a halogen atom. Here, c1' represents preferably an integer of 1 to 3.

The crosslinkable acetal groups represented by the general formulae (A-2a) and (A-2b) may be specifically exemplified by the groups shown by the following formulae (A-2)-37 to (A-2)-44.

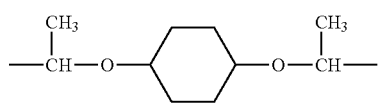

-continued

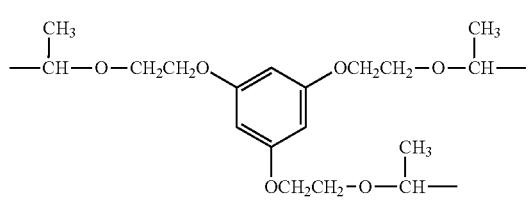
(A-2)-43

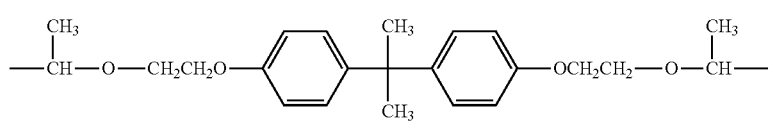
(A-2)-44

Further, in the formula (A-3), each of $R^{34}$, $R^{35}$ and $R^{36}$ represents a monovalent hydrocarbon groups such as a linear, a branched, or a cyclic monovalent alkyl group having 1 to 20 carbon atoms, optionally containing a hetero atom such as an oxygen atom, a sulfur atom, a nitrogen atom, and a fluorine atom. $R^{34}$ and $R^{35}$, $R^{34}$ and $R^{36}$, and $R^{35}$ and $R^{36}$ may be bonded with each other to form a ring having 3 to 20 carbon atoms together with the carbon atoms to which they are bonded.

The tertiary alkyl group represented by the formula (A-3) may be exemplified by a tert-butyl group, a triethyl carbyl group, a 1-ethylnorbornyl group, a 1-methylcyclohexyl group, a 1-ethylcyclopentyl group, a 2-(2-methyl)adamantyl group, a 2-(2-ethyl)adamantyl group, a tert-amyl group, and the like.

Further, specifically the tertiary alkyl group may be exemplified by the groups shown by the following formulae (A-3)-1 to (A-3)-18.

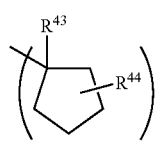
(A-3)-1

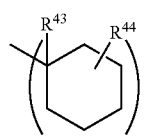
(A-3)-2

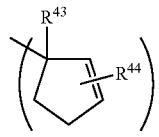
(A-3)-3

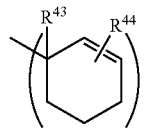
(A-3)-4

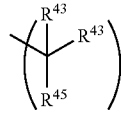
(A-3)-5

-continued

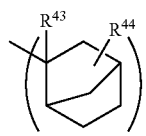
(A-3)-6

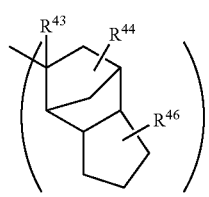
(A-3)-7

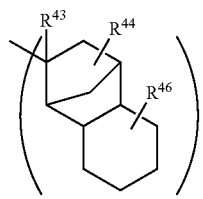
(A-3)-8

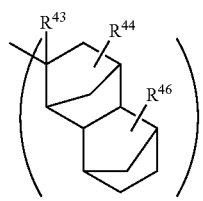
(A-3)-9

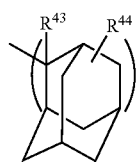
(A-3)-10

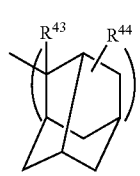
(A-3)-11

(A-3)-12 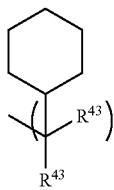

(A-3)-13 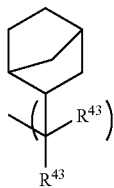

(A-3)-14 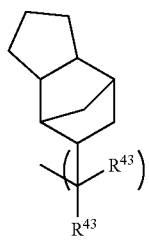

(A-3)-15 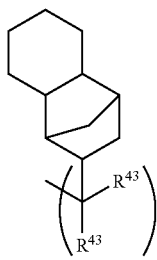

(A-3)-16 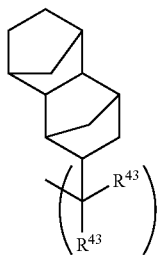

(A-3)-17 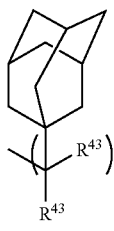

(A-3)-18 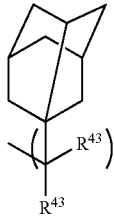

In the formulae (A-3)-1 to (A-3)-18, $R^{43}$ represents the same or different linear, branched, or cyclic alkyl group having 1 to 8 carbon atoms, or an aryl group such as a phenyl group having 6 to 20 carbon atoms; each of $R^{44}$ and $R^{46}$ represents a hydrogen atom, or a linear, a branched, or a cyclic alkyl group having 1 to 20 carbon atoms; and $R^{45}$ represents an aryl group such as a phenyl group having 6 to 20 carbon atoms.

Further, as shown by the following formulae (A-3)-19 and (A-3)-20, a polymer may contain $R^{47}$ represents an alkylene group or an arylene group with the valency of 2 or more, by which a polymer is crosslinked intramolecularly or intermolecularly.

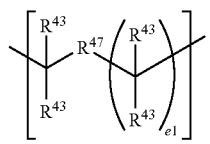
(A-3)-19

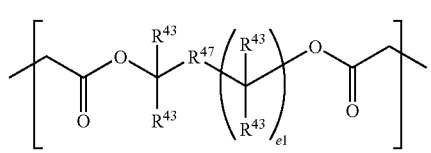
(A-3)-20

In the formulae (A-3)-19 and (A-3)-20, $R^{43}$ represents the same meaning as before; and $R^{47}$ represents a linear, a branched, or a cyclic alkylene group having 1 to 20 carbon atoms, or an arylene group such as a phenylene group, and optionally containing a hetero atom such as an oxygen atom, a sulfur atom, and a nitrogen atom. Here, e1 represents an integer of 1 to 3.

$R^{310}$, $R^{33}$ and $R^{36}$ in the formulae (A-1), (A-2), (A-3) may be exemplified by a substituted or un-substituted aryl group such as a phenyl group, a p-methylphenyl group, a p-ethylphenyl group, and an alkoxy-substituted phenyl group such as a p-methoxyphenyl group; an aralkyl group such as a benzyl group and a phenetyl group; an alkyl group or an oxoalkyl group shown by the below formulae, in which the above-mentioned groups contain an oxygen atom, or are substituted by a hydroxy group at the hydrogen atom attached to their carbon atom, or two hydrogen atoms of them are substituted by an oxygen atom to form a carbonyl group.

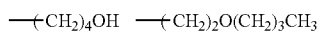

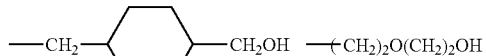

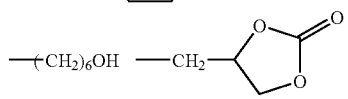

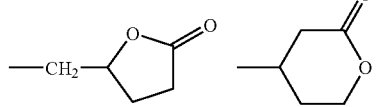

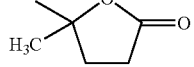

As the acid labile group of (A-3), a repeating unit of a (meth)acrylic ester having the exo structure as shown by the following A-3-21 may be cited as a preferable example.

A-3-21

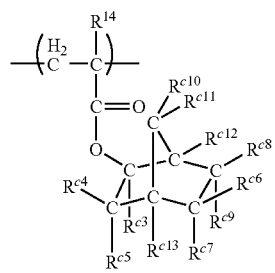

Wherein, $R^{14}$ represents the same meanings as before; $R^{c3}$ represents a linear, a branched, or a cyclic alkyl group having 1 to 8 carbon atoms, or an aryl group having 6 to 20 carbon atoms optionally substituted. Each of $R^{c4}$ to $R^{c9}$, $R^{c12}$, and $R^{c13}$ independently represents a hydrogen atom, or a monovalent hydrocarbon group having 1 to 15 carbon atoms optionally containing a hetero atom; each of $R^{c10}$ and $R^{c11}$ represents a hydrogen atom. Alternatively, $R^{c4}$ and $R^{c5}$, $R^{c6}$ and $R^{c8}$, $R^{c6}$ and $R^{c9}$, $R^{c7}$ and $R^{c9}$, $R^{c7}$ and $R^{c13}$, $R^{c8}$ and $R^{c12}$, $R^{c10}$ and $R^{c11}$, or $R^{c11}$ and $R^{c12}$ may form a ring with each other, and in that case they represent a divalent hydrocarbon group having 1 to 15 carbon atoms optionally containing a hetero atom. Further, $R^{c4}$ and $R^{c13}$, $R^{c10}$ and $R^{c13}$, or $R^{c6}$ and $R^{c8}$ may form a double bond by a direct bond between groups connected to neighboring carbons. Furthermore, the formula also represents its mirror image.

Here, an ester monomer to obtain a repeating unit having the exo structure as shown in the general formula A-3-21 is disclosed in the Japanese Patent Laid-Open (kokai) No. 2000-327633.

Specific examples may be cited in the following, but not restricted to them.

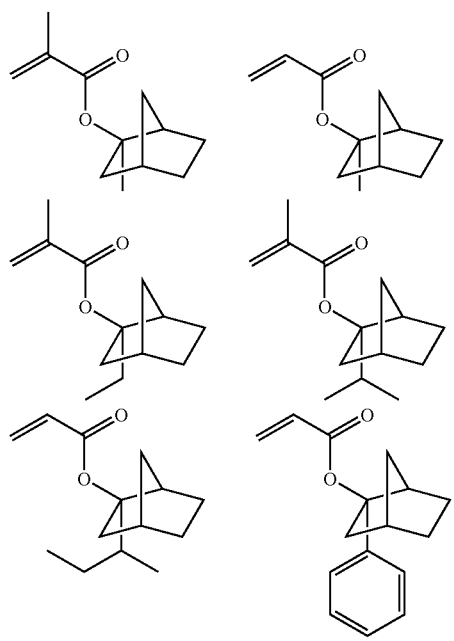

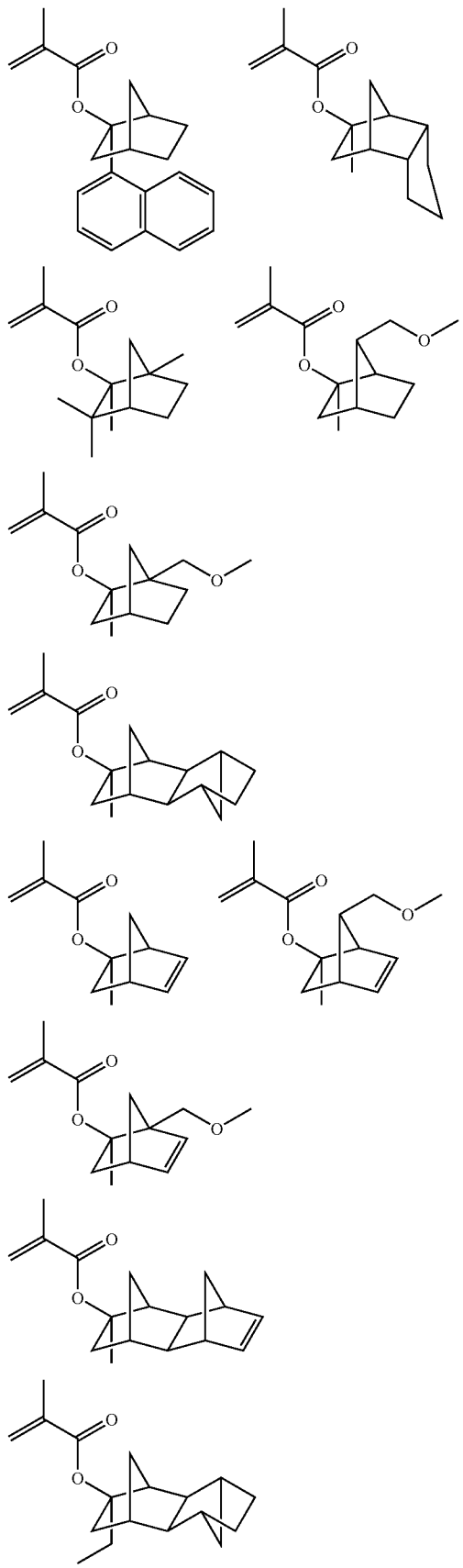

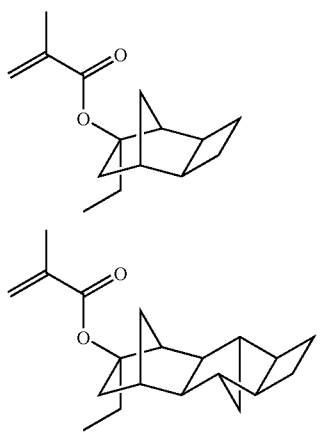

Further, the acid labile groups shown in (A-3) may be exemplified by the acid labile group having a (meth)acrylic ester which contains a furane diyl group, a tetrahydrofurane diyl group, or an oxanorbornane diyl group, as shown by A-3-22.

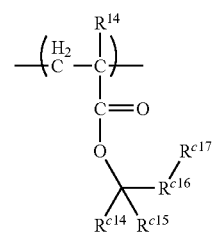

A-3-22

Wherein, $R^{14}$ represents the same meaning as before. Each of $R^{c14}$ and $R^{c15}$ independently represents a linear, a branched, or a cyclic monovalent hydrocarbon group having 1 to 10 carbon atoms. Alternatively, $R^{c14}$ and $R^{c15}$ may form an aliphatic hydrocarbon ring, by bonding with each other, together with the carbon atoms to which they are bonding. $R^{c16}$ represents a divalent group selected from a furane diyl group, a tetrahydrofurane diyl group, or an oxanorbornane diyl group; and $R^{c17}$ represents a hydrogen atom, or a linear, a branched, or a cyclic monovalent hydrocarbon group having 1 to 10 carbon atoms optionally containing a hetero atom.

The monomers to obtain a repeating unit, which is substituted by the acid labile group containing a furane diyl group, a tetrahydrofurane diyl group, or an oxanorbornane diyl group may be exemplified by the following.

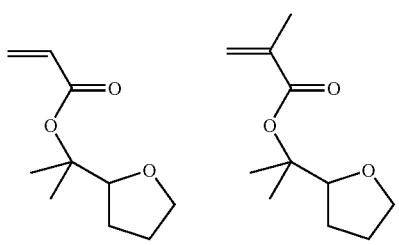

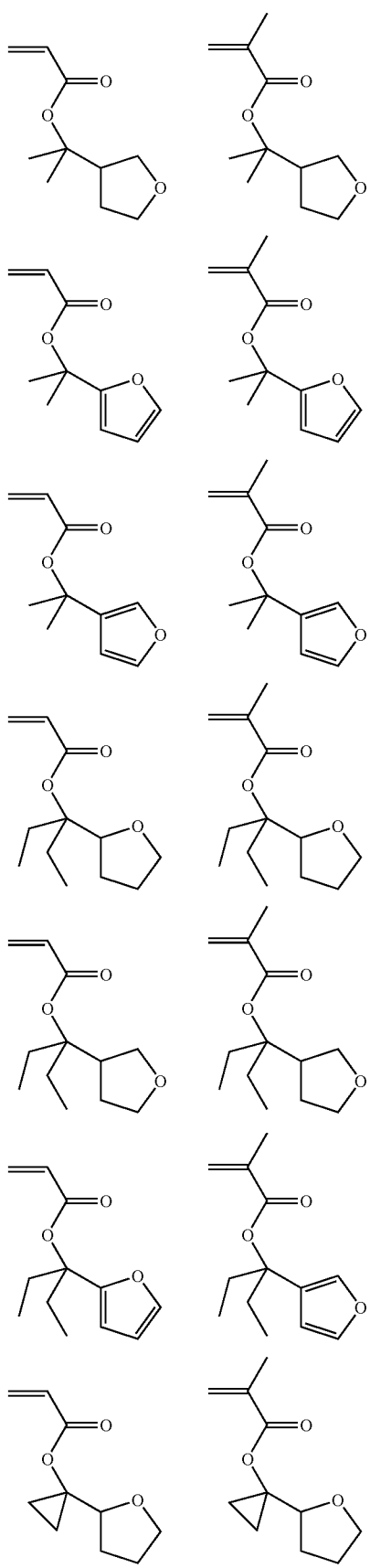

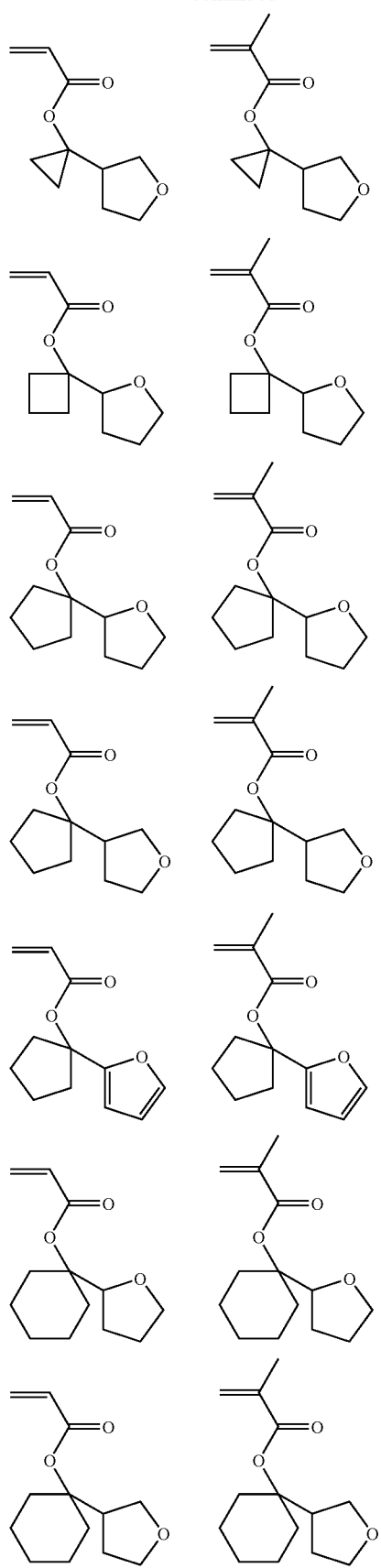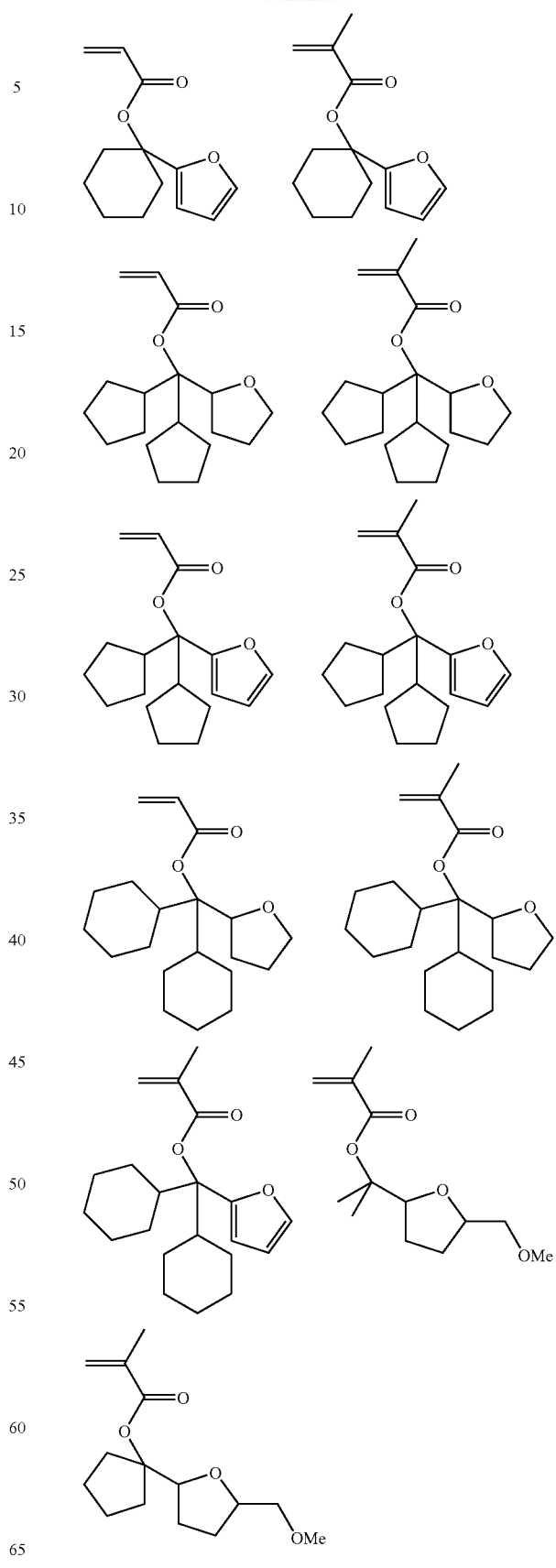

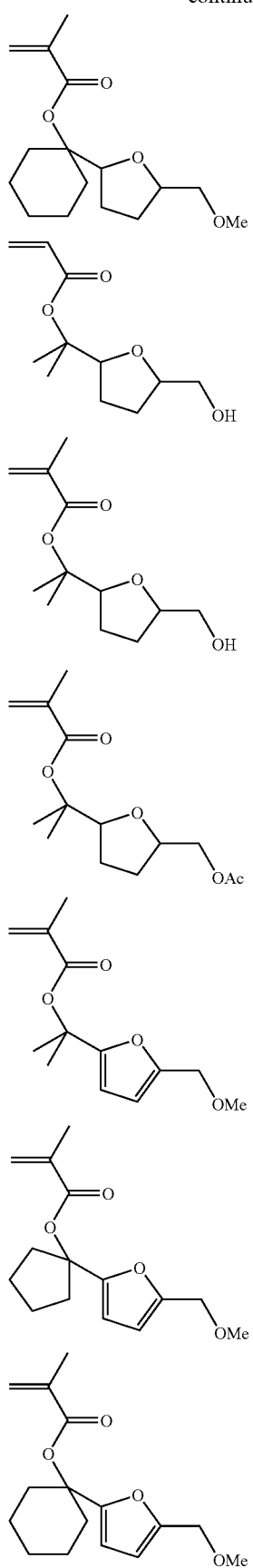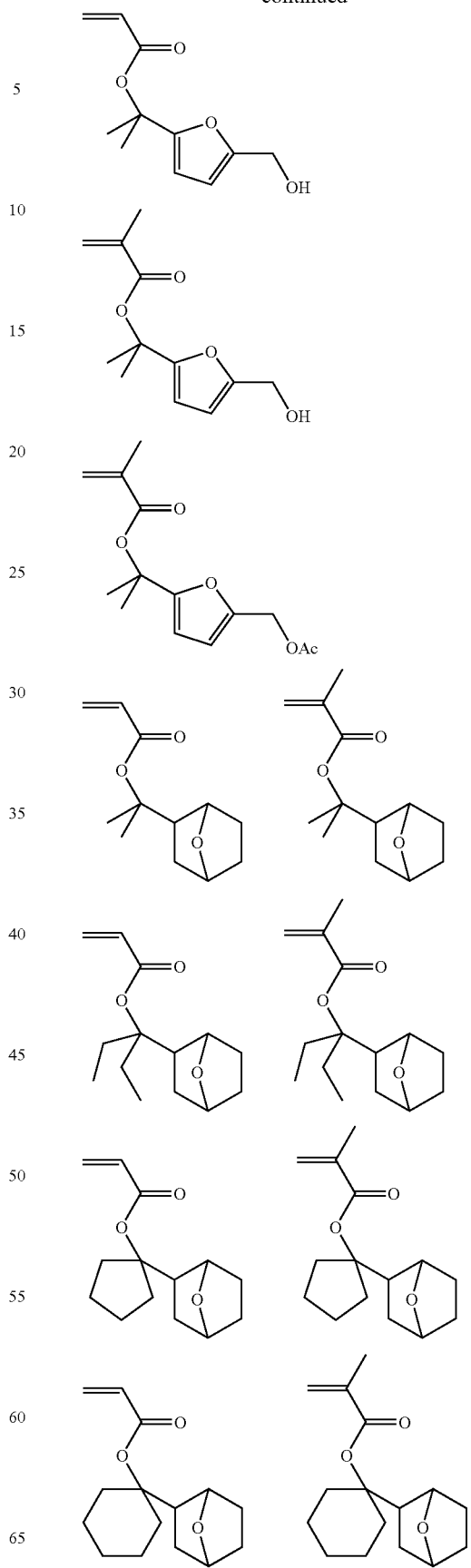

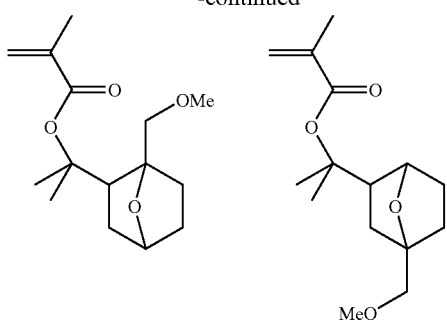
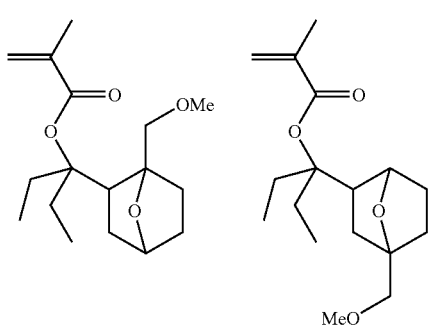
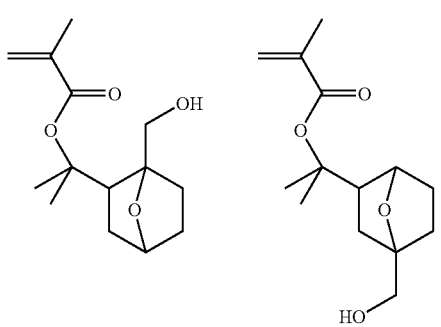
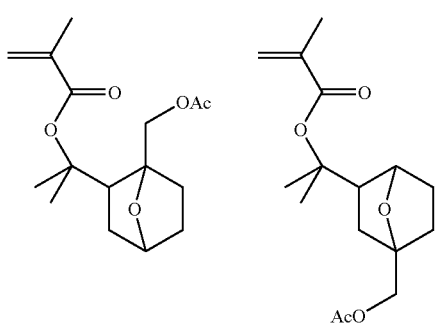
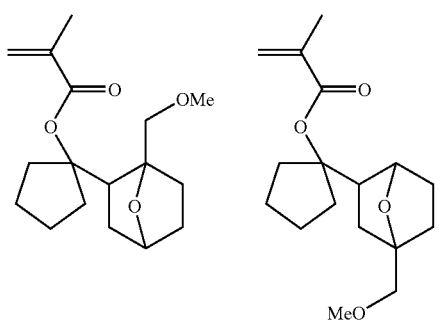
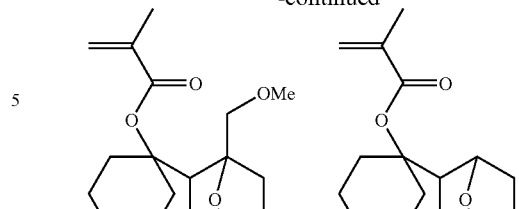
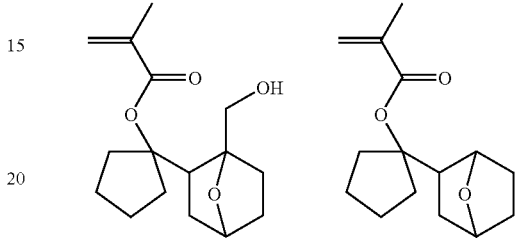
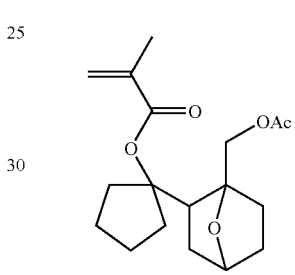

One exemplary method for synthesizing the polymer as the copolymer in the present invention may be following: a monomer shown by the repeating unit "a" as mentioned before is heated for a thermal polymerization by adding a radical polymerization initiator in an organic solvent to obtain a polymer as a copolymer.

The solvent used in the polymerization reaction may be exemplified by toluene, benzene, tetrahydrofurane, diethyl ether, dioxane, and the like. The polymerization initiator may be exemplified by 2,2'-azobisisobutyronitrile (AIBN), 2,2'-azobis(2,4-dimethylvaleronitrile), dimethyl 2,2-azobis(2-methylpropionate), benzoyl peroxide, lauroyl peroxide, and the like. The polymerization reaction may be carried out preferably by heating at 50 to 80° C. The reaction time is 2 to 100 hours, and preferably 5 to 20 hours.

When the copolymer of the present invention is copolymerized with hydroxy styrene or hydroxy vinyl naphthalene, there may also be a method to use, in stead of a hydroxy styrene or a hydroxy vinyl naphthalene, an acetoxy styrene or an acetoxy vinyl naphthalene, wherein the acetoxy group is deprotected by the alkaline hydrolysis as mentioned above after the polymerization to obtain a poly(hydroxy styrene) or a poly(hydroxy vinyl naphthalene).

The basic compound used for the alkaline hydrolysis may be exemplified by an aqueous ammonium, triethylamine, and the like. The reaction temperature is −20 to 100° C., and preferably 0 to 60° C. The reaction time is 0.2 to 100 hours, and preferably 0.5 to 20 hours.

The weight-average molecular weight of the polymer of the present invention is 1,000 to 500,000, and preferably 2,000 to 30,000. When the weight-average molecular weight is 1,000 or more, the resist composition is excellent in its heat resistance, and when it is 500,000 or less, dissolution in a basic solution is facilitated, thereby lowering a risk of a footing profile after the patterning, thus this region is preferable.

Further, in the polymer of the present invention, the molecular weight distribution (Mw/Mn) of a multi-components copolymer is preferably 1.0 to 2.0, while a narrow range of 1.0 to 1.5 is more preferable. If the molecular weight distribution (Mw/Mn) of a multi-components copolymer is in this range, there is lowered risk of forming foreign spots on the pattern and deterioration of the pattern configuration after exposure, thus this range is preferable because the resist composition suitably useful for fine pattern size may be obtained.

Further, it may also be possible to blend two or more polymers having different component ratios, molecular weight distributions, and molecular weights.

The polymer of the present invention is suitable as the base resin for a positive resist composition. The positive resist composition obtained by blending this polymer as the base resin with an organic solvent, an acid generator, a dissolution inhibitor, a basic compound, a surfactant, and the like in an appropriate composition ratio depending on the purpose can accelerate the dissolution rate of the polymer into a developer by a catalysis reaction in an exposed area. Therefore, the positive resist composition having an extremely high sensitivity, a large exposure allowance, a good process applicability, a further excellent etching resistance with a good pattern configuration after the exposure, a small sparse-dense size difference particularly owing to a depressed diffusion of an acid. Because of the above-mentioned advantages, the positive resist composition having a high practicality and a high validity as the resist composition for the VLSI manufacture may be made. Especially the chemically amplified positive resist composition utilizing an acid catalysis reaction by an acid generator contained therein has a high sensitivity and various further improved properties, and thus is extremely useful.

In other word, the degree of resolution may be further improved by blending a dissolution inhibitor into the positive resist composition, since the difference of dissolution rates between an exposed area and an non-exposed area is further increased.

Furthermore, by adding a basic compound, for example, a diffusion rate of an acid in the resist film may be suppressed so that the degree of resolution may be further improved, and by adding a surfactant, coating properties of the resist composition may be further improved or controlled.

Thus, the positive resist composition of the present invention may contain an organic solvent, a compound generating an acid by response to a high energy beam (an acid generator), and optionally a dissolution inhibitor, a basic compound, a surfactant, and other components. As an organic solvent to be used for the positive resist composition of the present invention, particularly for the chemically amplified positive resist composition, any organic solvents may be used as far as it can dissolve a base resin, an acid generator, and other additives, and the like. Examples of such organic solvents include ketones such as cyclohexanone and methyl 2-n-amyl ketone; alcohols such as 3-methoxy buthanol, 3-methyl-3-methoxy buthanol,. 1-methoxy-2-propanol, and 1-ethoxy-2-propanol; ethers such as propyleneglycol monomethyl ether, ethyleneglycol monomethyl ether, propyleneglycol monoethyl ether, ethyleneglycol monoethyl ether, propyleneglycol dimethyl ether, and diethyleneglycol dimethyl ether; esters such as propyleneglycol monomethyl ether acetate, propyleneglycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propyleneglycol mono-tert-butyl ether acetate; and lactones such as γ-butyrolactone, though it is not restricted to the above solvents.

These organic solvents may be used singly, or in a mixture of two or more kinds. In the present invention, among these organic solvents, in view of the highest solubility of the acid generator contained in the resist components, diethyleneglycol dimethyl ether, 1-ethoxy-2-propanol, propyleneglycol monomethyl ether acetate, and a mixture thereof are preferably used.

The amount of the organic solvent to be used is preferably 200 to 1,000 parts (hereinafter "by weight" after "parts" is neglected in this document), and more preferably 400 to 800 parts, relative to 100 parts of the base resin.

The acid generator blended in the positive resist composition of the present invention may be exemplified by:
(i) an onium salt represented by the following general formula (P1a-1), (P1a-2), or (P1b),
(ii) a diazomethane derivative represented by the following general formula (P2),
(iii) a glyoxime derivative represented by the following general formula (P3),
(iv) a bissulfone derivative represented by the following general formula (P4),
(v) a sulfonate ester of N-hydroxyimide compound represented by the following general formula (P5),
(vi) a β-ketosulfonic acid derivative,
(vii) a disulfone derivative,
(viii) a nitrobenzyl sulfonate derivative,
(ix) a sulfonate ester derivative, and the like.

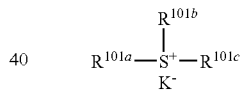
(P1a-1)

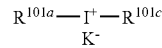
(P1a-2)

Wherein, each of $R^{101a}$, $R^{101b}$, and $R^{101c}$ represents a linear, a branched, or a cyclic alkyl group, an alkenyl group, an oxoalkyl group or an oxoalkenyl group having 1 to 12 carbon atoms, an aryl group having 6 to 20 carbon atoms, or an aralkyl group or an aryloxoalkyl group having 7 to 12 carbon atoms, wherein a part or all of hydrogen atoms in these groups may be substituted by an alkoxy group and the like; $R^{101b}$ and $R^{101c}$ may form a ring, and when a ring is formed; each of $R^{101b}$ and $R^{101c}$ represents an alkylene group having 1 to 6 carbon atoms; and $K^-$ represents a non-nucleophilic counter ion.

The above-mentioned $R^{101a}$, $R^{101b}$, and $R^{101c}$ may be the same or different, and specifically include, as the alkyl group, a methyl group, an ethyl group, a propyl group, an isopropyl group, a n-butyl group, a sec-butyl group, a tert-butyl group, a pentyl group, a hexyl group, a heptyl group, an octyl group, a cyclopentyl group, a cyclohexyl group, a cycloheptyl group, a cyclopropylmethyl group, a 4-methylcyclohexyl group, a cyclohexylmethyl group, a norbornyl group, an admantyl group, and the like. The alkenyl group may be exemplified by a vinyl group, an allyl group, a propenyl group, a buthenyl group, a hexenyl group, a cyclohexenyl group, and the like.

The oxoalkyl group may be exemplified by a 2-oxocyclopentyl group, 2-oxocyclohexyl group, and the like, and in addition by a 2-oxopropyl group, a 2-cyclopentyl-2-oxoethyl group, a 2-cyclohexyl-2-oxoethyl group, a 2-(4-methylcyclohexyl)-2-oxoethyl group, and the like. The oxoalkenyl group may be exemplified by 2-oxo-4-cyclohexenyl group, 2-oxo-4-propenyl group, and the like. The aryl group may be exemplified by a phenyl group, a naphthyl group, and the like; an alkoxyphenyl group such as a p-methoxyphenyl group, a m-methoxyphenyl group, an o-methoxyphenyl group, an ethoxyphenyl group, a p-tert-butoxyphenyl group, and a m-tert-butoxyphenyl group; an alkylphenyl group such as a 2-methylphenyl group, a 3-methylphenyl group, a 4-methylphenyl group, an ethylphenyl group, a 4-tert-butylphenyl group, a 4-butylphenyl group, and a dimethylphenyl group; an alkylnaphthyl group such as a methylnaphthyl group and an ethylnaphthyl group; an alkoxynaphthyl group such as a methoxynaphthyl group and an ethoxynaphtyl group; a dialkylnaphthyl group such as a dimethylnaphthyl group and a diethylnaphthyl group; a dialkoxynaphthyl group such as dimethoxynaphthyl group and a diethoxynaphthyl group; and others. The aralkyl group may be exemplified by a benzyl group, a phenylethyl group, a phenetyl group, and the like. The aryloxoalkyl group may be exemplified by a 2-aryl-2-oxoethyl group such as a 2-phenyl-2-oxoethyl group, a 2-(1-naphthyl)-2-oxoethyl group, and a 2-(2-naphthyl)-2-oxoethyl group. The non-nucleophilic counter ion K⁻ may be exemplified by a halide ion such as a chloride ion and a bromide ion; a fluoroalkyl sulfonate such as triflate, 1,1,1-trifluoroethane sulfonate, and nonafluorobutane sulfonate; an aryl sulfonate such as tosylate, benzene sulfonate, 4-fluorobenzene sulfonate, and 1,2,3,4,5-pentafluorobenzene sulfonate; an alkyl sulfonate such as mesylate and butane sulfonate; an imidic acid such as bis(trifluoromethylsulfonyl)imide, bis(perfluoroethylsulfonyl)imide, and bis(perfluorobutylsulfonyl)imide; a methide acid such as tris(trifluoromethylsulfonyl)methide and tris(perfluoroethylsulfonyl)methide; and further a sulfonate whose α-position is substituted by a fluorine atom as shown by the following general formula K-2, and a sulfonate whose α and β positions are substituted by a fluorine atom as shown by K-1.

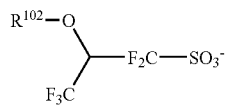

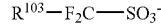

In the general formula (K-1), $R^{102}$ represents a hydrogen atom, a linear, a branched, or a cyclic alkyl group having 1 to 30 carbon atoms, an acyl group, an alkenyl group having 2 to 20 carbon atoms, an aryl group having 6 to 20 carbon atoms, and an aryloxy group, and optionally containing an ether group, an ester group, a carbonyl group, and a lactone ring. In the general formula (K-2), $R^{103}$ represents a hydrogen atom, a linear, a branched, or a cyclic alkyl group having 1 to 20 carbon atoms, an alkenyl group having 2 to 20 carbon atoms, an aryl group having 6 to 20 carbon atoms, optionally containing an ether group, an ester group, a carbonyl group, or a lactone ring.

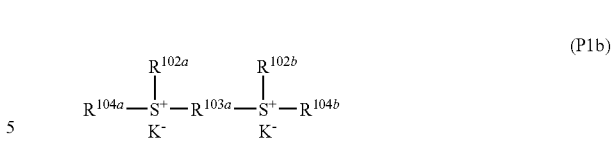

Wherein, each of $R^{102a}$ and $R^{102b}$ represents a linear, a branched, or a cyclic alkyl group having 1 to 8 carbon atoms; and $R^{103a}$ represents a linear, a branched, or a cyclic alkylene group having 1 to 10 carbon atoms. Each of $R^{104a}$ and $R^{104b}$ represents a 2-oxoalkyl group having 3 to 7 carbon atoms; and K⁻ represents a non-nucleophilic counter ion.

Specific examples of $R^{102a}$ and $R^{102b}$ include a methyl group, an ethyl group, a propyl group, an isopropyl group, a n-butyl group, a sec-butyl group, a tert-butyl group, a pentyl group, a hexyl group, a heptyl group, an octyl group, a cyclopentyl group, a cyclohexyl group, a cyclopropylmethyl group, a 4-methylcyclohexyl group, and a cyclohexylmethyl group. Specific examples of $R^{103a}$ include a methylene group, an ethylene group, a propylene group, a butylene group, a pentylene group, a hexylene group, a heptylene group, an octylene group, a nonylene group, a 1,4-cyclohexylene group, a 1,2-cyclohexylene group, a 1,3-cyclopentylene group, a 1,4-cyclooctylene group, and a 1,4-cyclohexanedimethylene group. Examples of $R^{104a}$ and $R^{104b}$ include a 2-oxopropyl group, a 2-oxocyclopentyl group, a 2-oxocyclohexyl group, and a 2-oxocycloheptyl group, and K⁻ may be exemplified by the same groups as those explained in the formulae (P1a-1) and (P1a-2).

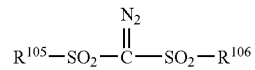

Wherein, each of $R^{105}$ and $R^{106}$ represents a linear, a branched, or a cyclic alkyl group or a halogenated alkyl group having 1 to 12 carbon atoms, an aryl group or a halogenated aryl group having 6 to 20 carbon atoms, or an aralkyl group having 7 to 12 carbon atoms.

Examples of the alkyl group as $R^{105}$ and $R^{106}$ include a methyl group, an ethyl group, a propyl group, an isopropyl group, a n-butyl group, a sec-butyl group, a tert-butyl group, a pentyl group, a hexyl group, a heptyl group, an octyl group, an amyl group, a cyclopentyl group, a cyclohexyl group, a cycloheptyl group, a norbornyl group, and an admantyl group. Examples of the halogenated alkyl group include a trifluoromethyl group, a 1,1,1-trifluoroethyl group, a 1,1,1-trichloroethyl group, and a nonafluorobutyl group. The aryl group may be exemplified by a phenyl group; an alkoxyphenyl group such as a p-methoxyphenyl group, a m-methoxyphenyl group, an o-methoxyphenyl group, an ethoxyphenyl group, a p-tert-butoxyphenyl group, and a m-tert-butoxyphenyl group; and an alkylphenyl group such as a 2-methylphenyl group, a 3-methylphenyl group, a 4-methylphenyl group, an ethylphenyl group, a 4-tert-butylphenyl group, a 4-butylphenyl group, a dimethylphenyl group; or others. The halogenated aryl group may be exemplified by a fluorophenyl group, a chlorophenyl group, a 1,2,3,4,5-pentafluorophenyl group, and the like. The aralkyl group may be exemplified by a benzyl group, a phenetyl group, and the like.

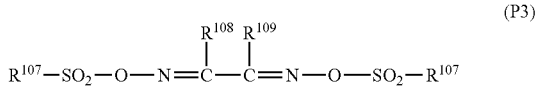

(P3)

Wherein, each of $R^{107}$, $R^{108}$, and $R^{109}$ represents a linear, a branched, or a cyclic alkyl group or a halogenated alkyl group having 1 to 12 carbon atoms, an aryl group or a halogenated aryl group having 6 to 20 carbon atoms, or an aralkyl group having 7 to 12 carbon atoms; $R^{108}$ and $R^{109}$ may form a ring structure by bonding with each other, and when a ring structure is formed; each of $R^{108}$ and $R^{109}$ represents a linear or a branched alkylene group having 1 to 6 carbon atoms.

The alkyl group, the halogenated alkyl group, an aryl group, a halogenated aryl group, and aralkyl group as $R^{107}$, $R^{108}$, and $R^{109}$ may be the same groups as those explained in $R^{105}$ and $R^{106}$. Here, the alkylene group as $R^{108}$ and $R^{109}$ may be exemplified by a methylene group, an ethylene group, a propylene group, a butylene group, a hexylene group, and the like.

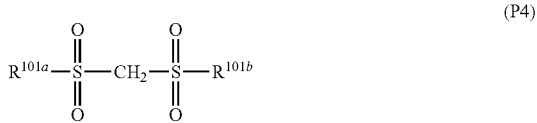

(P4)

Wherein, each of $R^{101a}$ and $R^{101b}$ represents the same meanings as before.

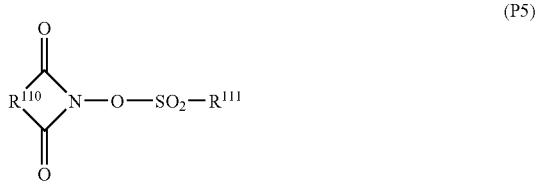

(P5)

Wherein, $R^{110}$ represents an arylene group having 6 to 10 carbon atoms, an alkylene group having 1 to 6 carbon atoms, or an alkenylene group having 2 to 6 carbon atoms, wherein a part or all of hydrogen atoms in these groups may be further substituted by a linear or a branched alkyl group or an alkoxy group having 1 to 4 carbon atoms, a nitro group, an acetyl group, or a phenyl group; and $R^{111}$ represents an alkyl group, an alkenyl group, or an alkoxyalkyl group, with a linear, a branched, or a cyclic structure having 1 to 8 carbon atoms, a phenyl group, or a naphthyl group, wherein a part of or all of hydrogen atoms in these groups may be substituted further by an alkyl group or an alkoxy group having 1 to 4 carbon atoms; a phenyl group optionally substituted by an alkyl group having 1 to 4 carbon atoms, an alkoxy group, a nitro group, or an acetyl group; a heteroaromatic group having 3 to 5 carbon atoms; a chlorine atom; or a fluorine atom.

Here, the arylene group as $R^{110}$ may be exemplified by a 1,2-phenylene group, a 1,8-naphthylene group, and the like. The alkylene group may be exemplified by a methylene group, an ethylene group, a trimethylene group, a tetramethylene group, a phenylethylene group, a norbornane-2,3-diyl group, and the like. The alkenylene group may be exemplified by a 1,2-vinylene group, a 1-phenyl-1,2-vinylene group, a 5-norbornene-2,3-diyl group, and the like. The alkyl group as $R^{111}$ represents the same meanings as $R^{101a}$ to $R^{101c}$. The alkenyl group may be exemplified by a vinyl group, a 1-propenyl group, an allyl group, a 1-buthenyl group, a 3-buthenyl group, an isoprenyl group, a 1-pentenyl group, a 3-pentenyl group, a 4-pentenyl group, a dimethylallyl group, a 1-hexenyl group, a 3-hexenyl group, a 5-hexenyl group, a 1-heptenyl group, a 3-heptenyl group, a 6-heptenyl group, a 7-octenyl group, and the like. The alkoxyalkyl group may be exemplified by a methoxymethyl group, an ethoxymethyl group, a propoxymethyl group, a butoxymethyl group, a pentyloxymethyl group, a hexyloxymethyl group, a heptyloxymethyl group, a methoxyethyl group, an ethoxyethyl group, a propoxyethyl group, a butoxyethyl group, a pentyloxyethyl group, a hexyloxyethyl group, a methoxypropyl group, an ethoxypropyl group, a propoxypropyl group, a butoxypropyl group, a methoxybutyl group, an ethoxybutyl group, a propoxybutyl group, a methoxypentyl group, an ethoxypentyl group, a methoxyhexyl group, a methoxyheptyl group, and the like.

Here, the alkyl group having 1 to 4 carbon atoms optionally substituted may be exemplified by a methyl group, an ethyl group, a propyl group, an isopropyl group, a n-butyl group, an isobutyl group, a tert-butyl group, and the like. The alkoxy group having 1 to 4 carbon atoms may be exemplified by a methoxy group, an ethoxy group, a propoxy group, an isopropoxy group, a n-butoxy group, an isobutoxy group, a tert-butoxy group, and the like. The phenyl group optionally substituted by an alkyl group having 1 to 4 carbon atoms, an alkoxy group, a nitro group, or an acetyl group may be exemplified by a phenyl group, a tollyl group, a p-tert-butoxyphenyl group, a p-acetylphenyl group, a p-nitrophenyl group, and the like. The heteroaromatic group having 3 to 5 carbon atoms may be exemplified by a pyridyl group, a furyl group, and the like.

The onium salt may be exemplified by diphenyliodonium trifluoromethanesulfonate, (p-tert-butoxyphenyl)phenyliodonium trifluoromethanesulfonate, diphenyliodonium p-toluenesulfonate, (p-tert-butoxyphenyl)phenyliodonium p-toluenesulfonate, triphenylsulfonium trifluoromethanesulfonate, (p-tert-butoxyphenyl)diphenylsulfonium trifluoromethanesulfonate, bis(p-tert-butoxyphenyl)phenylsulfonium trifluoromethanesulfonate, tris(p-tert-butoxyphenyl)sulfonium trifluoromethanesulfonate, triphenylsulfonium p-toluenesulfonate, (p-tert-butoxyphenyl)diphenylsulfonium p-toluenesulfonate, bis(p-tert-butoxyphenyl)phenylsulfonium p-toluenesulfonate, tris(p-tert-butoxyphenyl)sulfonium p-toluenesulfonate, triphenylsulfonium nonafluolobuthanesulfonate, triphenylsulfonium butanesulfonate, trimethylsulfonium trifluoromethanesulfonate, trimethylsulfonium p-toluenesulfonate, cyclohexylmethyl(2-oxocyclohexyl)sulfonium trifluoromethanesulfonate, cyclohexylmethyl(2-oxocyclohexyl)sulfonium p-toluenesulfonate, dimethylphenylsulfonium trifluoromethanesulfonate, dimethylphenylsulfonium p-toluenesulfonate, dicyclohexylphenylsulfonium trifluoromethanesulfonate, dicyclohexylphenylsulfonium p-toluenesulfonate, trinaphthylsulfonium trifluoromethanesulfonate, (2-norbonyl)methyl (2-oxocyclohexyl)sulfonium trifluoromethanesulfonate, ethylenebis[methyl(2-oxocyclopentyl)sulfonium trifluoromethanesulfonate], 1,2'-naphthylcarbonyl methyl tetrahydrothiophenium triflate, and the like.

The diazomethane derivative may be exemplified by bis (benzenesulfonyl)diazomethane, bis(p-toluenesulfonyl)diazomethane, bis(xylenesulfonyl)diazomethane, bis(cyclohexylsulfonyl)diazomethane, bis(cyclopentylsulfonyl) diazomethane, bis(n-butylsulfonyl)diazomethane, bis (isobutylsulfonyl)diazomethane, bis(sec-butylsulfonyl) diazomethane, bis(n-propylsulfonyl)diazomethane, bis (isopropylsulfonyl)diazomethane, bis(tert-butylsulfonyl)diazomethane, bis(n-amylsulfonyl)diazomethane, bis(isoamylsulfonyl)diazomethane, bis(sec-amylsulfonyl)diazomethane, bis(tert-amylsulfonyl)diazomethane, 1-cyclohexylsulfonyl-1-(tert-butylsulfonyl)diazomethane, 1-cyclohexylsulfonyl-1-(tert-amylsulfonyl)diazomethane, 1-tert-amylsulfonyl-1-(tert-butylsulfonyl)diazomethane, and the like.

The glyoxime derivative may be exemplified by bis-O-(p-toluenesulfonyl)-α-dimetyl glyoxime, bis-O-(p-toluenesulfonyl)-α-diphenyl glyoxime, bis-O-(p-toluenesulfonyl)-α-dicyclohexyl glyoxime, bis-O-(p-toluenesulfonyl)-2,3-pentanedione glyoxime, bis-O-(p-toluenesulfonyl)-2-methyl-3,4-pentanedione glyoxime, bis-O-(n-butanesulfonyl)-α-dimetyl glyoxime, bis-O-(n-butanesulfonyl)-α-diphenyl glyoxime, bis-O-(n-butanesulfonyl)-α-dicyclohexyl glyoxime, bis-O-(n-butanesulfonyl)-2,3-pentanedione glyoxime, bis-O-(n-butanesulfonyl)-2-methyl-3,4-pentanedione glyoxime, bis-O-(methanesulfonyl)-α-dimetyl glyoxime, bis-O-(trifluoromethanesulfonyl)-α-dimetyl glyoxime, bis-O-(1,1,1-trifluoroethanesulfonyl)-α-dimetyl glyoxime, bis-O-(tert-butanesulfonyl)-α-dimetyl glyoxime, bis-O-(perfluorooctanesulfonyl)-α-dimetyl glyoxime, bis-O-(cyclohexanesulfonyl)-α-dimetyl glyoxime, bis-O-(benzenesulfonyl)-α-dimetyl glyoxime, bis-O-(p-fluorobenzenesulfonyl)-α-dimetyl glyoxime, bis-O-(p-tert-butylbenzenesulfonyl)-α-dimetyl glyoxime, bis-O-(xylenesulfonyl)-α-dimetyl glyoxime, bis-O-(camphorsulfonyl)-α-dimetyl glyoxime, and the like.

The bissulfone derivative may be exemplified by bisnaphthyl sulfonyl methane, bistrifluoromethyl sulfonyl methane, bismethyl sulfonyl methane, bisethyl sulfonyl methane, bispropyl sulfonyl methane, bisisopropyl sulfonyl methane, bis-p-toluene sulfonyl methane, bisbenzene sulfonyl methane, and the like.

The β-keto sulfone derivative may be exemplified by 2-cyclohexylcarbonyl-2-(p-toluenesulfonyl)propane, 2-isopropylcarbonyl-2-(p-toluenesulfonyl)propane, and the like.

The disulfone derivative may be exemplified by a diphenyl disulfone derivative, a dicyclohexyl disulfone derivative, and the like.

The nitrobenzyl sulfonate derivative may be exemplified by 2,6-dinitrobenzyl p-toluene sulfonate, 2,4-dinitrobenzyl p-toluene sulfonate, and the like.

The sulfonate ester derivative may be exemplified by 1,2,3-tris(methanesulfonyloxy)benzene, 1,2,3-tris(trifluoromethanesulfonyloxy)benzene, 1,2,3-tris(p-toluenesulfonyloxy)benzene, and the like.

Further, the sulfonate ester derivative of an N-hydroxyimide compound may be exemplified by N-hydroxysuccinimide methanesulfonate ester, N-hydroxysuccinimide trifluoromethanesulfonate ester, N-hydroxysuccinimide ethanesulfonate ester, N-hydroxysuccinimide 1-propanesulfonate ester, N-hydroxysuccinimide 2-propanesulfonate ester, N-hydroxysuccinimide 1-pentanesulfonate ester, N-hydroxysuccinimide 1-octanesulfonate ester, N-hydroxysuccinimide p-toluenesulfonate ester, N-hydroxysuccinimide p-methoxybenzenesulfonate ester, N-hydroxysuccinimide 2-chloroethanesulfonate ester, N-hydroxysuccinimide benzenesulfonate ester, N-hydroxysuccinimide 2,4,6-trimethylbenzenesulfonate ester, N-hydroxysuccinimide 1-naphthalenesulfonate ester, N-hydroxysuccinimide 2-naphthalenesulfonate ester, N-hydroxy-2-phenylsuccinimide methanesulfonate ester, N-hydroxymaleimide methanesulfonate ester, N-hydroxymaleimide ethanesulfonate ester, N-hydroxy-2-phenylmaleimide methanesulfonate ester, N-hydroxyglutarimide methanesulfonate ester, N-hydroxyglutarimide benzenesulfonate ester, N-hydroxyphthalimide methanesulfonate ester, N-hydroxyphthalimide benzenesulfonate ester, N-hydroxyphthalimide trifluoromethanesulfonate ester, N-hydroxyphthalimide p-toluenesulfonate ester, N-hydroxynaphthalimide methanesulfonate ester, N-hydroxynaphthalimide benzenesulfonate ester, N-hydroxy-5-norbornene-2,3-dicarboxyimide methanesulfonate ester, N-hydroxy-5-norbornene-2,3-dicarboxyimide trifluoromethanesulfonate ester, N-hydroxy-5-norbornene-2,3-dicarboxyimide p-toluenesulfonate ester, and the like.

Especially, the onium salt such as triphenylsulfonium trifluoromethanesulfonate, (p-tert-butoxyphenyl)diphenylsulfonium trifluoromethanesulfonate, tris(p-tert-butoxyphenyl)sulfonium trifluoromethanesulfonate, triphenylsulfonium p-toluenesulfonate, (p-tert-butoxyphenyl)diphenylsulfonium p-toluenesulfonate, tris(p-tert-butoxyphenyl)sulfonium p-toluenesulfonate, trinaphthylsulfonium trifluoromethanesulfonate, cyclohexylmethyl(2-oxocyclohexyl)sulfonium trifluoromethanesulfonate, (2-norbonyl)methyl(2-oxocyclohexyl)sulfonium trifluoromethanesulfonate, and 1,2'-naphthylcarbonylmethyltetrahydrothiophenium triflate; the diazomethane derivative such as bis(benzenesulfonyl)diazomethane, bis(p-toluenesulfonyl)diazomethane, bis(cyclohexylsulfonyl)diazomethane, bis(n-butylsulfonyl)diazomethane, bis(isobutylsulfonyl)diazomethane, bis(sec-butylsulfonyl)diazomethane, bis(n-propylsulfonyl)diazomethane, bis(isopropylsulfonyl)diazomethane, and bis(tert-butylsulfonyl)diazomethane; the glyoxime derivative such as bis-O-(p-toluenesulfonyl)-α-dimetyl glyoxime and bis-O-(n-butanesulfonyl)-α-dimetyl glyoxime; the bissulfone derivative such as bisnaphthyl sulfonyl methane; the sulfonate ester derivatives of a N-hydroxyimide compound such as N-hydroxysuccinimide methanesulfonate ester, N-hydroxysuccinimide trifluoromethanesulfonate ester, N-hydroxysuccinimide 1-propanesulfonate ester, N-hydroxysuccinimide 2-propanesulfonate ester, N-hydroxysuccinimide 1-pentanesulfonate ester, N-hydroxysuccinimide p-toluenesulfonate ester, N-hydroxynaphthalimide methanesulfonate ester, and N-hydroxynaphthalimide benzenesulfonate ester are preferably used.

Further, an acid generator of the oxime type as shown by WO2004/074242 A2 may also be added.

Here, the acid generators as mentioned above may be used singly, or in a combination of two or more kinds. The onium salt is effective for improving a rectangular shape, and the diazomethane derivative and the glyoxime derivative are effective for reducing a standing wave, and thus a fine tuning of a profile may be possible by properly combining two of them.

The amount of the acid generator to be added is preferably 0.1 to 50 parts and more preferably 0.5 to 40 parts relative to 100 parts of the base resin. When the amount is 0.1 parts or more, a high sensitivity and a high degree of resolution may be possible since the amount of the acid generated by an exposure is sufficient, while when 50 parts or less, a transmittance of a resist is not decreased, thereby leading to a lower risk of deterioration of the degree of resolution, thus this range is preferable.

As the dissolution inhibitor to be added to the positive resist composition of the present invention, in particular to the chemically amplified positive resist composition, a compound whose weight-average molecular weight is 100 to 1,000, preferably 150 to 800, and in addition, whose hydrogen atoms of two or more phenolic hydroxy groups contained in the molecule are substituted by 0 to 100 mole % of the acid labile group in average as a whole or whose hydrogen atoms of carboxyl group contained in the molecule is substituted by 50 to 100 mole % of the acid labile group in average as a whole is preferable.

Here, the substitution rate of the hydrogen atom of the phenolic hydroxy group by the acid labile group is 0 mole % or more and preferably 30 mole % or more in average relative to total phenolic hydroxide groups, while the upper limit is 100 mole % and preferably 80 mole %. The substitution rate of the hydrogen atom of the carboxylic group by the acid labile group is 50 mole % or more and preferably 70 mole % or more in average relative to total carboxylic groups, while the upper limit may be 100 mole %.

Here, the compound having two or more of the phenolic hydroxide group or the compound having the carboxylic group is preferably a compound represented by the following formulae (D1) to (D14).

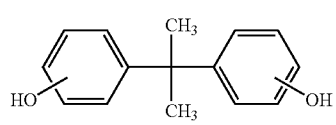
(D1)

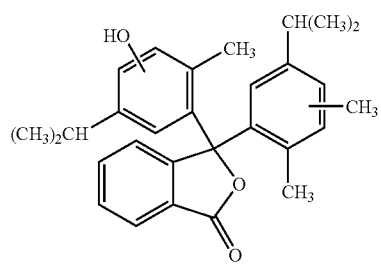
(D2)

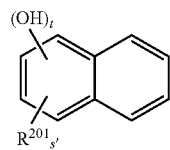
(D3)

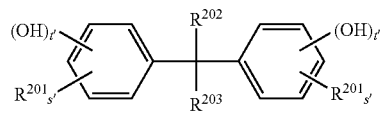
(D4)

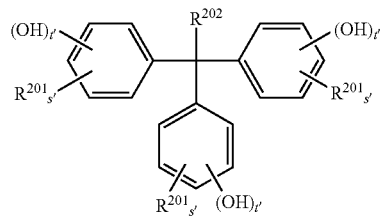
(D5)

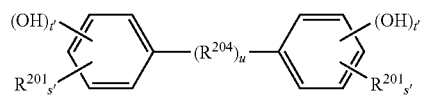
(D6)

-continued

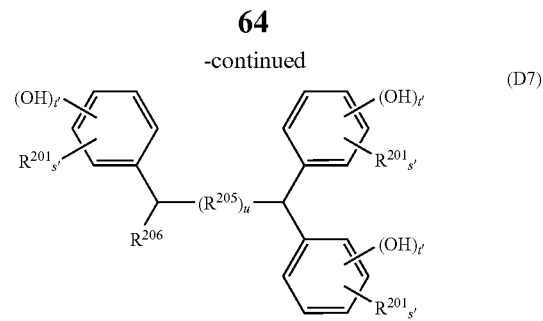
(D7)

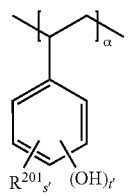
(D8)

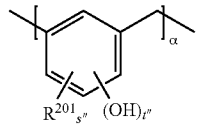
(D9)

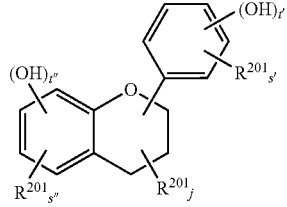
(D10)

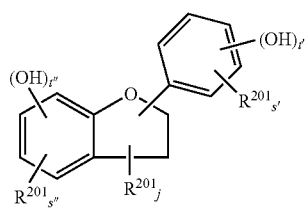
(D11)

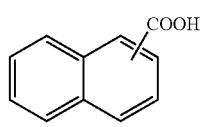
(D12)

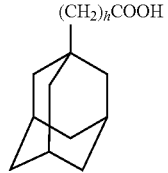
(D13)

(D14)

Here, each of $R^{201}$ and $R^{202}$ in the above formula represents a hydrogen atom, or an alkyl group or an alkenyl group, linear or branched, having 1 to 8 carbon atoms; $R^{203}$ represents a hydrogen atom, an alkyl group or an alkenyl group, linear or branched, having 1 to 8 carbon atoms, or a —$(R^{207})_h$COOH group; $R^{204}$ represents a —$(CH_2)_{i1}$— group (i1 represents 2 to 10), an arylene group having 6 to 10 carbon atoms, a carbonyl group, a sulfonyl group, an oxygen atom, or a sulfur atom; $R^{205}$ represents an alkylene group having 1 to 10 carbon atoms, an arylene group having 6 to 10 carbon atoms, a carbonyl group, a sulfonyl group, an oxygen atom, or a sulfur atom; R represents a hydrogen atom, a linear or a branched alkyl group or an alkenyl group having 1 to 8 carbon atoms, or a phenyl group or a naphthyl group each substituted by a hydroxy group; $R^{207}$ represents a linear or a branched alkylene group having 1 to 10 carbon atoms; and $R^{208}$ represents a hydrogen atom or a hydroxy group. Here, j represents an integer of 0 to 5; each of u and h represents 0 or 1; each of s, t, s', t', s", and t" satisfies the equations, s+t=8, s'+t'=5, s"+t"=4, and are the numbers giving at least one hydroxyl group to each phenyl skeleton; a represents a number giving the weight-average molecular weight of 100 to 1,000 to a compound represented by the formulae (D8) and (D9).

The amount of the dissolution inhibitor to be blended is 0 to 50 parts, preferably 5 to 50 parts, and further preferably 10 to 30 parts, relative to 100 parts of the base resin. It may be used singly, or in a mixture of two or more kinds. The amount of 0 part or more relative to 100 parts of the base resin may improve the degree of resolution, and the amount of 50 parts or less may prevent a decrease of the degree of resolution from occurring because of a lowered risk of film loss of the pattern, thus the above-mentioned range is preferable.

Further, the positive resist composition of the present invention may contain a basic compound. The basic compound is preferably the one, which can suppress a diffusion rate of the acid generated from the acid generator into a resist film. By blending the basic compound, the diffusion rate of the acid in the resist film may be suppressed, thereby leading to improving the degree of resolution, to suppressing a sensitivity change after exposure, to reducing a dependency on a substrate and an environment, and to improving an exposure allowance, a pattern profile, and the like.

The basic compound may be exemplified by a primary, a secondary, and a tertiary aliphatic amine, a mixed amine, an aromatic amine, a heterocyclic amine, a compound containing nitrogen which has a carboxy group, a compound containing nitrogen which has a sulfonyl group, a compound containing nitrogen which has a hydroxy group, a compound containing nitrogen which has a hydroxyphenyl group, an alcoholic compound containing nitrogen, an amide derivative, an imide derivative, and the like.

Specific examples of the primary aliphatic amine include ammonia, methylamine, ethylamine, n-propylamine, isopropylamine, n-butylamine, isobutylamine, sec-butylamine, tert-butylamine, pentylamine, tert-amylamine, cyclopentylamine, hexylamine, cyclohexylamine, heptylamine, octylamine, nonylamine, decylamine, dodecylamine, cetylamine, methylenediamine, ethylenediamine, and tetraethylenepentamine. Specific examples of the secondary aliphatic amine include dimethylamine, diethylamine, di-n-propylamine, diisopropylamine, di-n-butylamine, diisobutylamine, di-sec-butylamine, dipentylamine, dicyclopentylamine, dihexylamine, dicyclohexylamine, diheptylamine, dioctylamine, dinonylamine, didecylamine, didodecylamine, dicetylamine, N,N-dimethylmethylene diamine, N,N-dimethylethylene diamine, and N,N-dimethyltetraethylene pentamine. Specific examples of the tertiary aliphatic amine include trimethylamine, triethylamine, tri-n-propylamine, triisopropylamine, tri-n-butylamine, triisobutylamine, tri-sec-butylamine, tripentylamine, tricyclopentylamine, trihexylamine, tricyclohexylamine, triheptylamine, trioctylamine, trinonylamine, tridecylamine, tridodecylamine, tricetylamine, N,N,N',N'-tetramethylmethylene diamine, N,N,N',N'-tetramethylethylene diamine, and N,N,N',N'-tetramethyltetraethylene pentamine.

The mixed amine may be exemplified by dimethylethylamine, methylethylpropylamine, benzylamine, phenetylamine, benzyldimethylamine, and the like.

Specific examples of the aromatic amine and the heterocyclic amine include an aniline derivative (such as aniline, N-methylaniline, N-ethylaniline, N-propylaniline, N,N-dimethylaniline, 2-methylaniline, 3-methylaniline, 4-methylaniline, ethylaniline, propylaniline, trimethylaniline, 2-nitroaniline, 3-nitroaniline, 4-nitroaniline, 2,4-dinitroaniline, 2,6-dinitroaniline, 3,5-dinitroaniline, and N,N-dimethyltoluidine), diphenyl(p-tolyl)amine, methyldiphenylamine, triphenylamine, phenylenediamine, naphthylamine, diaminonaphthalene, a pyrrole derivative (such as pyrrole, 2H-pyrrole, 1-methylpyrrole, 2,4-dimethylpyrrole, 2,5-dimethylpyrrole, and N-methylpyrrole), a oxazole derivative (such as oxazole and isooxazole), a thiazole derivative (such as thiazole and isothiazole), an imidazole derivative (such as imidazole, 4-methylimidazole, and 4-methyl-2-phenylimidazole), a pyrazole derivative, a furazan derivative, a pyrroline derivative (such as pyrroline and 2-methyl-1-pyrroline), a pyrrolidine derivative (such as pyrrolidine, N-methylpyrrolidine, pyrrolidinone, and N-methylpyrrolidone), an imidazoline derivative, an imidazolidine derivative, a pyridine derivative (such as pyridine, methylpyridine, ethylpyridine, propylpyridine, butylpyridine, 4-(1-butylpentyl)pyridine, dimethylpyridine, trimethylpyridine, triethylpyridine, phenylpyridine, 3-methyl-2-phenylpyridine, 4-tert-butylpyridine, diphenylpyridine, benzylpyridine, methoxypyridine, butoxypyridine, dimethoxypyridine, 1-methyl-2-pyridine, 4-pyrrolidinopyridine, 1-methyl-4-phenylpyridine, 2-(1-ethylpropyl)pyridine, aminopyridine, and dimethylaminopyridine), a pyridazine derivative, a pyrimidine derivative, a pyrazine derivative, a pirazoline derivative, a pyrazolidine derivative, a piperidine derivative, a piperazine derivative, a morpholine derivative, an indole derivative, an isoindole derivative, a 1H-indazole derivative, an indoline derivative, a quinoline derivative (such as quinoline and 3-quinolinecarbonitrile), an isoquinoline derivative, a cinnoline derivative, a quinazoline derivative, a quinoxaline derivative, a phthalazine derivative, a purine derivative, a pteridine derivative, a carbazole derivative, a phenanthridine derivative, an acridine derivative, a phenazine derivative, a 1,10-phenanthroline derivative, an adenine derivative, an adenosine derivative, a guanine derivative, a quanosine derivative, an uracil derivative, and an uridine derivative.

Further, examples of the compound containing nitrogen which has a carboxy group include amino benzoic acid, indole carboxylic acid, and an amino acid derivative (such as nicotinic acid, alanine, arginine, aspartic acid, glutamic acid, glycine, histidine, isoleucine, glycyl leucine, leucine, methionine, phenylalanine, threonine, lysine, 3-aminopyrazine-2-carboxylic acid, and methoxy alanine). Examples of the compound containing nitrogen which has a sulfonyl group include 3-pyridinesulfonic acid and pyridinium p-toluenesulfonate. Examples of the compound containing nitrogen which has a hydroxy group, the compound containing nitrogen which has a hydroxyphenyl group, and the alcoholic compound containing nitrogen include 2-hydroxy pyridine, amino cresol, 2,4-quinoline diol, 3-indole methanol hydrate, monoethanol amine, diethanol amine, triethanol amine, N-ethyl diethanol amine, N,N-diethyl ethanol amine, triisopropanol amine, 2,2'-imino diethanol, 2-amino ethanol, 3-amino-1-propanol, 4-amino-1-butanol, 4-(2-hydroxyethyl)morpholine, 2-(2-hydroxyethyl)pyridine, 1-(2-hydroxyethyl)piperazine, 1-[2-(2-hydroxyethoxy)ethyl]piperazine, piperidine ethanol, 1-(2-hydroxyethyl)pyrrolidine, 1-(2-hydroxyethyl)-2-pyrrolidinone, 3-piperidino-1,2-propane diol, 3-pyrrolidino-1,2-propane diol, 8-hydroxyjulolidine, 3-quinuclidinol, 3-tropanol, 1-methyl-2-pyrrolidine ethanol, 1-aziridine ethanol, N-(2-hydroxyethyl)phthalimide, and N-(2-hydroxyethyl)isonicotine amide. Examples of the amide derivative include formamide, N-methyl formamide, N,N-dimethyl formamide, acetamide, N-methyl acetamide, N,N-dimethyl acetamide, propione amide, and benzamide. Examples of the imide derivative include phthalimide, succine imide, and maleimide.

Further, a compound selected from the basic compounds represented by the following general formula (B)-1 may be added singly, or in a combination of two or more kinds:

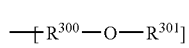
(B)-1 wherein, n1 represents 1, 2, and 3. The side-chain X' may be the same or different, and represented by the following general formulae (X)-1 to (X)-3. The side chain Y' may be the same or different, representing a hydrogen atom, a linear, a branched, or a cyclic alkyl group having 1 to 20 carbon atoms, and optionally containing an ether group or a hydroxy group. Further, X' may form a ring by connecting with each other.

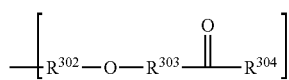

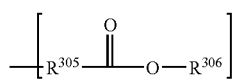

Here, each of $R^{300}$, $R^{302}$, and $R^{305}$ independently represents any of a linear or a branched alkylene group having 1 to 4 carbon atoms. Each of $R^{301}$ and $R^{304}$ independently represents any of a hydrogen atom, or a linear, a branched or a cyclic alkyl group having 1 to 20 carbon atoms, and optionally containing one or plural kinds selected from a hydroxy group, an ether group, an ester group, and a lactone ring; $R^{303}$ represents any of a single bond, or a linear or a branched alkylene group having 1 to 4 carbon atoms; and $R^{306}$ represents any of a linear, a branched, or a cyclic alkyl group having 1 to 20 carbon atoms, and optionally containing one or plural kinds selected from a hydroxy group, an ether group, an ester group, and a lactone ring.

Specific examples of the compound represented by the general formula (B)-1 include tris(2-methoxymethoxyethyl)amine, tris[2-(2-methoxyethoxy)ethyl]amine, tris[2-(2-methoxyethoxymethoxy)ethyl]amine, tris[2-(1-methoxyethoxy)ethyl]amine, tris[2-(1-ethoxyethoxy)ethyl]amine, tris[2-(1-ethoxypropoxy)ethyl]amine, tris{2-[2-(2-hydroxyethoxy)ethoxy]ethyl}amine, 4,7,13,16,21,24-hexaoxa-1,10-diazabicyclo[8.8.8]hexacosane, 4,7,13,18-tetraoxa-1,10-diazabicyclo[8.5.5]eicosane, 1,4,10,13-tetraoxa-7,16-diazabicyclooctadecane, 1-aza-12-crown-4,1-aza-15-crown-5,1-aza-18-crown-6, tris(2-formyloxyethyl)amine, tris(2-acetoxyethyl)amine, tris(2-propionyloxyethyl)amine, tris(2-butyryloxyethyl)amine, tris(2-isobutyryloxyethyl)amine, tris (2-valeryloxyethyl)amine, tris(2-pivaloyloxyethyl)amine, N,N-bis(2-acetoxyethyl) 2-(acetoxyacetoxy)ethyl amine, tris (2-methoxycarbonyloxyethyl)amine, tris(2-tert-butoxycarbonyloxyethyl)amine, tris[2-(2-oxopropoxy)ethyl]amine, tris[2-(methoxycarbonylmethyl)oxyethyl]amine, tris[2-(tert-butoxycarbonylmethyloxy)ethyl]amine, tris[2-(cyclohexyloxycarbonylmethyloxy)ethyl]amine, tris(2-methoxycarbonylethyl)amine, tris(2-ethoxycarbonylethyl)amine, N,N-bis (2-hydroxyethyl) 2-(methoxycarbonyl)ethyl amine, N,N-bis (2-acetoxyethyl) 2-(methoxycarbonyl)ethyl amine, N,N-bis (2-hydroxyethyl) 2-(ethoxycarbonyl)ethyl amine, N,N-bis (2-acetoxyethyl) 2-(ethoxycarbonyl)ethyl amine, N,N-bis(2-hydroxyethyl) 2-(2-methoxyethoxycarbonyl)ethyl amine, N,N-bis(2-acetoxyethyl) 2-(2-methoxyethoxycarbonyl)ethyl amine, N,N-bis(2-hydroxyethyl) 2-(2-hydroxyethoxycarbonyl)ethyl amine, N,N-bis(2-acetoxyethyl) 2-(2-acetoxyethoxycarbonyl)ethyl amine, N,N-bis(2-hydroxyethyl) 2-[(methoxycarbonyl)methoxycarbonyl]ethyl amine, N,N-bis(2-acetoxyethyl) 2-[(methoxycarbonyl)methoxycarbonyl]ethyl amine, N,N-bis(2-hydroxyethyl) 2-(2-oxopropoxycarbonyl)ethyl amine, N,N-bis(2-acetoxyethyl) 2-(2-oxopropoxycarbonyl)ethyl amine, N,N-bis(2-hydroxyethyl) 2-(tetrahydrofurfuryloxycarbonyl)ethyl amine, N,N-bis(2-acetoxyethyl) 2-(tetrahydrofurfuryloxycarbonyl)ethyl amine, N,N-bis(2-hydroxyethyl) 2-[(2-oxotetrahydrofurane-3-yl)oxycarbonyl]ethyl amine, N,N-bis(2-acetoxyethyl) 2-[(2-oxotetrahydrofurane-3-yl)oxycarbonyl]ethyl amine, N,N-bis(2-hydroxyethyl) 2-(4-hydroxybutoxycarbonyl) ethyl amine, N,N-bis(2-formyloxyethyl) 2-(4-formyloxybutoxycarbonyl)ethyl amine, N,N-bis(2-formyloxyethyl) 2-(2-formyloxyethoxycarbonyl)ethyl amine, N,N-bis(2-methoxyethyl) 2-(methoxycarbonyl)ethyl amine, N-(2-hydroxyethyl)bis[2-(methoxycarbonyl)ethyl]amine, N-(2-acetoxyethyl)bis[2-(methoxycarbonyl)ethyl]amine, N-(2-hydroxyethyl)bis[2-(ethoxycarbonyl)ethyl]amine, N-(2-acetoxyethyl)bis[2-(ethoxycarbonyl)ethyl]amine, N-(3-hydroxy-1-propyl)bis[2-(methoxycarbonyl)ethyl]amine, N-(3-acetoxy-1-propyl)bis[2-(methoxycarbonyl)ethyl] amine, N-(2-methoxyethyl)bis[2-(methoxycarbonyl)ethyl] amine, N-butyl bis[2-(methoxycarbonyl)ethyl]amine, N-butyl bis[2-(2-methoxyethoxycarbonyl)ethyl]amine, N-methyl bis(2-acetoxyethyl)amine, N-ethyl bis(2-acetoxyethyl) amine, N-methyl bis(2-pivaloyloxyethyl)amine, N-ethyl bis [2-(methoxycarbonyloxy)ethyl]amine, N-ethyl bis[2-(tert-butoxycarbonyloxy)ethyl]amine, tris (methoxycarbonylmethyl)amine, tris (ethoxycarbonylmethyl)amine, N-butyl bis (methoxycarbonylmethyl)amine, N-hexyl bis (methoxycarbonylmethyl)amine, and β-(diethylamino)-δ-valerolactone, but the compound is not restricted to them.

Further, a basic compound having a ring structure represented by the following general formula (B)-2 may also be added singly, or in a combination of two or more kinds.

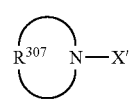
(B)-2

Wherein, X' represents the same meanings as before; $R^{307}$ represents a linear or a branched alkylene group having 2 to 20 carbon atoms, and may contain one or plural kinds selected from a carbonyl group, an ether group, an ester group, and a sulfide group.

Specific examples of the basic compound having a cyclic structure represented by the general formula (B)-2 include 1-[2-(methoxymethoxy)ethyl]pyrrolidine, 1-[2-(methoxymethoxy)ethyl]piperidine, 4-[2-(methoxymethoxy)ethyl]morpholine, 1-{2-[(2-methoxyethoxy)methoxy]ethyl}pyrrolidine, 1-{2-[(2-methoxyethoxy)methoxy]ethyl}piperidine, 4-{2-[(2-methoxyethoxy)methoxy]ethyl}morpholine, 2-(1-pyrrolidinyl)ethyl acetate, 2-piperidinoethyl acetate, 2-morpholinoethyl acetate, 2-(1-pyrrolidinyl)ethyl formate, 2-piperidinoethyl propionate, 2-morpholinoethyl acetoxyacetate, 2-(1-pyrrolidinyl)ethyl methoxyacetate, 4-[2-(methoxycarbonyloxy)ethyl]morpholine, 1-[2-(t-butoxycarbonyloxy)ethyl]piperidine, 4-[2-(2-methoxyethoxycarbonyloxy)ethyl]morpholine, methyl 3-(1-pyrrolidinyl)propionate, methyl 3-piperidinopropionate, methyl 3-morpholinopropionate, methyl 3-(thiomorpholino)propionate, methyl 2-methyl-3-(1-pyrrolidinyl)propionate, ethyl 3-morpholinopropionate, methoxycarbonylmethyl 3-piperidinopropionate, 2-hydroxyethyl 3-(1-pyrrolidinyl)propionate, 2-acetoxyethyl 3-morpholinopropionate, 2-oxotetrahydrofurane-3-yl 3-(1-pyrrolidinyl)propionate, tetrahydrofurfuryl 3-morpholinopropionate, glycidyl 3-piperidinopropionate, 2-methoxyethyl 3-morpholinopropionate, 2-(2-methoxyethoxy)ethyl 3-(1-pyrrolidinyl)propionate, butyl 3-morpholinopropionate, cyclohexyl 3-piperidinopropionate, α-(1-pyrrolidinyl)methyl-γ-butyrolactone, β-piperidino-γ-butyrolactone, β-morpholino-δ-valerolactone, methyl 1-pyrrolidinylacetate, methyl piperidinoacetate, methyl morpholinoacetate, methyl thiomorpholinoacetate, ethyl 1-pyrrolidinylacetate, and 2-methoxyethyl morpholinoacetate.

Further, a basic compound containing a cyano group represented by the following general formulae (B)-3 to may be added.

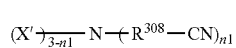  (B)-3

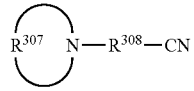  (B)-4

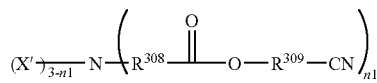  (B)-5

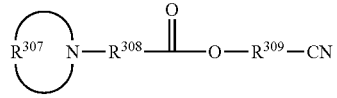  (B)-6

Wherein, X', $R^{307}$, and n1 represent the same meanings as before; $R^{308}$ and $R^{309}$ represent the same or different linear or branched alkylene group having 1 to 4 carbon atoms.

Specific examples of the basic compound containing a cyano group include 3-(diethylamino)propiononitrile, N,N-bis(2-hydroxyethyl)-3-amino propiononitrile, N,N-bis(2-acetoxyethyl)-3-amino propiononitrile, N,N-bis(2-formyloxyethyl)-3-amino propiononitrile, N,N-bis(2-methoxyethyl)-3-amino propiononitrile, N,N-bis[2-(methoxymethoxy)ethyl]-3-amino propiononitrile, methyl N-(2-cyanoethyl)-N-(2-methoxyethyl)-3-amino propionate, methyl N-(2-cyanoethyl)-N-(2-hydroxyethyl)-3-amino propionate, methyl N-(2-acetoxyethyl)-N-(2-cyanoethyl)-3-amino propionate, N-(2-cyanoethyl)-N-ethyl-3-amino propiononitrile, N-(2-cyanoethyl)-N-(2-hydroxyethyl)-3-amino propiononitrile, N-(2-acetoxyethyl)-N-(2-cyanoethyl)-3-amino propiononitrile, N-(2-cyanoethyl)-N-(2-formyloxyethyl)-3-amino propiononitrile, N-(2-cyanoethyl)-N-(2-methoxyethyl)-3-amino propiononitrile, N-(2-cyanoethyl)-N-[2-(methoxymethoxy)ethyl]-3-amino propiononitrile, N-(2-cyanoethyl)-N-(3-hydroxy-1-propyl)-3-amino propiononitrile, N-(3-acetoxy-1-propyl)-N-(2-cyanoethyl)-3-amino propiononitrile, N-(2-cyanoethyl)-N-(3-formyloxy-1-propyl)-3-amino propiononitrile, N-(2-cyanoethyl)-N-tetrahydrofurfuryl-3-amino propiononitrile, N,N-bis(2-cyanoethyl)-3-amino propiononitrile, diethylamino acetonitrile, N,N-bis(2-hydroxyethyl)amino acetonitrile, N,N-bis(2-acetoxyethyl) amino acetonitrile, N,N-bis(2-formyloxyethyl)amino acetonitrile, N,N-bis(2-methoxyethyl)amino acetonitrile, N,N-bis[2-(methoxymethoxy)ethyl]amino acetonitrile, methyl N-cyanomethyl-N-(2-methoxyethyl)-3-amino propionate, methyl N-cyanomethyl-N-(2-hydroxyethyl)-3-amino propionate, methyl N-(2-acetoxyethyl)-N-cyanomethyl-3-amino propionate, N-cyanomethyl-N-(2-hydroxyethyl)amino acetonitrile, N-(2-acetoxyethyl)-N-(cyanomethyl)amino acetonitrile, N-cyanomethyl-N-(2-formyloxyethyl)amino acetonitrile, N-cyanomethyl-N-(2-methoxyethyl)amino acetonitrile, N-cyanomethyl-N-[2-(methoxymethoxy)ethyl]amino acetonitrile, N-(cyanomethyl)-N-(3-hydroxy-1-propyl)amino acetonitrile, N-(3-acetoxy-1-propyl)-N-(cyanomethyl)amino acetonitrile, N-cyanomethyl-N-(3-formyloxy-1-propyl)amino acetonitrile, N,N-bis(cyanomethyl)aminoacetonitrile, 1-pyrrolidine propiononitrile, 1-piperidine propiononitrile, 4-morpholine propiononitrile, 1-pyrrolidine acetonitrile, 1-piperidine acetonitrile, 4-morpholine acetonitrile, cyanomethyl 3-diethylamino propionate, cyanomethyl N,N-bis(2-hydroxyethyl)-3-amino propionate, cyanomethyl N,N-bis(2-acetoxyethyl)-3-amino propionate, cyanomethyl N,N-bis(2-formyloxyethyl)-3-amino propionate, cyanomethyl N,N-bis(2-methoxyethyl)-3-amino propionate, cyanomethyl N,N-bis[2-(methoxymethoxy)ethyl)]-3-amino propionate, 2-cyanoethyl 3-diethylamino propionate, 2-cyanoethyl N,N-bis(2-hydroxyethyl)-3-amino propionate, 2-cyanoethyl N,N-bis(2-acetoxyethyl)-3-amino propionate, 2-cyanoethyl N,N-bis(2-formyloxyethyl)-3-amino propionate, 2-cyanoethyl N,N-bis(2-methoxyethyl)-3-amino propionate, 2-cyanoethyl N,N-bis[2-(methoxymethoxy)ethyl)]-3-amino propionate, cyanomethyl 1-pyrrolidine propionate, cyanomethyl 1-piperidine propionate, cyanomethyl 4-morpholine propionate, 2-cyanoethyl 1-pyrrolidine propionate, 2-cyanoethyl 1-piperidine propionate, and 2-cyanoethyl 4-morpholine propionate.

Here, the amount of the basic compound of the present invention to be blended is preferably 0.001 to 2 parts, in particular 0.01 to 1 part, relative to 100 parts of the base resin. When the amount is 0.001 parts or more, the blending effect is excellent, and when the amount is 2 parts or less, a risk of lowering the degree of resolution is decreased, thus it is preferable.

As a compound having a =C—COOH group in its molecule which may be added to the positive resist of the present invention, there may be mentioned one kind, or two or more kinds of the compounds, selected from the following groups I and II, but it is not limited to them. By blending this component, the PED stability of the resist is increased, thus an edge roughness on a nitride film substrate is improved.

[Group I]

Compounds represented by the following general formulae (A1) to (A10), a part of or all of whose hydrogen atom of a phenolic hydroxy group is substituted by a —$R^{401}$—COOH group ($R^{401}$ represents a linear or a branched alkylene group having 1 to 10 carbon atoms), and the mole ratio of whose phenolic hydroxy group (C) and =C—COOH group (D), namely (C/(C+D)) is 0.1 to 1.0.

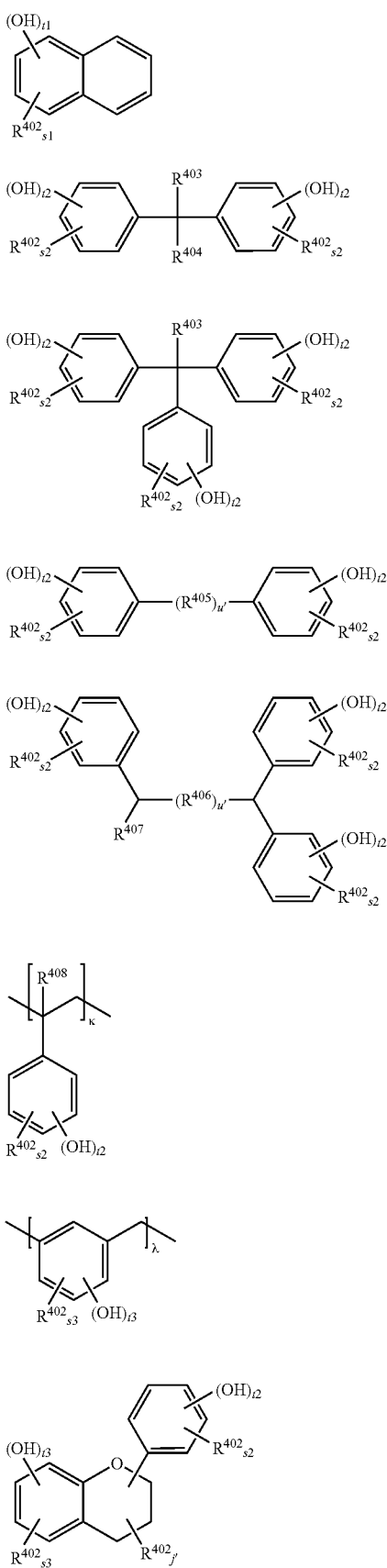

(A1)

(A2)

(A3)

(A4)

(A5)

(A6)

(A7)

(A8)

(A9)

(A10)

Wherein, $R^{408}$ represents a hydrogen atom or a methyl group. Each of $R^{402}$ and $R^{403}$ represents a hydrogen atom, a linear or a branched alkyl group or alkenyl group having 1 to 8 carbon atoms; $R^{404}$ represents a hydrogen atom, a linear or a branched alkyl group or alkenyl group having 1 to 8 carbon atoms, or a group represented by —$(R^{409})_{h''}$—COOR' (R' represents a hydrogen atom or a group represented by —$R^{409}$—COOH) ; $R^{405}$ represents a group represented by —$(CH_2)_{i''}$— (i" represents 2 to 10), an arylene group having 6 to 10 carbon atoms, a carbonyl group, a sulfonyl group, an oxygen atom, or a sulfur atom; $R^{406}$ represents an alkylene group having 1 to 10 carbon atoms, an arylene group having 6 to 10 carbon atoms, a carbonyl group, a sulfonyl group, an oxygen atom, or a sulfur atom; $R^{407}$ represents a hydrogen atom, a linear or a branched alkyl group having 1 to 8 carbon atoms, an alkenyl group, or a phenyl group or a naphthyl group each substituted by a hydroxy group; $R^{409}$ represents an alkylene or an alkenylene group, linear or branched, having 1 to 10 carbon atoms, or a —$R^{411}$—COOH group; $R^{410}$ represents a hydrogen atom, an alkyl group or an alkenyl group, linear or branched, having 1 to 8 carbon atoms, or a —$R^{411}$—COOH group; and $R^{411}$ represents a linear or a branched alkylene group having 1 to 10 carbon atoms. Here, j' represents 0 to 3; each of u' and h" represents 0 or 1; each of s1 to s4 and t1 to t4 satisfies the equations s1+t1=8, s2+t2=5, s3+t3=4, s4+t4=6, and are the numbers giving at least one hydroxy group in each phenyl skeletons; K represents a number giving the weight-average molecular weight of 1,000 to 5,000 to a compound represented by the formula (A6); λ represents a number giving the weight-average molecular weight of 1,000 to 10,000 to a compound represented by the formula (A7).

[Group II]

Compounds represented by the following general formulae (A11) to (A15).

(A11)

(A12)

-continued

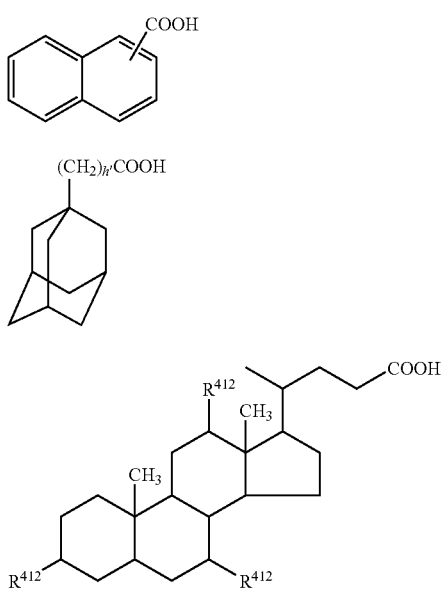

(A13)

(A14)

(A15)

Wherein, $R^{402}$, $R^{403}$, and $R^{411}$ represent the same meanings as before; and $R^{412}$ represents a hydrogen atom or a hydroxy group. Here, s5 and t5 are the numbers satisfying equations $s5 \geqq 0$, $t5 \geqq 0$, and $s5+t5=5$, and h' represents 0 or 1.

Specific examples of the components represented by the general formulae (A1) to (A15) include the compounds represented by the following general formulae (AI-1) to (AI-14) and (AII-1) to (AII-10), but the components are not restricted to them.

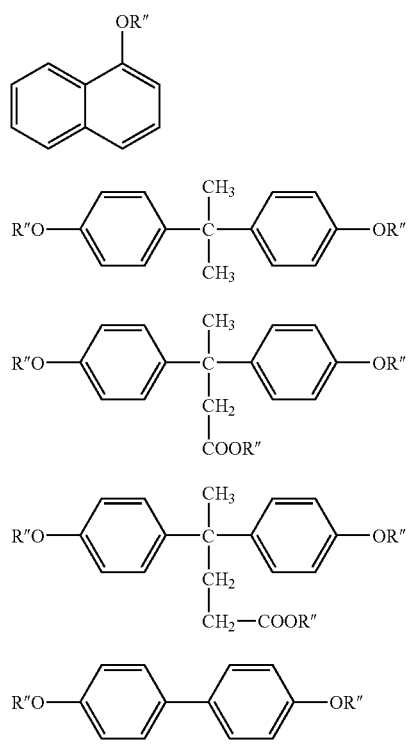

(AI-1)

(AI-2)

(AI-3)

(AI-4)

(AI-5)

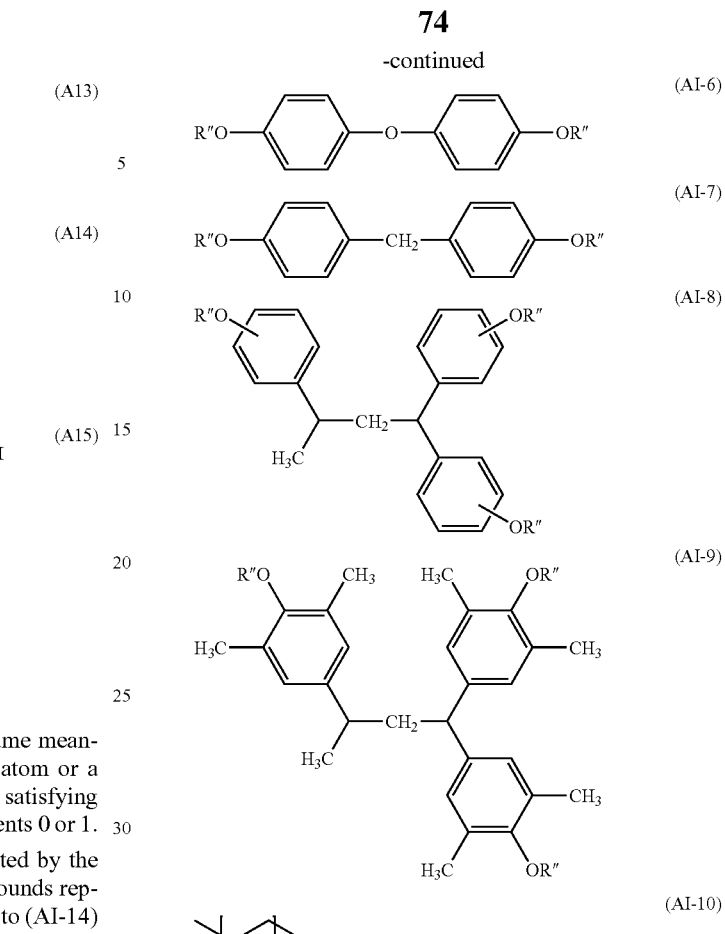

(AI-6)

(AI-7)

(AI-8)

(AI-9)

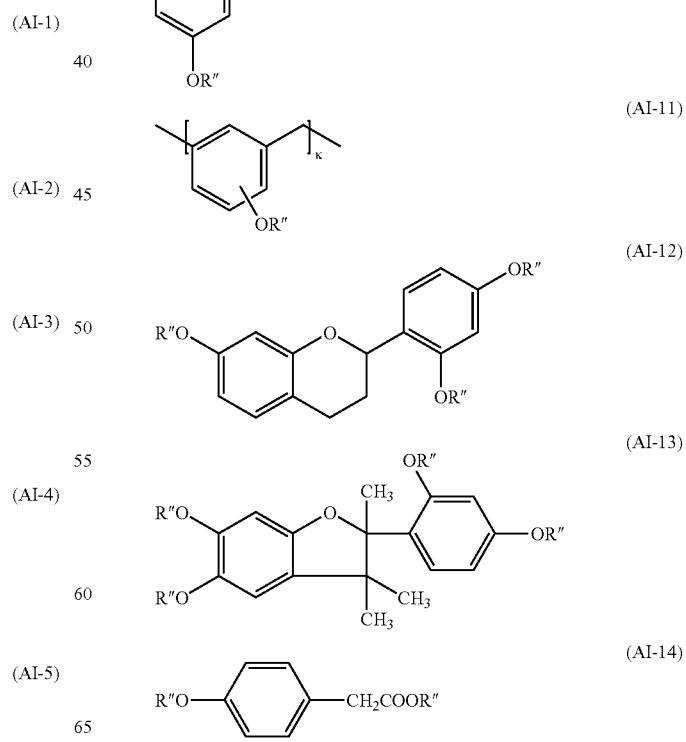

(AI-10)

(AI-11)

(AI-12)

(AI-13)

(AI-14)

Wherein, R" represents a hydrogen atom or a CH₂COOH group, wherein 10 to 100 mole % of R" in each compound is a CH₂COOH group. Here, α and κ represent the same meanings as before.

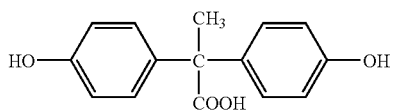
(AII-1)

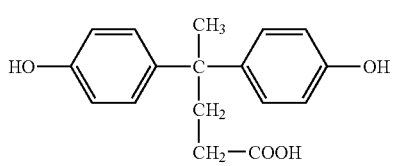
(AII-2)

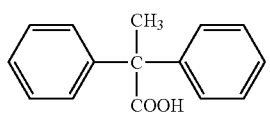
(AII-3)

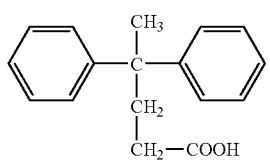
(AII-4)

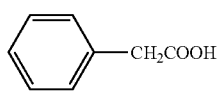
(AII-5)

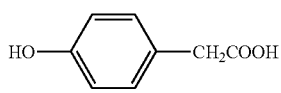
(AII-6)

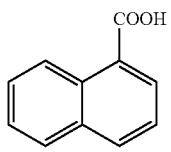
(AII-7)

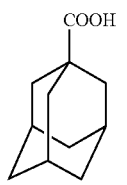
(AII-8)

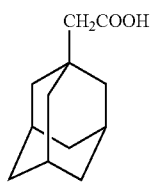
(AII-9)

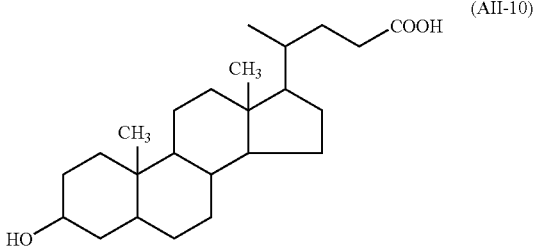
(AII-10)

Here, the compound having a =C—COOH group in its molecule may be used singly, or in a combination of two or more kinds.

The amount of the compound having a □C—COOH group in its molecule to be added is 0 to 5 parts, preferably 0.1 to 5 parts, further preferably 0.1 to 3 parts, and further more preferably 0.1 to 2 parts, relative to 100 parts of the base resin. This range is preferable because a risk of deterioration of the degree of resolution of the resist composition is low.

Further, the positive resist composition of the present invention may contain a dissolution controlling material comprising a compound having plural bisphenol groups substituted by the acid labile group represented by the following general formula BP-(1).

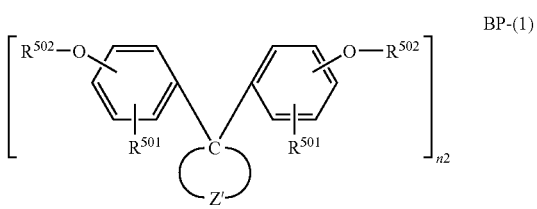
BP-(1)

Wherein, $R^{501}$ represents the same or different hydrogen atom, a linear, a branched, or a cyclic alkyl group having 1 to 10 carbon atoms, an aryl group having 6 to 10 carbon atoms, an alkenyl group having 2 to 10 carbon atoms, or a halogen atom; $R^{502}$ independently represents the same or different hydrogen atom or acid labile group; n2 represents an integer of 2 to 4; and Z' represents an alkyl group having a cyclic structure having total 5 to 40 carbon atoms in the formula, a cyclic hydrocarbon group having a bridge structure, or a condensed polycyclic hydrocarbon group, and optionally containing a hetero atom such as sulfur.

The acid labile group shown in the general formula BP-(1) may be used by selecting from those described above. The compound represented by the general formula BP-(1) may be specifically exemplified by the followings.

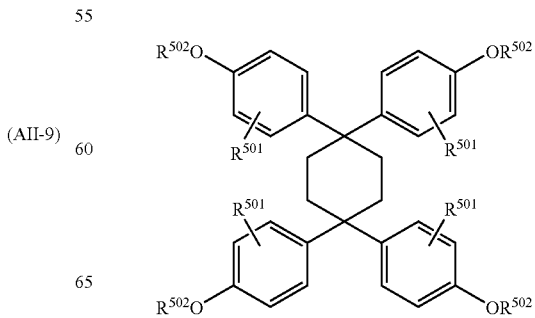

-continued
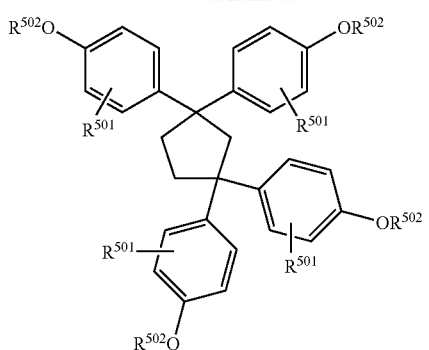
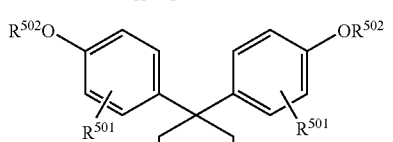
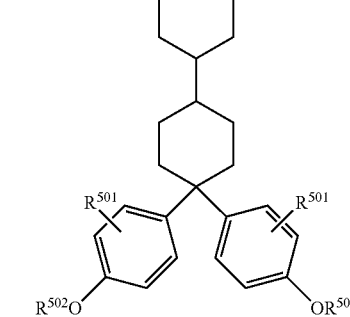
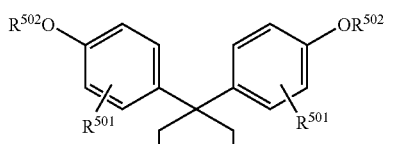
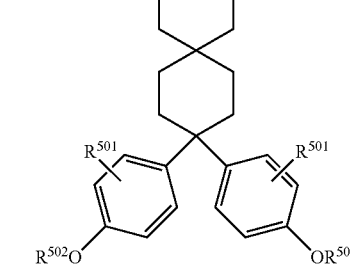
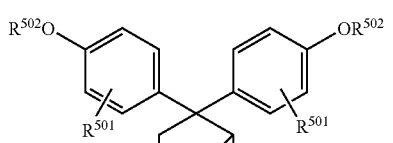
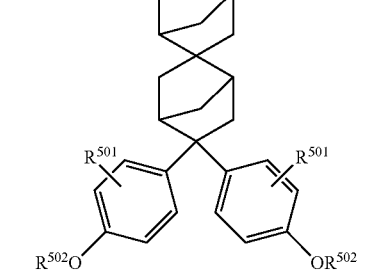
-continued
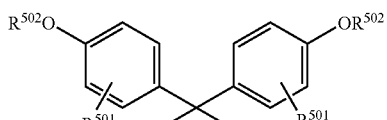
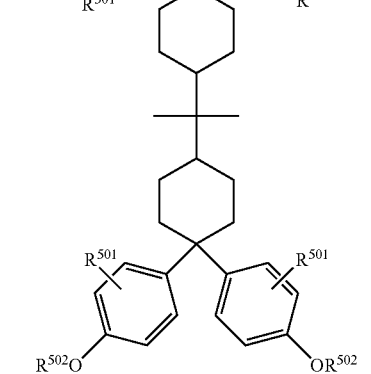
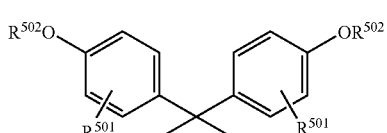
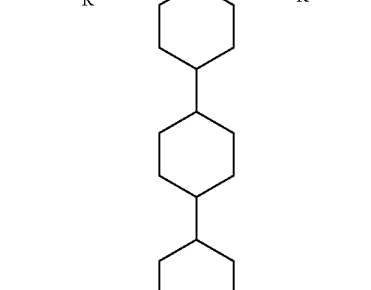
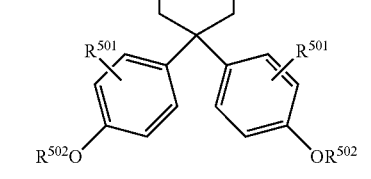
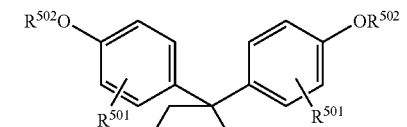
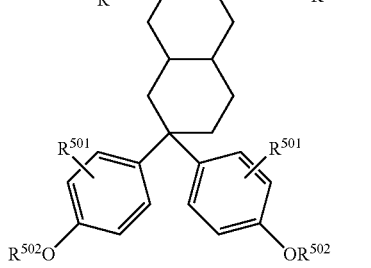

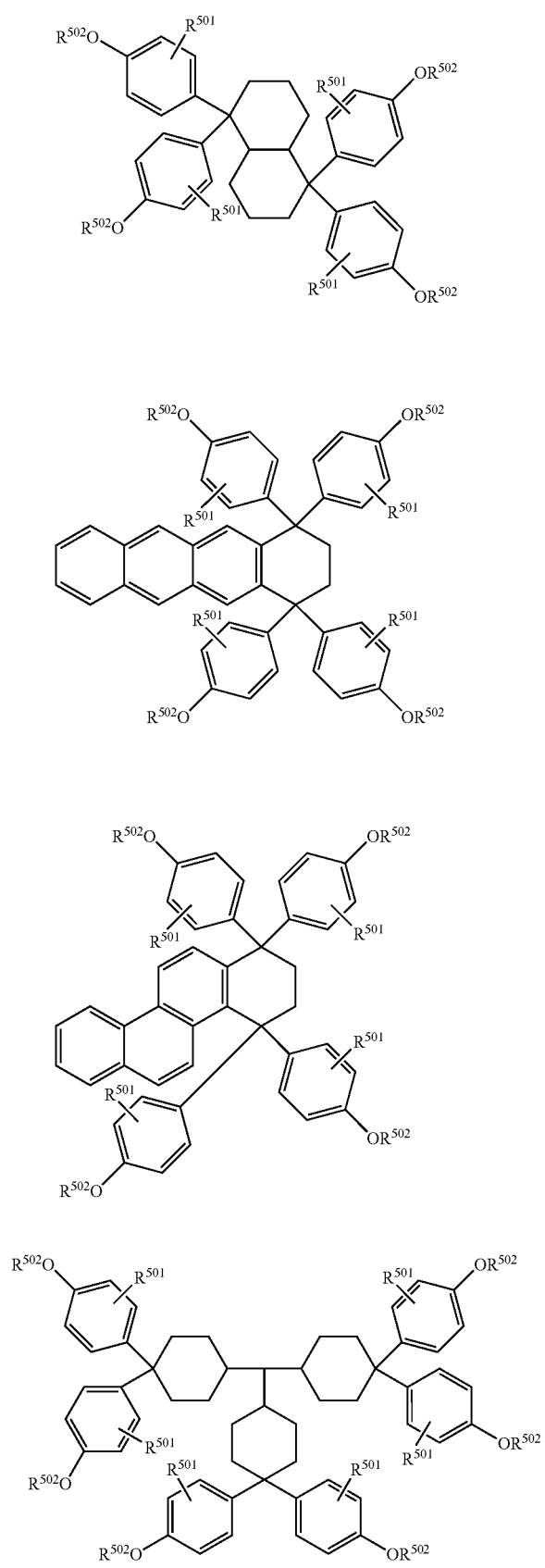
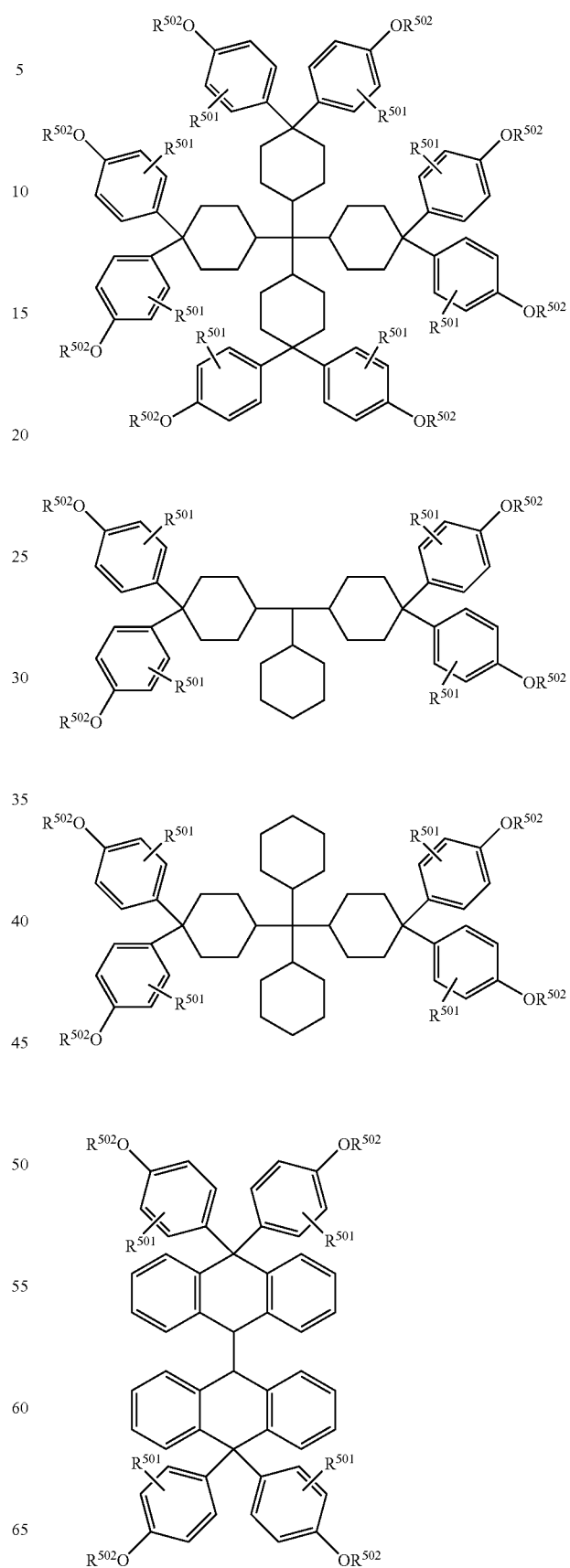

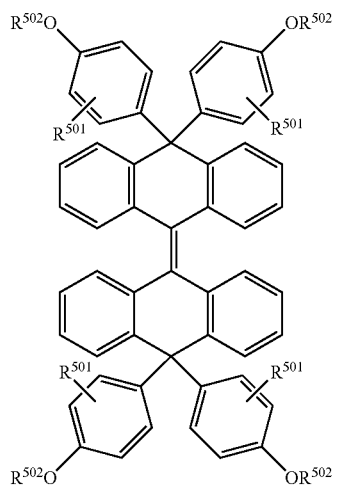
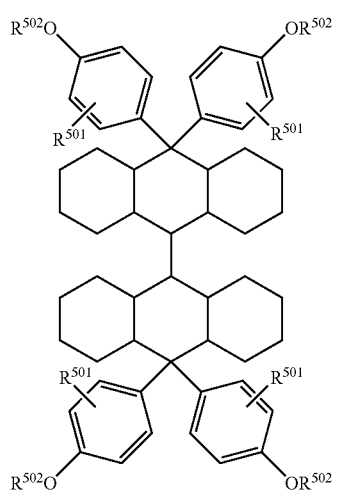
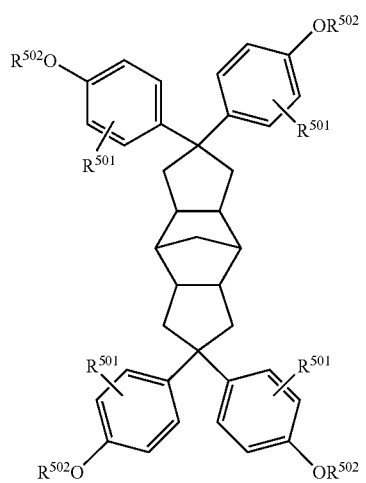
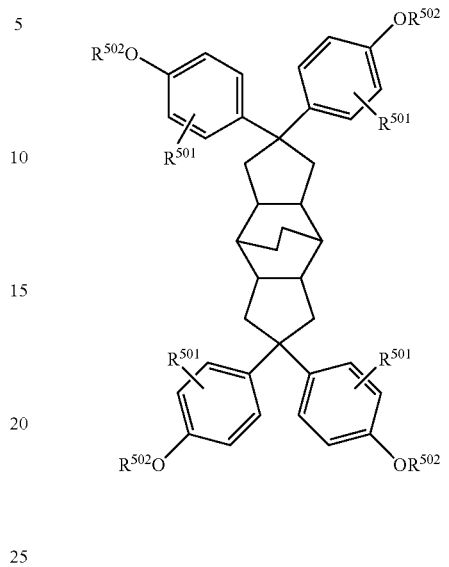
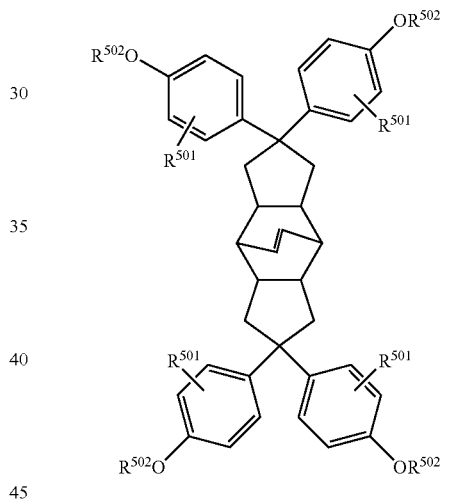
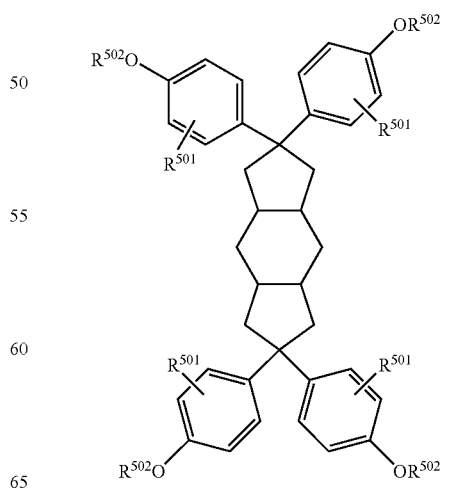

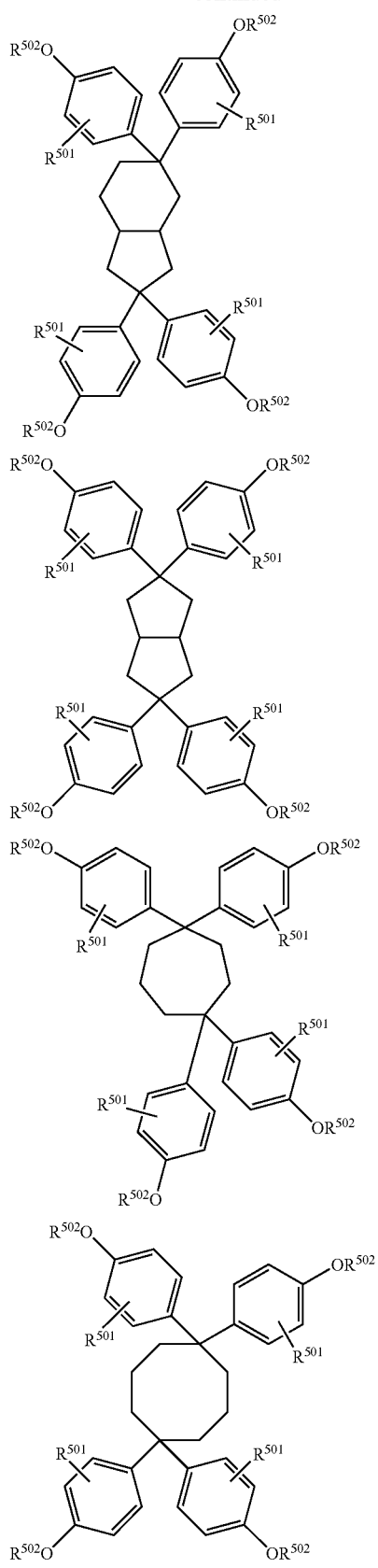
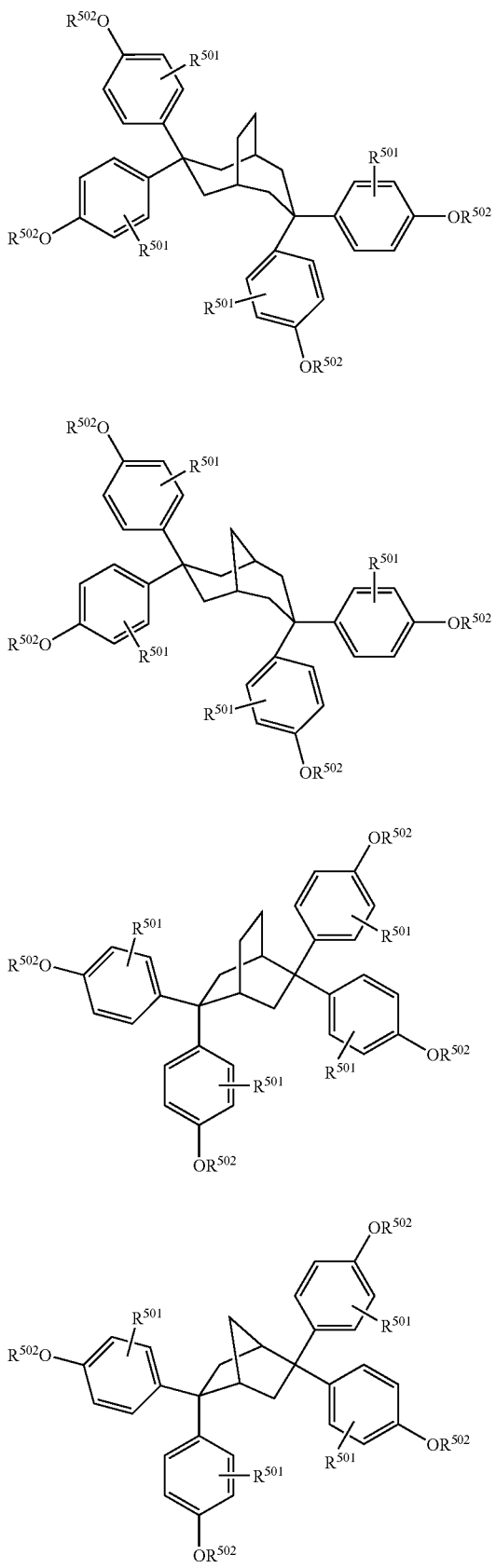

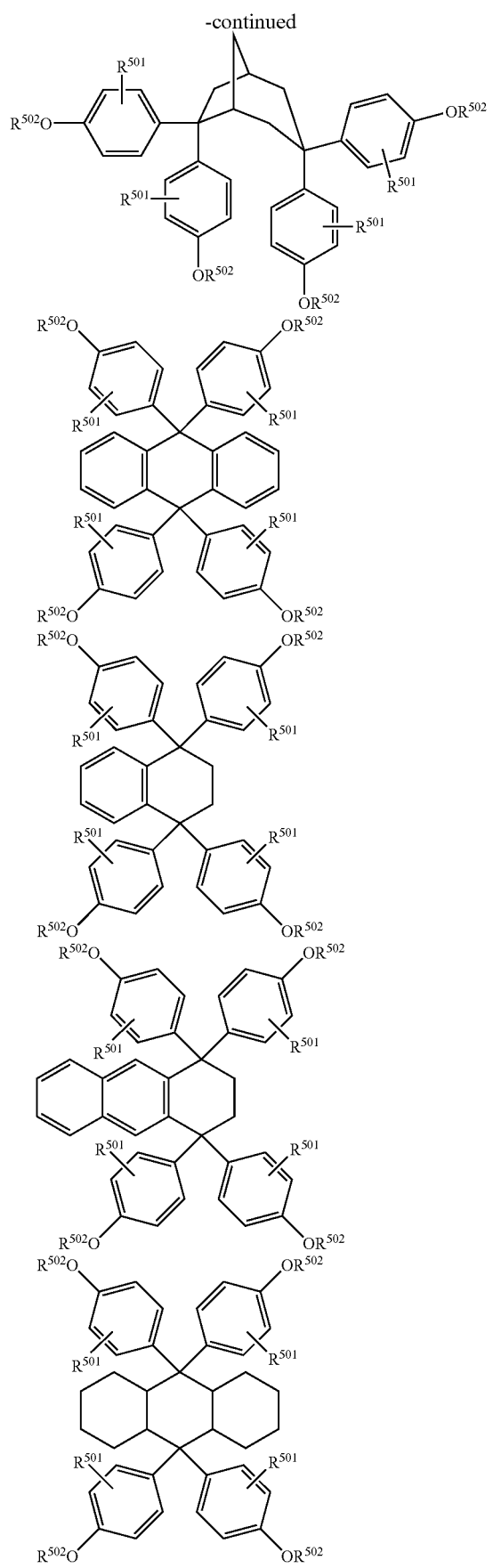
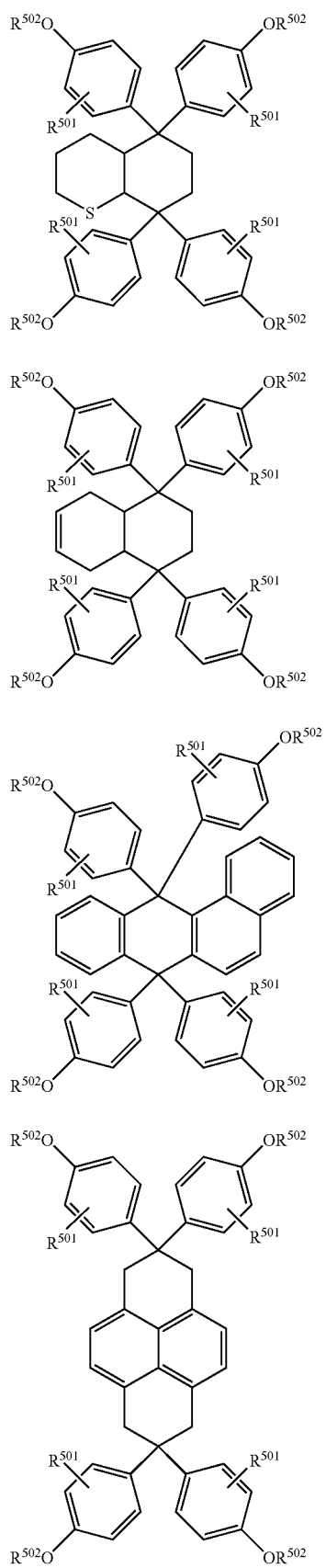

87
-continued
88
-continued
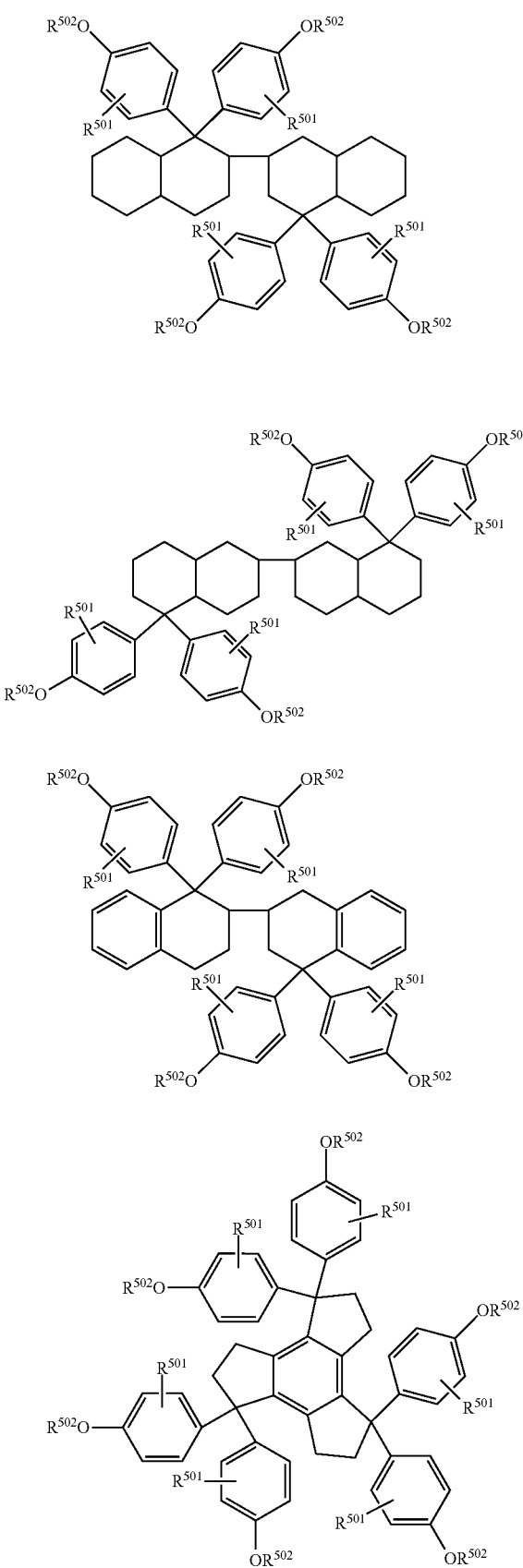
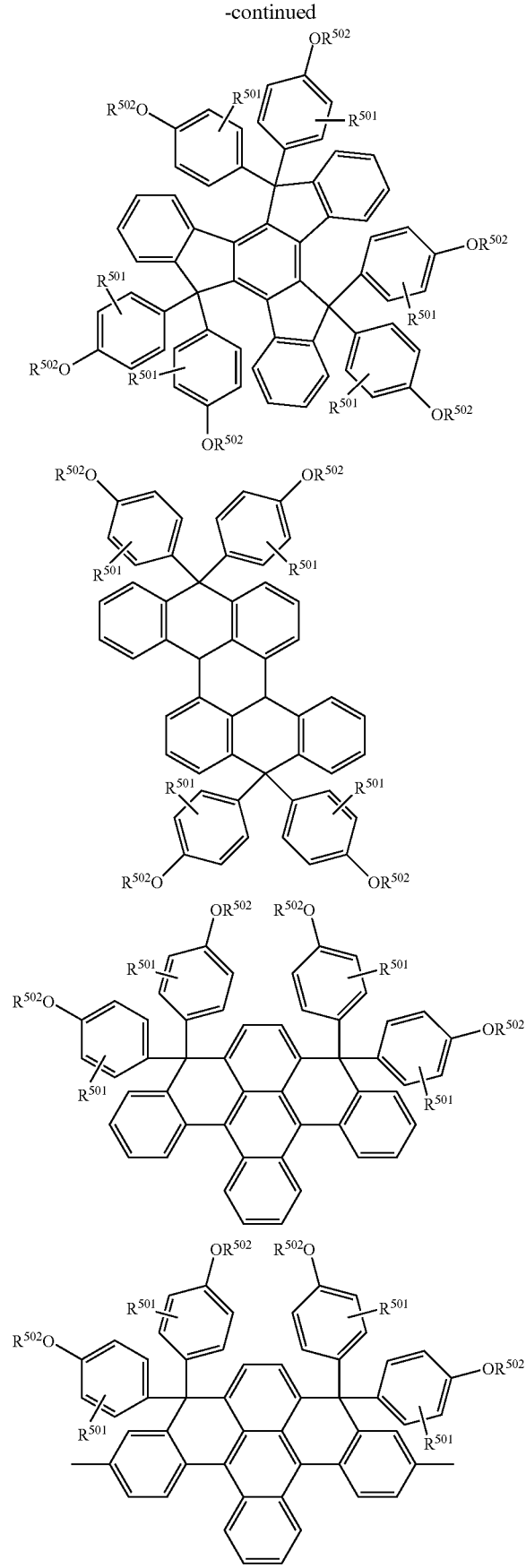

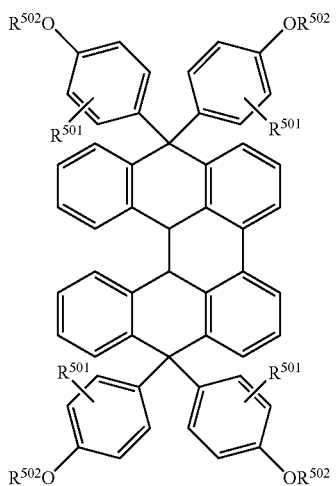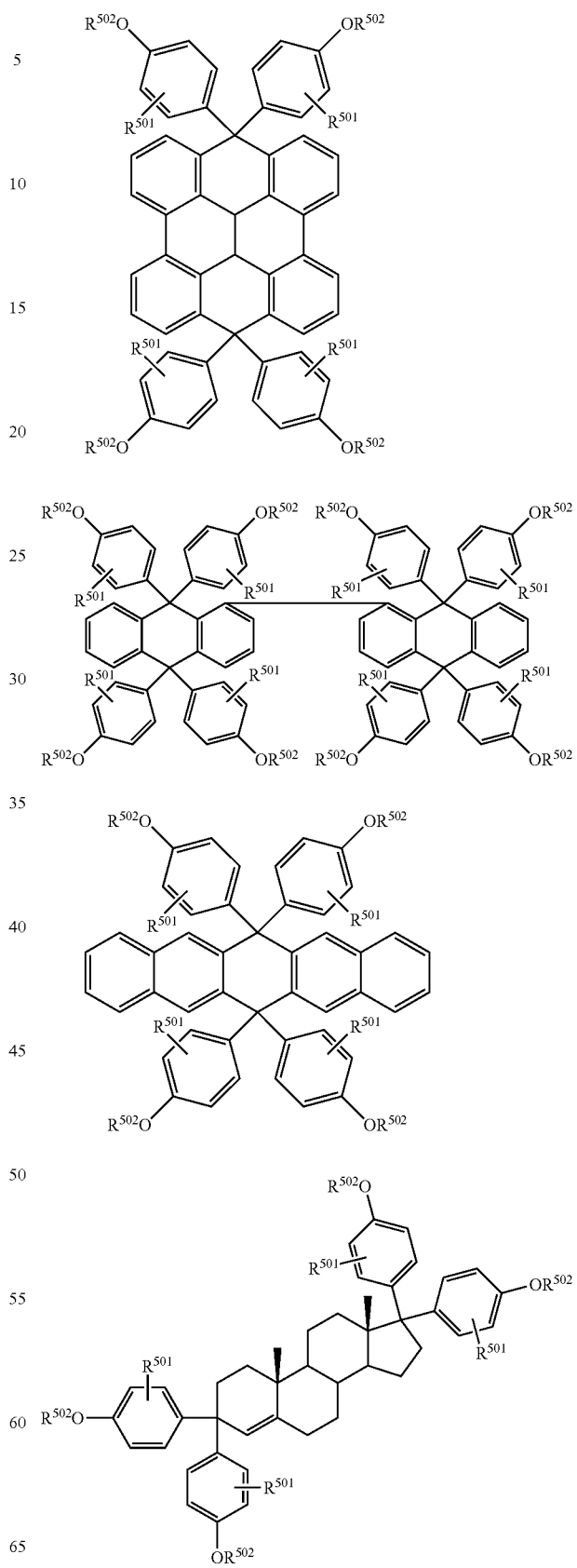

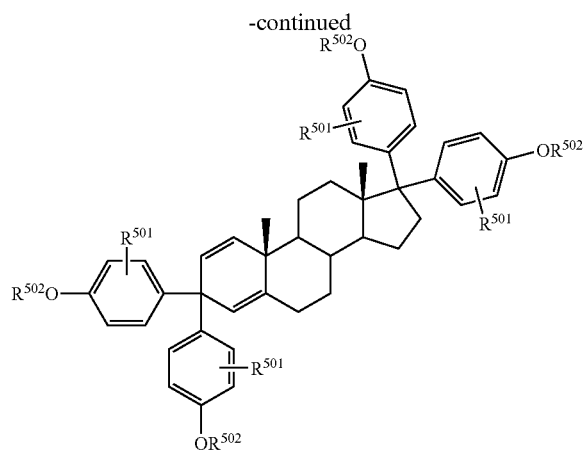

Further, the positive resist composition of the present invention may also contain a dissolution controlling material comprising calixarenes and calixresorcinols substituted by the acid labile group, as disclosed in the Japanese Patent Laid-Open (kokai) No. 11-322656.

The surfactant to be added in the present invention is not particularly restricted, but may be exemplified by a polyoxyethylene alkyl ether such as polyoxyethylene lauryl ether, polyoxyethylene stearyl ether, polyoxyethylene cetyl ether, and polyoxyethylene olein ether; a polyoxyethylene alkylaryl ether such as polyoxyethylene octylphenyl ether and polyoxyethylene nonylphenyl ether; a polyoxyethylene polyoxypropylene block copolymer; a sorbitane aliphatic acid ester such as sorbitane monolaurate, sorbitane monovalmitate, and sorbitane monostearate; a nonionic surfactant of a polyoxyethylene sorbitane aliphatic acid ester such as polyoxyethylene sorbitane monolaurate, polyoxyethylene sorbitane monopalmitate, polyoxyethylene sorbitane monostearate, polyoxyethylene sorbitane trioleate, and polyoxyethylene sorbitane tristearate; a fluoro surfactant such as F-Top EF301, EF303, and EF352 (manufactured by Tochem Products Co., Ltd.), Megafac F171, F172, and F173 (manufactured by Dainippon Ink & Chemicals, Inc.), Flolade FC430, FC431, and FC-4430 (manufactured by Sumitomo 3M Ltd.), Asahi Guard AG710, Surflon S-381, S-382, SC101, SC102, SC103, SC104, SC105, SC106, Surfinol E1004, KH-10, KH-20, KH-30, and KH-40 (manufactured by Asahi Glass Co., Ltd.); an organosiloxane polymer such as KP-341, X-70-092, and X-70-093 (manufactured by Shin-Etsu Chemical Co., Ltd.); and an acrylic acid or a methacrylic acid polymer such as Polyflow No. 75 and No. 95 (manufactured by Kyoeisha Yushikagaku Kogyo K. K.). Among them, FC430, FC-4430, Surflon S-381, Surfinol E1004, KH-20, and KH-30 are preferable. These may be used singly, or in a combination of two or more kinds.

The amount of the surfactant in the positive resist composition of the present invention, in particular the chemically amplified positive resist composition, is 2 parts or less, and preferably 1 part or less, relative to 100 parts of the base resin in the resist composition.

When the positive resist composition of the present invention, for instance, the chemically amplified positive resist composition containing an organic solvent, a polymer whose hydrogen atom of the carboxyl group is substituted by the acid labile group represented by the general formula (2), an acid generator, and a basic compound, is used for production of various integrated circuits, a publicly known lithography technology not particularly limited may be applied.

For instance, the positive resist composition of the present invention is applied on a substrate for an integrated circuit production (Si, $SiO_2$, SiN, SiON, TiN, WSi, BPSG, SOG, an organic anti-reflection film, and the like) or a substrate for a mask circuit production (Cr, CrO, CrON, MoSi, and the like) by an appropriate coating method such as a spin coat, a roll coat, a flow coat, a dip coat, a spray coat, and a doctor coat, in such a way as to give a film thickness of 0.1 to 2.0 micrometers. This is pre-baked on a hot plate at 60 to 150° C. and for 10 seconds to 30 minutes, and preferably at 80 to 120° C. and for 30 seconds to 20 minutes. Then, it is exposed directly or through a prescribed mask by a light source selected from high energy beams such as a ultraviolet beam, a far-ultraviolet beam, an electronic beam, an X-ray, an excimer laser, a γ beam, a synchrotron-radiation, and an extreme ultraviolet beam (soft X-ray) to obtained a desired pattern. The exposure amount is about 1 $mJ/cm^2$ to about 200 $mJ/cm^2$ and preferably 10 $mJ/cm^2$ to 100 $mJ/cm^2$, or 0.1 to 100 μC and preferably about 0.5 μC to about 50 μC. Then, a post-exposure bake (PEB) is performed on a hot plate at 60 to 150° C. and for 10 seconds to 30 minutes, and preferably at 80 to 120° C. and for 30 seconds to 20 minutes.

Further, a development is preformed by conventional methods such as a dip method, a puddle method, and a spray method for 3 seconds to 3 minutes and preferably 5 seconds to 2 minutes by using a developer of an alkaline aqueous solution such as tetramethyl ammonium hydroxide (TMAH) having a concentration of 0.1 to 5% by weight and preferably 2 to 3% by weight to form a desired positive pattern on a substrate, wherein an exposed area is dissolved in the developer while a non-exposed area is not dissolved. The positive resist composition of the present invention is most suitable for a micropatterning, in particular, by an electronic beam, an extreme ultraviolet beam (soft X-ray), an X-ray, a γ beam, and a synchrotron-radiation among high energy beams.

EXAMPLE

In the following, the present invention will be explained specifically by Synthetic Examples and Comparative Synthetic Examples, as well as by Examples and Comparative Examples, but the present invention is not restricted to the following Examples.

Examples of Monomer Syntheses

The acid labile polymerizable compounds of the present inventions were synthesized as following.

Example of Monomer Synthesis 1

Synthesis of (indane-2-yloxy)methyl methacrylate (Monomer 1)

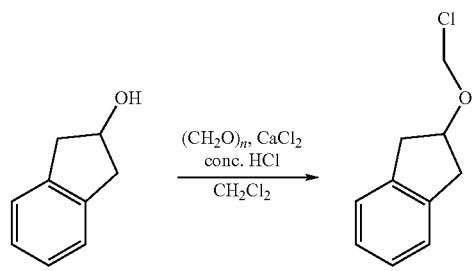

A mixture of 134 g of 2-hydroxyindane, 36.1 g of paraformaldehyde, 200 g of calcium chloride, and 1200 g of methylene chloride was agitated. Into the mixture was dropped 239 g of a concentrated hydrochloric acid at room temperature for 3 hours, and then the reaction mixture was agitated for 16 hours. After separated an organic layer from the mixture, the solvent was removed by distillation to obtain 183 g of chloromethyl(2-indanyl)ether as an oily matter.

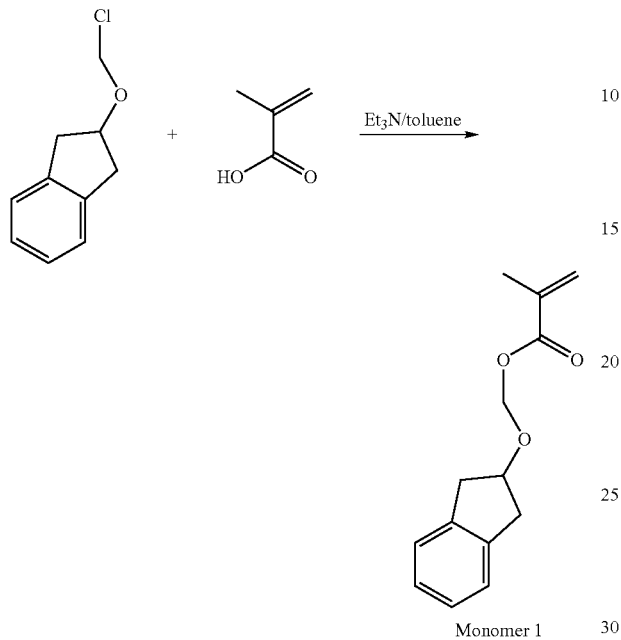

Monomer 1

Into a mixture of 103 g of methacrylic acid, 183 g of chloromethyl(2-indanyl)ether, and 1500 g of toluene was added 111 g of triethylamine under ice-cooling with agitation, and then the reaction mixture was agitated at room temperature for 16 hours. After a usual aqueous work-up, the solvent was removed by distillation to obtain a crude product. It was purified by a column chromatography to obtain 209 g of an objective product, (indane-2-yloxy)methyl methacrylate (yield 90%).

IR (thin film): 3072, 3023, 2954, 2908, 2846, 1724, 1637, 1483, 1459, 1452, 1434, 1419, 1376, 1322, 1297, 1211, 1159, 1095, 1006, 954, 917, 813, 742 cm$^{-1}$.

$^1$H-NMR (600 MHz, DMSO-d6): δ=1.91 (3H, m), 2.91 (2H, dd, J=16.5, 4.1 Hz), 3.15 (2H, dd, J=16.5, 6.0 Hz), 4.60 (1H, tt, J=6.0, 4.1 Hz), 5.40 (2H, s), 5.76 (1H, m), 6.12 (1H, m), 7.13 (2H, dd, J=5.5, 3.2 Hz), 7.20 (2H, dd, J=5.5, 3.2 Hz).

$^{13}$C-NMR (151 MHz, DMSO-d6): δ=17.83, 39.27, 80.17, 88.17, 124.39, 126.39, 126.43, 135.73, 140.40, 165.94.

Boiling point: 98-100° C./20.0 Pa.

In a similar manner to that of Monomer 1, following Monomers 2 to 5 were obtained.

Monomer 1: (indane-2-yloxy)methyl methacrylate
Monomer 2: (acenaphthene-2-yloxy)methyl methacrylate
Monomer 3: 1-(indane-2-yloxy)-2-methylpropyl methacrylate
Monomer 4: (indane-2-yloxy)methyl 4-vinylbenzoate
Monomer 5: (indane-2-yloxy)methyl 5-vinylnaphthalene-1-carboxylate Synthetic Example 1

Into a 2-liter flask were charged 7.0 g of Monomer 1, 4.7 g of 3-hydroxy-1-adamantyl methacrylate, 11.2 g of 3-oxo-2,7-dioxatricyclo[4.2.1.0$^{4,8}$]nonane-9-yl methacrylate, and 40 g of tetrahydrofurane as a solvent. The flask was cooled to −70° C. under a nitrogen atmosphere, and the procedure of a deaeration under vacuum followed by a nitrogen blow was repeated three times. After heated to a room temperature, 1.2 g of AIBN (azobisisobutyronitrile) was added as a polymerization initiator, and after the temperature was raised to 60° C., the reaction was carried out for 15 hours. The reaction solution was poured into 1 liter of isopropyl alcohol for precipitation, and the white solid obtained was filtered out and dried at 60° C. under a reduced pressure to obtain a white polymer.

A $^{13}$C-NMR, a $^1$H-NMR, and a GPC of the polymer thus obtained were measured to obtain the following analysis results.

Copolymer composition ratio (mole ratio): Monomer 1:3-hydroxy-1-adamantyl methacrylate:3-oxo-2,7-dioxatricyclo[4.2.1.0$^{4,8}$]nonane-9-yl methacrylate=0.30:0.20:0.50

Weight-average molecular weight (Mw): 8,400
Molecular weight distribution (Mw/Mn): 1.90
This polymer is designated as (Polymer-1).

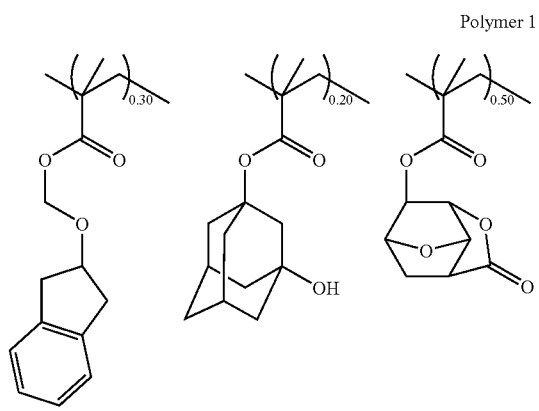

Polymer 1

Synthetic Example 2

Into a 2-liter flask were charged 7.0 g of Monomer 1, 4.7 g of 3-hydroxy-1-adamantyl methacrylate, 9.0 g of 3-oxo-2,7-dioxatricyclo[4.2.1.0$^{4,8}$]nonane-9-yl methacrylate, 5.0 g of 3,5-bis(hexafluoro-2-hydroxy-2-propyl)cyclohexyl methacrylate, and 40 g of tetrahydrofurane as a solvent. The flask was cooled to −70° C. under a nitrogen atmosphere, and the procedure of a deaeration under vacuum followed by a nitrogen blow was repeated three times. After heated to a room temperature, 1.2 g of AIBN (azobisisobutyronitrile) was added as a polymerization initiator, and after the temperature was raised to 60° C., the reaction was carried out for 15 hours. The reaction solution was poured into 1 liter of isopropyl alcohol for precipitation, and the white solid obtained was filtered out and dried at 60° C. under a reduced pressure to obtain a white polymer.

A $^{13}$C-NMR, a $^1$H-NMR, and a GPC of the polymer thus obtained were measured to obtain the following analysis results.

Copolymer composition ratio (mole ratio): Monomer 1:3-hydroxy-1-adamantyl methacrylate:3-oxo-2,7-dioxatricyclo[4.2.1.0$^{4,8}$]nonane-9-yl methacrylate:3,5-bis(hexafluoro-2-hydroxy-2-propyl)cyclohexyl methacrylate=0.30:0.20:0.40:0.10

Weight-average molecular weight (Mw): 8,600
Molecular weight distribution (Mw/Mn): 1.74
This polymer is designated as (Polymer-2).

Polymer 2

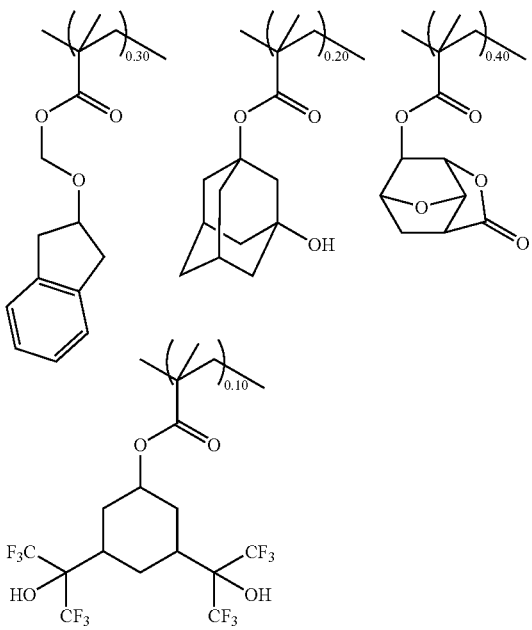

Synthetic Example 3

Into a 2-liter flask were charged 7.0 g of Monomer 1, 5.3 g of 4-hydroxyphenyl methacrylate, 13.3 g of 5-oxo-4-oxatricyclo[4.2.1.0$^{3,7}$]nonane-2-yl methacrylate, and 40 g of tetrahydrofurane as a solvent. The flask was cooled to −70° C. under a nitrogen atmosphere, and the procedure of a deaeration under vacuum followed by a nitrogen blow was repeated three times. After heated to a room temperature, 1.2 g of AIBN (azobisisobutyronitrile) was added as a polymerization initiator, and after the temperature was raised to 60° C., the reaction was carried out for 15 hours. The reaction solution was poured into 1 liter of isopropyl alcohol for precipitation, and the white solid obtained was filtered out and dried at 60° C. under a reduced pressure to obtain a white polymer.

A $^{13}$C-NMR, a $^1$H-NMR, and a GPC of the polymer thus obtained were measured to obtain the following analysis results.

Copolymer composition ratio (mole ratio): Monomer 1:4-hydroxyphenyl methacrylate:5-oxo-4-oxatricyclo[4.2.1.0$^{3,7}$] nonane-2-yl methacrylate=0.30:0.30:0.40

Weight-average molecular weight (Mw): 8,100
Molecular weight distribution (Mw/Mn): 1.72
This polymer is designated as (Polymer-3).

Polymer 3

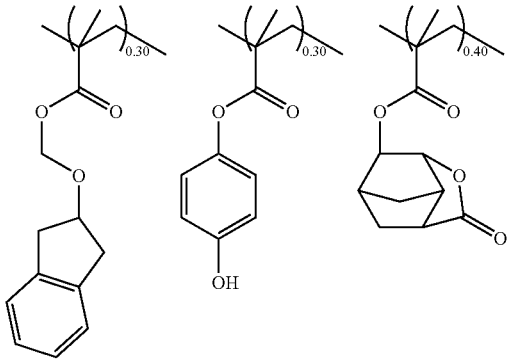

Synthetic Example 4

Into a 2-liter flask were charged 7.0 g of Monomer 1, 6.8 g of 1-hydroxynaphthalene-5-yl methacrylate, 6.8 g of tetrahydro-2-oxofurane-3-yl methacrylate, and 40 g of tetrahydrofurane as a solvent. The flask was cooled to −70° C. under a nitrogen atmosphere, and the procedure of a deaeration under vacuum followed by a nitrogen blow was repeated three times. After heated to a room temperature, 1.2 g of AIBN (azobisisobutyronitrile) was added as a polymerization initiator, and after the temperature was raised to 60° C., the reaction was carried out for 15 hours. The reaction solution was poured into 1 liter of isopropyl alcohol for precipitation, and the white solid obtained was filtered out and dried at 60° C. under a reduced pressure to obtain a white polymer.

A $^{13}$C-NMR, a $^1$H-NMR, and a GPC of the polymer thus obtained were measured to obtain the following analysis results.

Copolymer composition ratio (mole ratio): Monomer 1:1-hydroxynaphthalene-5-yl methacrylate:tetrahydro-2-oxofurane-3-yl methacrylate=0.30:0.30:0.40

Weight-average molecular weight (Mw): 6,300
Molecular weight distribution (Mw/Mn): 1.55
This polymer is designated as (Polymer-4).

Polymer 4

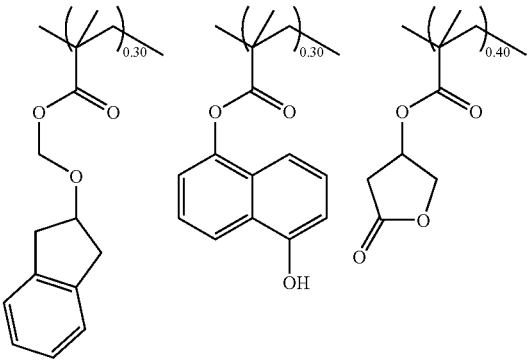

Synthetic Example 5

Into a 2-liter flask were charged 3.5 g of Monomer 1, 12.2 g of 4-acetoxy styrene, 1.7 g of acenaphthylene, and 20 g of tetrahydrofurane as a solvent. The flask was cooled to −70° C. under a nitrogen atmosphere, and the procedure of a deaeration under vacuum followed by a nitrogen blow was repeated three times. After heated to a room temperature, 1.2 g of AIBN (azobisisobutyronitrile) was added as a polymerization initiator, and after the temperature was raised to 60° C., the reaction was carried out for 15 hours. The reaction solution was poured into 1 liter of isopropyl alcohol for precipitation, and the white solid obtained was redissolved in 100 mL of methanol and 200 mL of tetrahydrofurane, added by 10 g of triethylamine and 10 g of water, and then a deprotection reaction of the acetyl group was carried out at 70° C. for 5 hours. The reaction solution was neutralized by acetic acid, concentrated, and dissolved in 100 mL of acetone. In a similar manner to those shown in the above, precipitation, filtration, and drying at 60° C. were carried out to obtain a white polymer.

A $^{13}$C-NMR, a $^1$H-NMR, and a GPC of the polymer thus obtained were measured to obtain the following analysis results.

Copolymer composition ratio (mole ratio): Monomer-1:4-hydroxy styrene:acenaphtylene=0.15:0.75:0.10
Weight-average molecular weight (Mw): 5,700
Molecular weight distribution (Mw/Mn): 1.64
This polymer is designated as (Polymer-5).

Polymer 5

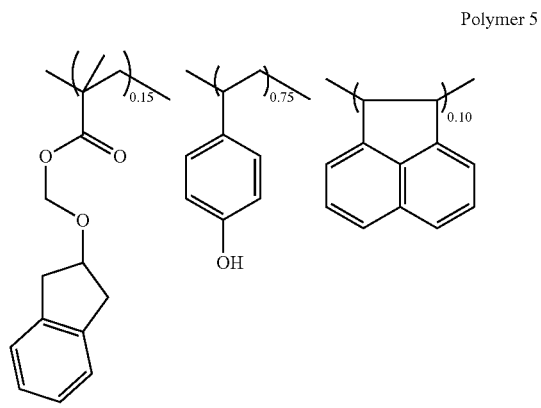

Synthetic Example 6

Into a 2-liter flask were charged 3.7 g of Monomer 2, 12.2 g of 4-acetoxy styrene, 1.3 g of indene, and 20 g of tetrahydrofurane as a solvent. The flask was cooled to −70° C. under a nitrogen atmosphere, and the procedure of a deaeration under vacuum followed by a nitrogen blow was repeated three times. After heated to a room temperature, 1.2 g of AIBN (azobisisobutyronitrile) was added as a polymerization initiator, and after the temperature was raised to 60° C., the reaction was carried out for 15 hours. The reaction solution was poured into 1 liter of isopropyl alcohol for precipitation, and the white solid obtained was redissolved in 100 mL of methanol and 200 mL of tetrahydrofurane, added by 10 g of triethylamine and 10 g of water, and then a deprotection reaction of the acetyl group was carried out at 70° C. for 5 hours. The reaction solution was neutralized by acetic acid, concentrated, and dissolved in 100 mL of acetone. In a similar manner to those shown in the above, precipitation, filtration, and drying at 60° C. were carried out to obtain a white polymer.

A $^{13}$C-NMR, a $^1$H-NMR, and a GPC of the polymer thus obtained were measured to obtain the following analysis results.

Copolymer composition ratio (mole ratio): Monomer-2:4-hydroxy styrene:indene=0.15:0.75:0.10
Weight-average molecular weight (Mw): 5,900
Molecular weight distribution (Mw/Mn): 1.69
This polymer is designated as (Polymer-6).

Polymer 6

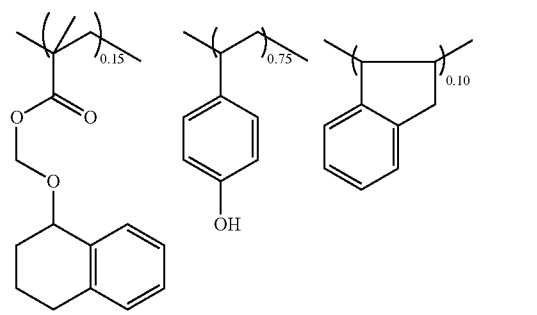

Synthetic Example 7

Into a 2-liter flask were charged 4.1 g of Monomer 3, 12.2 g of 4-acetoxy styrene, 1.6 g of coumarin, and 20 g of tetrahydrofurane as a solvent. The flask was cooled to −70° C. under a nitrogen atmosphere, and the procedure of a deaeration under vacuum followed by a nitrogen blow was repeated three times. After heated to a room temperature, 1.2 g of AIBN (azobisisobutyronitrile) was added as a polymerization initiator, and after the temperature was raised to 60° C., the reaction was carried out for 15 hours. The reaction solution was poured into 1 liter of isopropyl alcohol for precipitation, and the white solid obtained was redissolved in 100 mL of methanol and 200 mL of tetrahydrofurane, added by 10 g of triethylamine and 10 g of water, and then a deprotection reaction of the acetyl group was carried out at 70° C. for 5 hours. The reaction solution was neutralized by acetic acid, concentrated, and dissolved in 100 mL of acetone. In a similar manner to those shown in the above, precipitation, filtration, and drying at 60° C. were carried out to obtain a white polymer.

A $^{13}$C-NMR, a $^1$H-NMR, and a GPC of the polymer thus obtained were measured to obtain the following analysis results.

Copolymer composition ratio (mole ratio): Monomer-3:4-hydroxy styrene:coumarin=0.15:0.75:0.10
Weight-average molecular weight (Mw): 6,100
Molecular weight distribution (Mw/Mn): 1.65
This polymer is designated as (Polymer-7).

Polymer 7

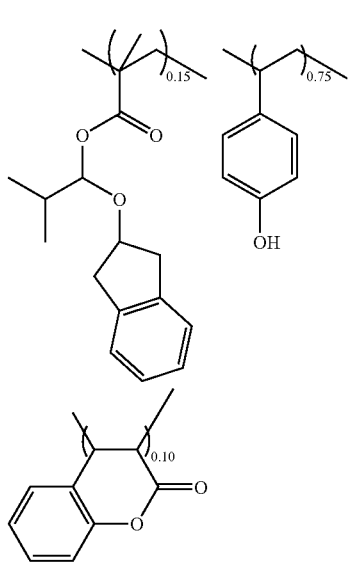

Synthetic Example 8

Into a 2-liter flask were charged 4.4 g of Monomer 4, 12.2 g of 4-acetoxy styrene, 1.6 g of coumarin, and 20 g of tetrahydrofurane as a solvent. The flask was cooled to −70° C. under a nitrogen atmosphere, and the procedure of a deaeration under vacuum followed by a nitrogen blow was repeated three times. After heated to a room temperature, 1.2 g of AIBN (azobisisobutyronitrile) was added as a polymerization initiator, and after the temperature was raised to 60° C., the reaction was carried out for 15 hours. The reaction solution was poured into 1 liter of isopropyl alcohol for precipitation, and the white solid obtained was redissolved in 100 mL of methanol and 200 mL of tetrahydrofurane, added by 10 g of triethylamine and 10 g of water, and then a deprotection reaction of the acetyl group was carried out at 70° C. for 5 hours. The reaction solution was neutralized by acetic acid, concentrated, and dissolved in 100 mL of acetone. In a similar manner to those shown in the above, precipitation, filtration, and drying at 60° C. were carried out to obtain a white polymer.

A $^{13}$C-NMR, a $^1$H-NMR, and a GPC of the polymer thus obtained were measured to obtain the following analysis results.

Copolymer composition ratio (mole ratio): Monomer-4:4-hydroxy styrene:coumarin=0.15:0.75:0.10

Weight-average molecular weight (Mw): 6,600

Molecular weight distribution (Mw/Mn): 1.72

This polymer is designated as (Polymer-8).

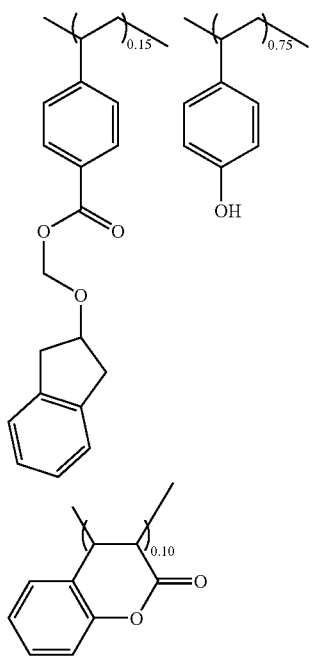

Polymer 8

A $^{13}$C-NMR, a $^1$H-NMR, and a GPC of the polymer thus obtained were measured to obtain the following analysis results.

Copolymer composition ratio (mole ratio): Monomer-5:4-hydroxy styrene:coumarin=0.13:0.75:0.12

Weight-average molecular weight (Mw): 6,600

Molecular weight distribution (Mw/Mn): 1.72

This polymer is designated as (Polymer-9).

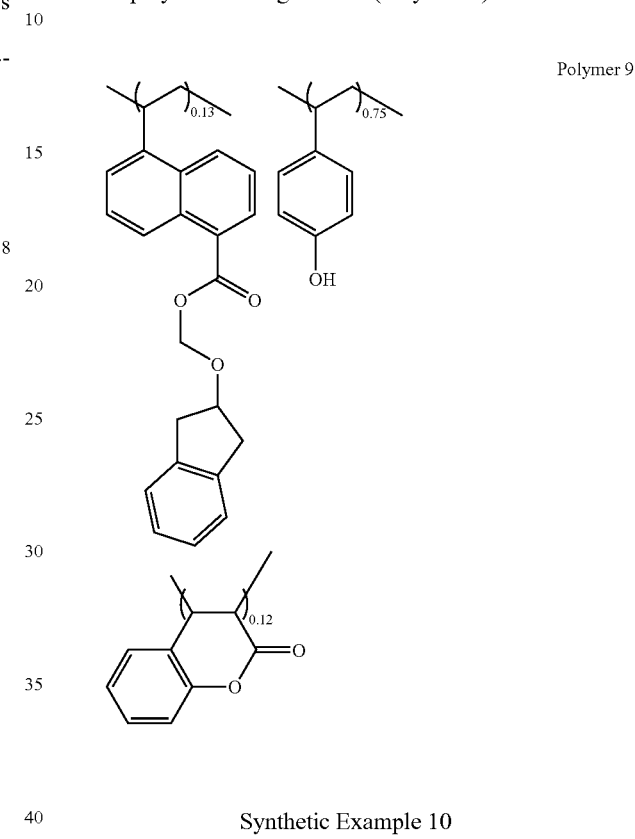

Polymer 9

Synthetic Example 9

Into a 2-liter flask were charged 4.5 g of Monomer 5, 12.2 g of 4-acetoxy styrene, 1.8 g of coumarin, and 20 g of tetrahydrofurane as a solvent. The flask was cooled to −70° C. under a nitrogen atmosphere, and the procedure of a deaeration under vacuum followed by a nitrogen blow was repeated three times. After heated to a room temperature, 1.2 g of AIBN (azobisisobutyronitrile) was added as a polymerization initiator, and after the temperature was raised to 60° C., the reaction was carried out for 15 hours. The reaction solution was poured into 1 liter of isopropyl alcohol for precipitation, and the white solid obtained was redissolved in 100 mL of methanol and 200 mL of tetrahydrofurane, added by 10 g of triethylamine and 10 g of water, and then a deprotection reaction of the acetyl group was carried out at 70° C. for 5 hours. The reaction solution was neutralized by acetic acid, concentrated, and dissolved in 100 mL of acetone. In a similar manner to those shown in the above, precipitation, filtration, and drying at 60° C. were carried out to obtain a white polymer.

Synthetic Example 10

Into a 2-liter flask were charged 7.0 g of Monomer 1, 5.3 g of 4-hydroxyphenyl methacrylate, 6.7 g of 3-oxo-2,7-dioxatricyclo[4.2.1.0$^{4,8}$]nonane-9-yl methacrylate, 6.5 g of PAG Monomer 1, and 40 g of tetrahydrofurane as a solvent. The flask was cooled to −70° C. under a nitrogen atmosphere, and the procedure of a deaeration under vacuum followed by a nitrogen blow was repeated three times. After heated to a room temperature, 1.2 g of AIBN (azobisisobutyronitrile) was added as a polymerization initiator, and after the temperature was raised to 60° C., the reaction was carried out for 15 hours. The reaction solution was poured into 1 liter of isopropyl alcohol for precipitation, and the white solid obtained was filtered out and dried at 60° C. under a reduced pressure to obtain a white polymer.

A 13C-NMR, a $^1$H-NMR, and a GPC of the polymer thus obtained were measured to obtain the following analysis results.

Copolymer composition ratio (mole ratio): Monomer 1:4-hydroxyphenyl methacrylate:3-oxo-2,7-dioxatricyclo[4.2.1.0$^{4,8}$]nonane-9-yl methacrylate:PAG Monomer 1=0.30:0.30:0.30:0.10

Weight-average molecular weight (Mw): 7,900

Molecular weight distribution (Mw/Mn): 1.88

This polymer is designated as (Polymer-10).

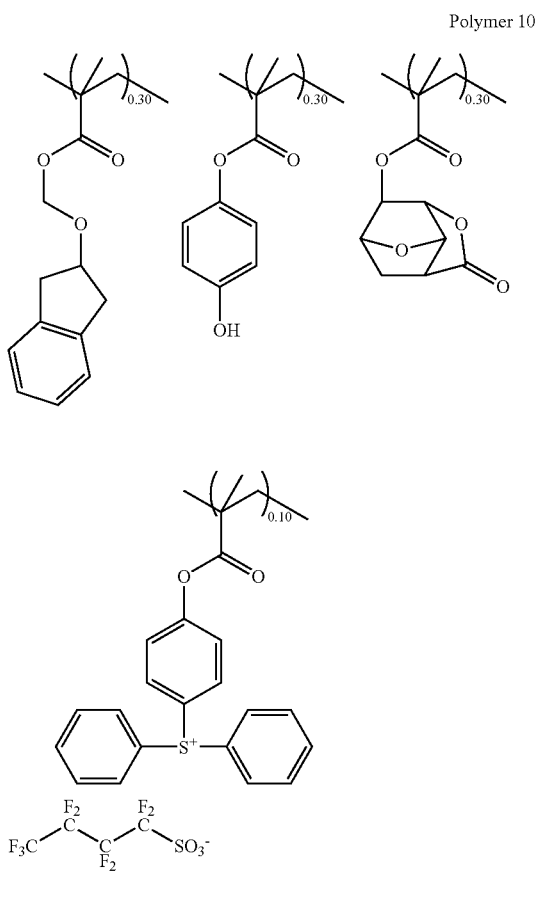

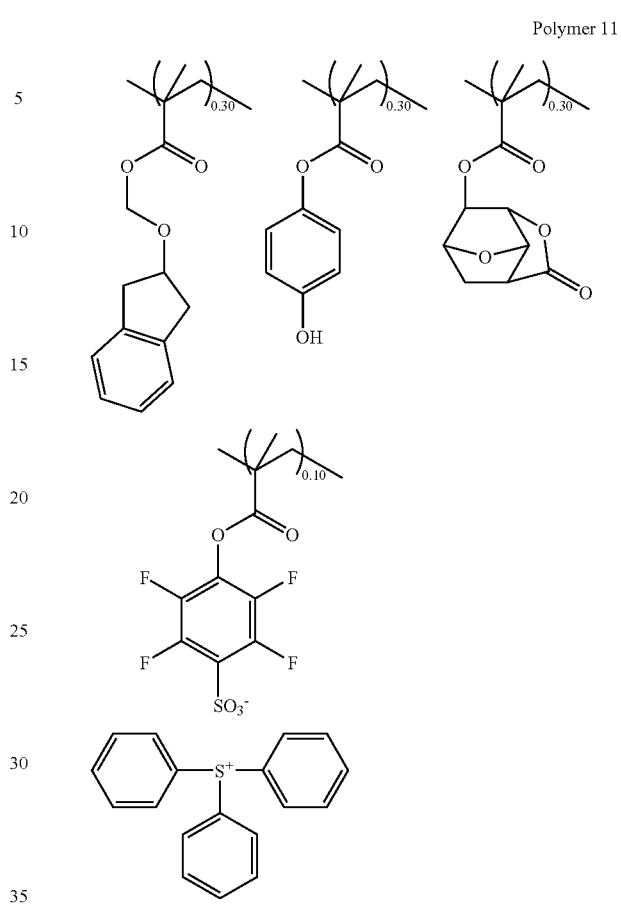

Synthetic Example 11

Into a 2-liter flask were charged 7.0 g of Monomer 1, 5.3 g of 4-hydroxyphenyl methacrylate, 6.7 g of 3-oxo-2,7-dioxatricyclo[4.2.1.0$^{4,8}$]nonane-9-yl methacrylate, 5.7 g of PAG Monomer 2, and 40 g of tetrahydrofurane as a solvent. The flask was cooled to −70° C. under a nitrogen atmosphere, and the procedure of a deaeration under vacuum followed by a nitrogen blow was repeated three times. After heated to a room temperature, 1.2 g of AIBN (azobisisobutyronitrile) was added as a polymerization initiator, and after the temperature was raised to 60° C., the reaction was carried out for 15 hours. The reaction solution was poured into 1 liter of isopropyl alcohol for precipitation, and the white solid obtained was filtered out and dried at 60° C. under a reduced pressure to obtain a white polymer.

A $^{13}$C-NMR, a $^1$H-NMR, and a GPC of the polymer thus obtained were measured to obtain the following analysis results.

Copolymer composition ratio (mole ratio): Monomer 1:4-hydroxyphenyl methacrylate:3-oxo-2,7-dioxatricyclo[4.2.1.0$^{4,8}$]nonane-9-yl methacrylate:PAG Monomer 2=0.30:0.30:0.30:0.10

Weight-average molecular weight (Mw): 7,700

Molecular weight distribution (Mw/Mn): 1.88

This polymer is designated as (Polymer-11).

Synthetic Example 12

Into a 2-liter flask were charged 7.0 g of Monomer 1, 5.3 g of 4-hydroxyphenyl methacrylate, 6.7 g of 3-oxo-2,7-dioxatricyclo[4.2.1.0$^{4,8}$]nonane-9-yl methacrylate, 5.6 g of PAG Monomer 3, and 40 g of tetrahydrofurane as a solvent. The flask was cooled to −70° C. under a nitrogen atmosphere, and the procedure of a deaeration under vacuum followed by a nitrogen blow was repeated three times. After heated to a room temperature, 1.2 g of AIBN (azobisisobutyronitrile) was added as a polymerization initiator, and after the temperature was raised to 60° C., the reaction was carried out for 15 hours. The reaction solution was poured into 1 liter of isopropyl alcohol for precipitation, and the white solid obtained was filtered out and dried at 60° C. under a reduced pressure to obtain a white polymer.

A $^{13}$C-NMR, a $^1$H-NMR, and a GPC of the polymer thus obtained were measured to obtain the following analysis results.

Copolymer composition ratio (mole ratio): Monomer 1:4-hydroxyphenyl methacrylate:3-oxo-2,7-dioxatricyclo[4.2.1.0$^{4,8}$ ]nonane-9-yl methacrylate:PAG Monomer 3=0.30:0.30:0.30:0.10

Weight-average molecular weight (Mw): 7,600

Molecular weight distribution (Mw/Mn): 1.59

This polymer is designated as (Polymer-12).

Polymer 12

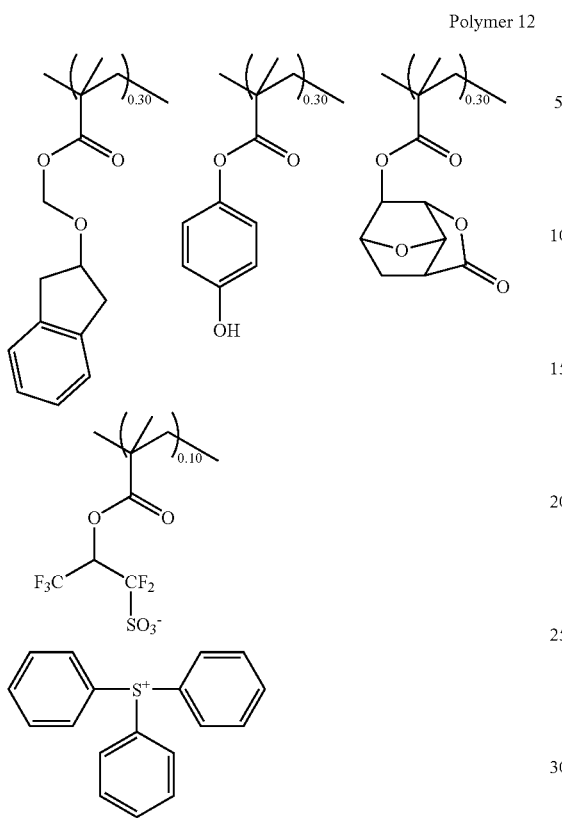

Synthetic Example 13

Into a 2-liter flask were charged 3.5 g of Monomer 1, 4.1 g of 3-ethyl-3-exotetracyclo[4.4.0.1$^{2,5}$.1$^{7,10}$]dodecanyl methacrylate, 5.3 g of 4-hydroxyphenyl methacrylate, 6.5 g of 2,7-dihydro-2-oxobenzo[C]furane-5-yl methacrylate, 5.6 g of PAG Monomer 3, and 40 g of tetrahydrofurane as a solvent. The flask was cooled to −70° C. under a nitrogen atmosphere, and the procedure of a deaeration under vacuum followed by a nitrogen blow was repeated three times. After heated to a room temperature, 1.2 g of AIBN (azobisisobutyronitrile) was added as a polymerization initiator, and after the temperature was raised to 60° C., the reaction was carried out for 15 hours. The reaction solution was poured into 1 liter of isopropyl alcohol for precipitation, and the white solid obtained was filtered out and dried at 60° C. under a reduced pressure to obtain a white polymer.

A $^{13}$C-NMR, a $^{1}$H-NMR, and a GPC of the polymer thus obtained were measured to obtain the following analysis results.

Copolymer composition ratio (mole ratio): Monomer 1:3-ethyl-3-exotetracyclo[4.4.0.1$^{2,5}$.1$^{7,10}$]dodecanyl methacrylate:4-hydroxyphenyl methacrylate:2,7-dihydro-2-oxobenzo[C]furane-5-yl methacrylate:PAG Monomer 3=0.15:0.15:0.30:0.30:0.10

Weight-average molecular weight (Mw): 7,900

Molecular weight distribution (Mw/Mn): 1.79

This polymer is designated as (Polymer-13).

Polymer 13

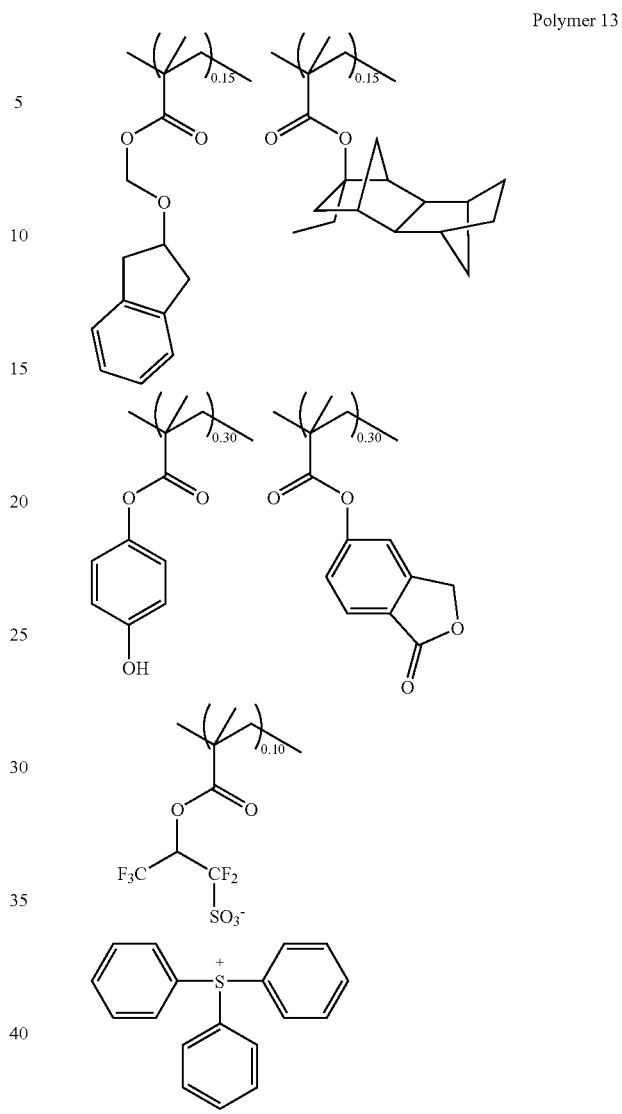

Synthetic Example 14

Into a 2-liter flask were charged 7.0 g of Monomer 1, 6.4 g of 6-acetoxy-2-vinyl naphthalene, 6.7 g of 3-oxo-2,7-dioxatricyclo[4.2.1.0$^{4,8}$]nonane-9-yl methacrylate, 5.6 g of PAG Monomer 3, and 40 g of tetrahydrofurane as a solvent. The flask was cooled to −70° C. under a nitrogen atmosphere, and the procedure of a deaeration under vacuum followed by a nitrogen blow was repeated three times. After heated to a room temperature, 1.2 g of AIBN (azobisisobutyronitrile) was added as a polymerization initiator, and after the temperature was raised to 60° C., the reaction was carried out for 15 hours. The reaction solution was poured into 1 liter of isopropyl alcohol for precipitation, and the white solid obtained was redissolved in 100 mL of methanol and 200 mL of tetrahydrofurane, added by 10 g of triethylamine and 10 g of water, and then a deprotection reaction of the acetyl group was carried out at 70° C. for 5 hours. The reaction solution was neutralized by acetic acid, concentrated, and dissolved in 100 mL of acetone. In a similar manner to those shown in the above, precipitation, filtration, and drying at 60° C. were carried out to obtain a white polymer.

A $^{13}$C-NMR, a $^1$H-NMR, and a GPC of the polymer thus obtained were measured to obtain the following analysis results.

Copolymer composition ratio (mole ratio): Monomer 1:6-hydroxy-2-vinyl naphthalene:3-oxo-2,7-dioxatricyclo[4.2.1.0$^{4,8}$]nonane-9-yl methacrylate:PAG Monomer 3=0.30:0.30:0.30:0.10

Weight-average molecular weight (Mw): 8,900
Molecular weight distribution (Mw/Mn): 1.93
This polymer is designated as (Polymer-14).

Polymer 14

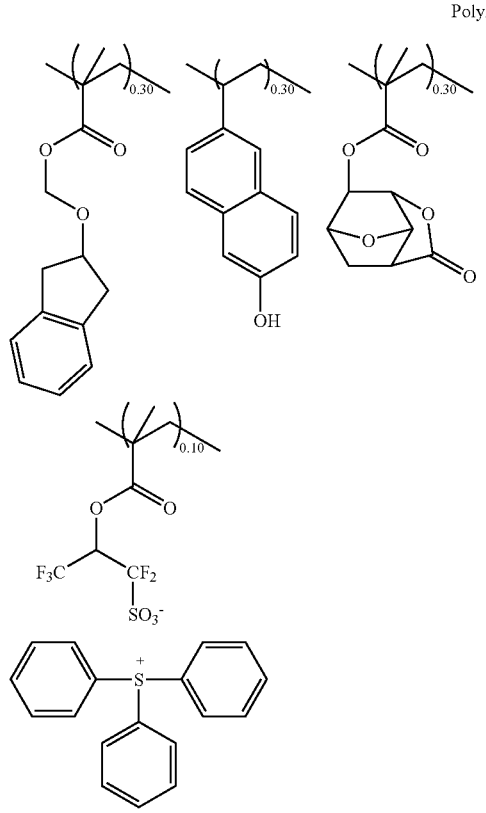

Synthetic Example 15

Into a 2-liter flask were charged 7.0 g of Monomer 1, 5.3 g of 4-hydroxyphenyl methacrylate, 6.7 g of 3-oxo-2,7-dioxatricyclo[4.2.1.0$^{4,8}$]nonane-9-yl methacrylate, 3.4 g of PAG Monomer 4, and 40 g of tetrahydrofurane as a solvent. The flask was cooled to −70° C. under a nitrogen atmosphere, and the procedure of a deaeration under vacuum followed by a nitrogen blow was repeated three times. After heated to a room temperature, 1.2 g of AIBN (azobisisobutyronitrile) was added as a polymerization initiator, and after the temperature was raised to 60° C., the reaction was carried out for 15 hours. The reaction solution was poured into 1 liter of isopropyl alcohol for precipitation, and the white solid obtained was filtered out and dried at 60° C. under a reduced pressure to obtain a white polymer.

A $^{13}$C-NMR, a $^1$H-NMR, and a GPC of the polymer thus obtained were measured to obtain the following analysis results.

Copolymer composition ratio (mole ratio): Monomer 1:4-hydroxyphenyl methacrylate:3-oxo-2,7-dioxatricyclo[4.2.1.0$^{4,8}$]nonane-9-yl methacrylate:PAG Monomer 4=0.30:0.30:0.30:0.10

Weight-average molecular weight (Mw): 7,200
Molecular weight distribution (Mw/Mn): 1.51
This polymer is designated as (Polymer-15).

Polymer 15

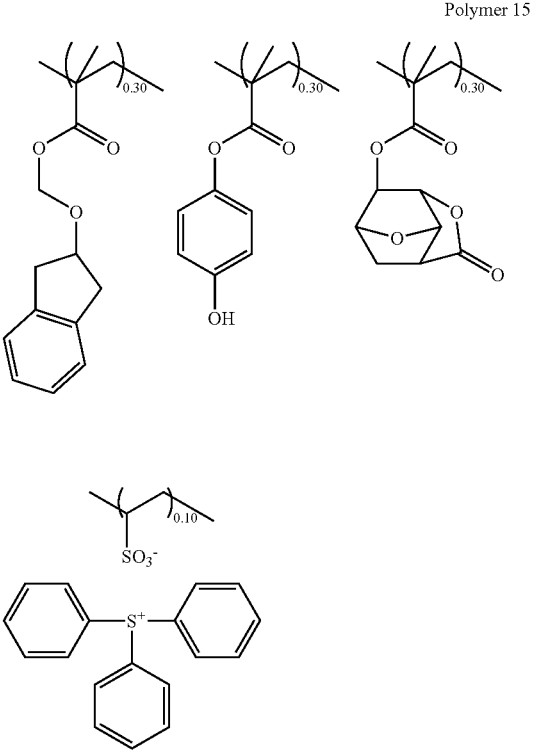

Synthetic Example 16

Into a 2-liter flask were charged 7.0 g of Monomer 1, 5.3 g of 4-hydroxyphenyl methacrylate, 6.7 g of 3-oxo-2,7-dioxatricyclo[4.2.1.0$^{4,8}$]nonane-9-yl methacrylate, 3.8 g of PAG Monomer 5, and 40 g of tetrahydrofurane as a solvent. The flask was cooled to −70° C. under a nitrogen atmosphere, and the procedure of a deaeration under vacuum followed by a nitrogen blow was repeated three times. After heated to a room temperature, 1.2 g of AIBN (azobisisobutyronitrile) was added as a polymerization initiator, and after the temperature was raised to 60° C., the reaction was carried out for 15 hours. The reaction solution was poured into 1 liter of isopropyl alcohol for precipitation, and the white solid obtained was filtered out and dried at 60° C. under a reduced pressure to obtain a white polymer.

A $^{13}$C-NMR, a $^1$H-NMR, and a GPC of the polymer thus obtained were measured to obtain the following analysis results.

Copolymer composition ratio (mole ratio): Monomer 1:4-hydroxyphenyl methacrylate:3-oxo-2,7-dioxatricyclo[4.2.1.0$^{4,8}$]nonane-9-yl methacrylate:PAG Monomer 5=0.30:0.30:0.30:0.10

Weight-average molecular weight (Mw): 7,000
Molecular weight distribution (Mw/Mn): 1.56
This polymer is designated as (Polymer-16).

Polymer 16
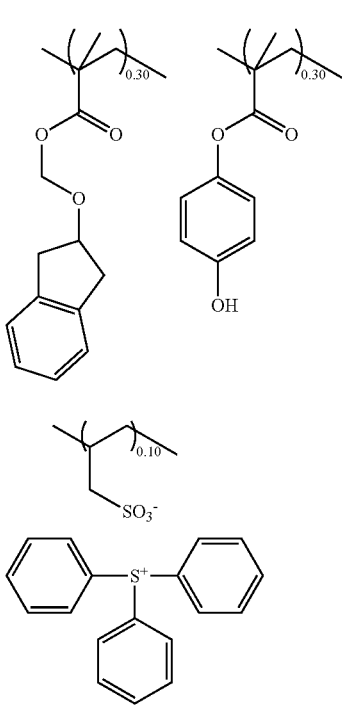
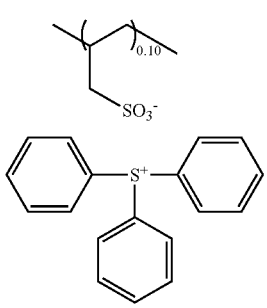
Here, PAG Monomers 1 to 5 and Monomers 1 to 5 used in the above are shown below.
Monomer 1
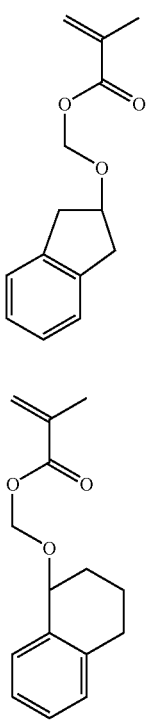
Monomer 2
Monomer 3
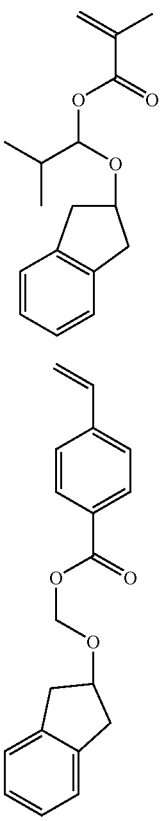
Monomer 4
Monomer 5
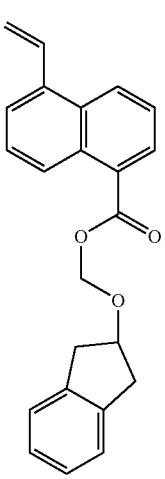
PAG Monomer 1
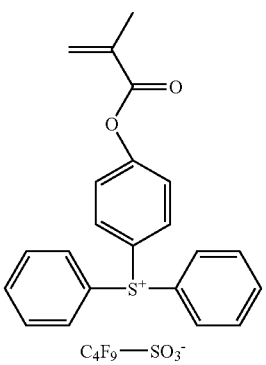

PAG Monomer 2

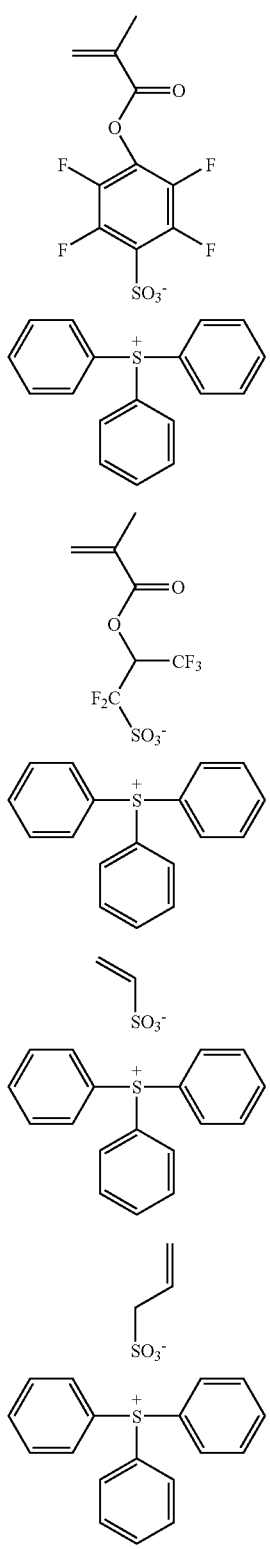

PAG Monomer 3

PAG Monomer 4

PAG Monomer 5

Comparative Synthetic Example 1

In a similar manner to that of the Synthetic Examples as mentioned above, the following polymer was synthesized.

A $^{13}$C-NMR, a $^1$H-NMR, and a GPC of the polymer thus obtained were measured to obtain the following analysis results.

Copolymer composition ratio (mole ratio): 1-ethylcyclopentyl methacrylic ester:hydroxy styrene:indene=0.15:.0.75:0.10

Weight-average molecular weight (Mw): 8,100
Molecular weight distribution (Mw/Mn): 1.79
This polymer is designated as (Comparative Polymer-1).

Comparative Polymer 1

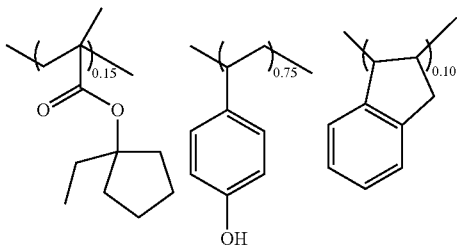

Comparative Synthetic Example 2

In a similar manner to that of the Synthetic Examples as mentioned above, the following polymer was synthesized.

A $^{13}$C-NMR, a $^1$H-NMR, and a GPC of the polymer thus obtained were measured to obtain the following analysis results.

Copolymer composition ratio (mole ratio): 1-ethylcyclopentyl methacrylate:3-hydroxy-1-adamantyl methacrylate:3-oxo-2,7-dioxatricyclo[4.2.1.0$^{4,8}$]nonane-9-yl methacrylate:3,5-bis(hexafluoro-2-hydroxy-2-propyl)cyclohexyl methacrylate=0.30:0.20:0.40:0.10

Weight-average molecular weight (Mw): 8,200
Molecular weight distribution (Mw/Mn): 1.72
This polymer is designated as (Comparative Polymer-2).

Comparative Polymer 2

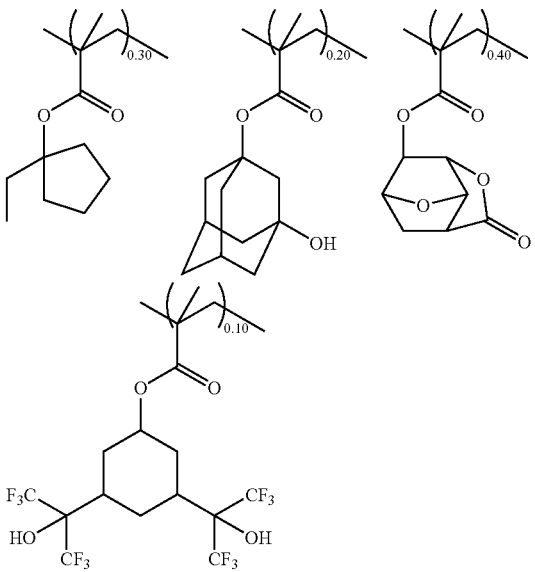

Comparative Synthetic Example 3

In a similar manner to that of the Synthetic Examples as mentioned above, the following polymer was synthesized.

A $^{13}$C-NMR, a $^1$H-NMR, and a GPC of the polymer thus obtained were measured to obtain the following analysis results.

Copolymer composition ratio (mole ratio): 1-ethoxymethyl methacrylate:3-hydroxy-1-adamantyl methacrylate:3-oxo-2,7-dioxatricyclo[4.2.1.0$^{4,8}$]nonane-9-yl methacrylate:3,5-bis(hexafluoro-2-hydroxy-2-propyl)cyclohexyl methacrylate=0.35:0.20:0.35:0.10

Weight-average molecular weight (Mw): 9,100
Molecular weight distribution (Mw/Mn): 1.76
This polymer is designated as (Comparative Polymer-3).

Comparative Polymer 3

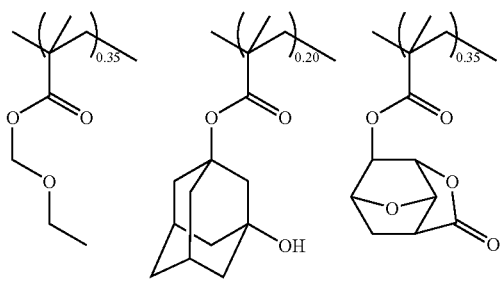

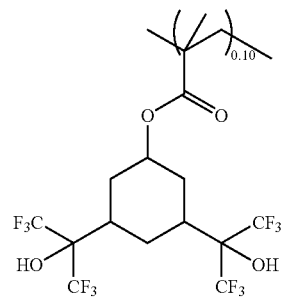

Examples and Comparative Examples

Each of the polymers as synthesized above was dissolved into a solvent containing 100 ppm of FC-4430 (surfactant, manufactured by 3M Company) in accordance with the compositions shown in Table 1. The solution thus obtained was filtered through a filter of a 0.2-micrometer size to obtain a positive resist composition (Examples 1 to 20 and Comparative Examples 1 to 3).

TABLE 1

| | Polymer (parts by weight) | Acid generator (parts by weight) | Base (parts by weight) | Dissolution inhibitor (parts by weight) | Organic solvent (parts by weight) | Sensitivity (μC/cm$^2$) | Degree of Resolution (nm) | Edge roughness (nm) |
|---|---|---|---|---|---|---|---|---|
| Example 1 | Polymer 1 (100) | PAG 1 (12) | Amine 1 (0.6) | — | PGMEA (1500) CyH (200) | 25.5 | 70 | 6.8 |
| Example 2 | Polymer 2 (100) | PAG 1 (12) | Amine 1 (0.6) | — | PGMEA (1500) CyH (200) | 22.3 | 70 | 6.4 |
| Example 3 | Polymer 3 (100) | PAG 1 (12) | Amine 1 (0.6) | — | PGMEA (1500) CyH (200) | 16.4 | 70 | 6.1 |
| Example 4 | Polymer 4 (100) | PAG 1 (12) | Amine 1 (0.6) | — | PGMEA (1500) CyH (200) | 17.3 | 70 | 6.8 |
| Example 5 | Polymer 5 (100) | PAG 1 (12) | Amine 1 (0.6) | — | PGMEA (1700) | 14.2 | 70 | 6.7 |
| Example 6 | Polymer 6 (100) | PAG 1 (12) | Amine 1 (0.6) | — | PGMEA (1700) | 15.3 | 70 | 6.7 |
| Example 7 | Polymer 7 (100) | PAG 1 (12) | Amine 1 (0.6) | — | PGMEA (1700) | 13.6 | 70 | 6.8 |
| Example 8 | Polymer 8 (100) | PAG 1 (12) | Amine 1 (0.6) | — | PGMEA (1700) | 14.3 | 70 | 6.5 |
| Example 9 | Polymer 9 (100) | PAG 1 (12) | Amine 1 (0.6) | — | PGMEA (1700) | 18.2 | 70 | 6.9 |
| Example 10 | Polymer 10 (100) | — | Amine 1 (0.6) | — | PGMEA (1500) CyH (200) | 16.3 | 65 | 4.3 |
| Example 11 | Polymer 11 (100) | — | Amine 1 (0.6) | — | PGMEA (1500) CyH (200) | 17.8 | 65 | 4.6 |
| Example 12 | Polymer 12 (100) | — | Amine 1 (0.6) | — | PGMEA (1500) CyH (200) | 15.5 | 65 | 4.3 |
| Example 13 | Polymer 13 (100) | — | Amine 1 (0.6) | — | PGMEA (1500) CyH (200) | 18.6 | 65 | 4.9 |
| Example 14 | Polymer 14 (100) | — | Amine 2 (0.6) | — | PGMEA (1500) CyH (200) | 18.9 | 65 | 5.2 |
| Example 15 | Polymer 10 (100) | — | Amine 3 (0.6) | — | PGMEA (1500) CyH (200) | 16.3 | 65 | 4.3 |
| Example 16 | Polymer 10 (100) | — | Amine 1 (0.6) | DRI 1 (10) | PGMEA (1500) CyH (200) | 16.3 | 70 | 5.3 |
| Example 17 | Polymer 3 (100) | PAG 1 (18) | Amine 1 (0.6) | DRI 2 (10) | PGMEA (1500) CyH (200) | 14.3 | 70 | 6.8 |
| Example 18 | Polymer 3 (100) | PAG 2 (11) | Amine 1 (0.6) | — | PGMEA (1000) EL (200) | 13.3 | 70 | 6.8 |
| Example 19 | Polymer 15 (100) | — | Amine 1 (0.6) | — | PGMEA (1000) | 25.0 | 75 | 4.7 |

TABLE 1-continued

| | Polymer (parts by weight) | Acid generator (parts by weight) | Base (parts by weight) | Dissolution inhibitor (parts by weight) | Organic solvent (parts by weight) | Sensitivity ($\mu C/cm^2$) | Degree of Resolution (nm) | Edge roughness (nm) |
|---|---|---|---|---|---|---|---|---|
| Example 20 | Polymer 16 (100) | — | Amine 1 (0.6) | — | PGMEA (1000) | 23.0 | 75 | 4.6 |
| Comparative Example 1 | Comparative Polymer 1 (100) | PAG 1 (12) | Amine 1 (0.6) | — | PGMEA (1700) | 18.8 | 100 | 8.8 |
| Comparative Example 2 | Comparative Polymer 2 (100) | PAG 1 (12) | Amine 1 (0.6) | — | PGMEA (1500) CyH (200) | 35.5 | 90 | 9.2 |
| Comparative Example 3 | Comparative Polymer 3 (100) | PAG 1 (12) | Amine 1 (0.6) | — | PGMEA (1500) CyH (200) | 31.5 | 90 | 10.5 |

Each composition in Table 1 is as follows.
Polymers 1 to 16: Synthetic Examples 1 to 16
Comparative Polymers 1 to 3: Comparative Synthetic Examples 1 to 3
Organic solvent: PGMEA (propylene glycol monomethyl ether acetate)
EL (ethyl lactate)
CyH (cyclohexanone)
Acid generator: PAG 1 and PAG 2 (see the following structural formulae)
Basic compound: Amine 1, Amine 2, and Amine 3 (see the following structural formulae)
Dissolution inhibitor: DRI 1 and DRI 2 (see the following formulae)

-continued

DRI 2

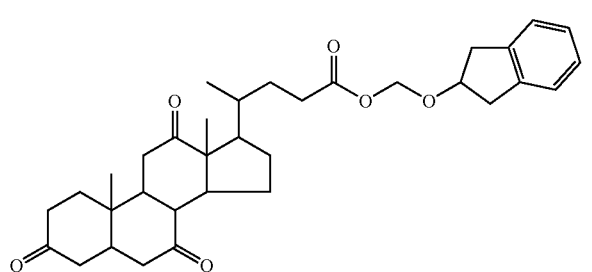

Evaluation of an Electronic Beam Drawing

In the drawing evaluation, each of the positive resist compositions prepared as shown above (Examples 1 to 20 and Comparative Examples 1 to 3) was spin-coated by using a Clean Track Mark 5 (manufactured by Tokyo Electron Ltd.) on a Si substrate with 6-inch (150 millimeters) in diameter. It was then pre-baked on a hot plate at 110° C. for 60 seconds to obtain a resist film with 100 nanometers in thickness. On it, a vacuum chamber drawing was performed by using a HL-800D (manufactured by Hitachi, Ltd.) at an HV voltage of 50 keV.

Immediately after the drawing, a post exposure bake (PEB) was carried out on a hot plate at 100° C. for 60 seconds by using a Clean Track Mark 5 (manufactured by Tokyo Electron Ltd.), and then puddle-developed in an aqueous TMAH solution (2.38% by weight concentration) for 30 seconds to obtain a positive pattern.

The resist pattern thus obtained was evaluated as follows.

By taking the minimum size at the exposure dose to resolve a 100-nanometers line-and-space at 1:1 as a resolving power, an edge roughness of a 100-nanometers LS was measured by a SEM.

The results of the sensitivity and the degree of resolution with regard to the resist composition and the EB exposure are shown in Table 1.

As shown in Table 1, it was confirmed that the positive resist compositions in Examples 1 to 20 had higher degree of resolution as compared with those in Comparative Examples 1 to 3. In addition, it can be seen that the sensitivity and the pattern configuration after exposure are excellent.

Evaluation of the Dry Etching Resistance

In the test of the dry etching resistance, 2 g each of the polymers synthesized by the above methods (Polymers 1 to 16, and Comparative Polymers 1 to 3) was dissolved into 10 g of PGMEA. The mixture thus obtained was filtered through a filter of a 0.2 micrometers size, and then the filtered polymer solution was applied on a Si substrate by a spin coat to obtain a film with 300 nanometers in thickness. The evaluation was made in the following conditions.

Etching Tests in a $CHF_3/CF_4$ Gas System

A difference of the polymer film thickness before and after the etching was measured by using a dry etching equipment TE-8500P (manufactured by Tokyo Electron Ltd.).

The etching conditions are as following:

| Chamber pressure: | 40.0 Pa |
| RF power: | 1,000 W |

-continued

| Gap: | 9 millimeters |
| CHF$_3$ gas flow rate: | 30 mL/minute |
| CF$_4$ gas flow rate: | 30 mL/minute |
| Ar gas flow rate: | 100 mL/minute |
| Time: | 60 seconds |

In this evaluation, when the difference in film thickness is small, namely the reduction amount is small, the film is judged to have the etching resistance.

The results of the dry etching resistance tests are shown in Table 2.

TABLE 2

| Polymer | Etching rate in CHF$_3$/CF$_4$ gas system (nm/min) |
| --- | --- |
| Polymer 1 | 115 |
| Polymer 2 | 119 |
| Polymer 3 | 102 |
| Polymer 4 | 120 |
| Polymer 5 | 98 |
| Polymer 6 | 95 |
| Polymer 7 | 100 |
| Polymer 8 | 93 |
| Polymer 9 | 90 |
| Polymer 10 | 108 |
| Polymer 11 | 105 |
| Polymer 12 | 110 |
| Polymer 13 | 114 |
| Polymer 14 | 99 |
| Polymer 15 | 108 |
| Polymer 16 | 107 |
| Comparative Polymer 1 | 110 |
| Comparative Polymer 2 | 138 |
| Comparative Polymer 3 | 145 |

From the results shown in Table 2, it was confirmed that the polymers according to the present invention (Polymers 1 to 16) have a higher dry etching resistance than Comparative Polymers 1 to 3.

From the results shown in the above, it was found that a positive resist composition containing the polymer of the present invention as the base resin fully satisfies a resolution, a sensitivity, and a roughness, and has an excellent dry etching resistance in view of a small difference in the film thickness after the etching.

It must be stated here that the present invention is not restricted to the embodiments shown by Examples. The embodiments shown by Examples are merely examples so that any embodiments composed of substantially the same technical concept as disclosed in the claims of the present invention and expressing a similar effect are included in the technical scope of the present invention.

What is claimed is:

1. A polymerizable compound represented by the following general formula (1):

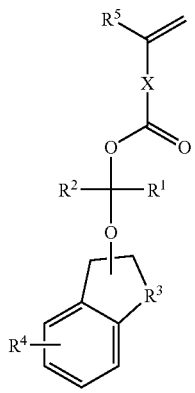

(1)

wherein, each of $R^1$ and $R^2$ independently represents any of a hydrogen atom or a linear, a branched, or a cyclic alkyl group having 1 to 6 carbon atoms; $R^3$ represents a methylene group or an ethylene group; $R^4$ represents any of a hydrogen atom, an alkyl group having 1 to 30 carbon atoms, an alkyl group a part of or all of whose hydrogen atoms are substituted by a halogen atom, an alkoxy group, an alkanoyl group, an alkoxycarbonyl group, an aryl group having 6 to 10 carbon atoms, a halogen atom, or a cyano group; $R^5$ represents a hydrogen atom or a methyl group; X represents any of a single bond, —C(=O)—O—$R^6$—, a phenylene group, or a naphthylene group; and $R^6$ represents any of a linear, a branched, or a cyclic alkylene group having 1 to 10 carbon atoms, and optionally containing an ester group, an ether group, or a lactone ring.

2. A polymer whose hydrogen atom of at least a carboxyl group is substituted by an acid labile group represented by the general formula (2):

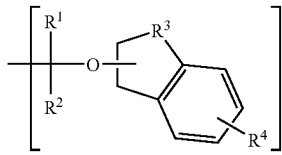

(2)

wherein, each of $R^1$ and $R^2$ independently represents any of a hydrogen atom, a linear, a branched, or a cyclic alkyl group having 1 to 6 carbon atoms; $R^3$ represents a methylene group or an ethylene group; and $R^4$ represents any of a hydrogen atom, an alkyl group having 1 to 30 carbon atoms, an alkyl group a part of or all of whose hydrogen atoms are substituted by a halogen atom, an alkoxy group, an alkanoyl group, an alkoxycarbonyl group, an aryl group having 6 to 10 carbon atoms, a halogen atom, or a cyano group.

3. The polymer according to claim 2, wherein the polymer contains at least a repeating unit "a" represented by the following general formula (3):

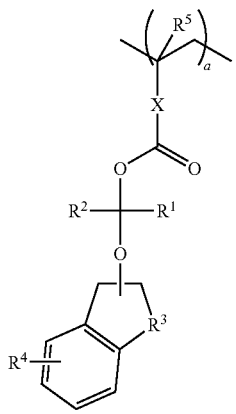

(3)

wherein, $R^1$ to $R^4$ represent the same meanings as before; $R^5$ represents a hydrogen atom or a methyl group; X represents any of a single bond, —C(=O)—O—$R^6$—, a phenylene group, or a naphthylene group; and $R^6$ represents any of a linear, a branched, or a cyclic alkylene group having 1 to 10 carbon atoms, and optionally containing an ester group, an ether group, or a lactone ring.

4. The polymer according to claim 3, wherein the polymer contains a repeating unit "a" represented by the general formula (3) accounting for 5 to 70 mole % of all the repeating units and its weight-average molecular weight is 1,000 to 500,000.

5. The polymer according to claim 3, wherein the repeating unit "a" represented by the general formula (3) is a repeating unit a1 or a repeating unit a2 shown in the general formula (4):

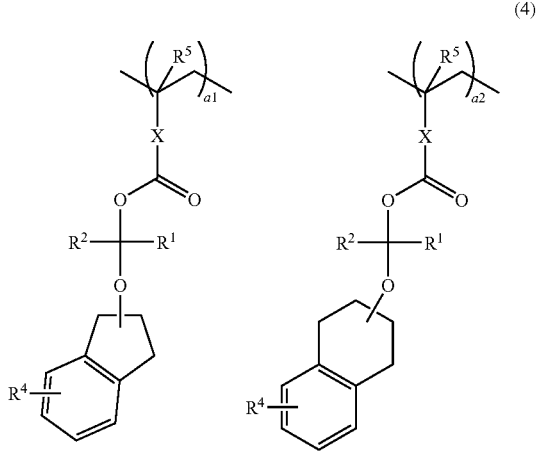

(4)

wherein, $R^1$, $R^2$, $R^4$, $R^5$, and X represent the same meanings as before, and $0.05 \leq a1+a2 \leq 0.75$.

6. The polymer according to claim 4, wherein the repeating unit "a" represented by the general formula (3) is a repeating unit a1 or a repeating unit a2 shown in the general formula (4):

(4)

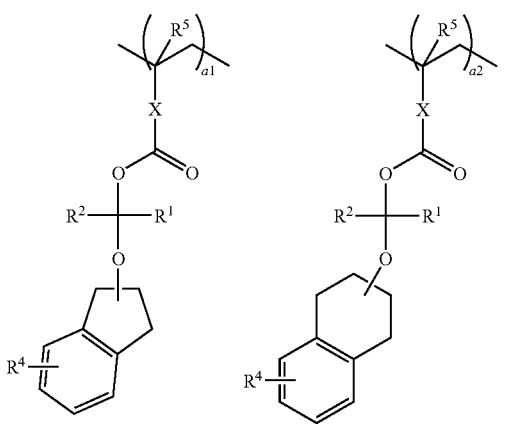

wherein, $R^1$, $R^2$, $R^4$, $R^5$, and X represent the same meanings as before, and $0.05 \leq a1+a2 \leq 0.75$.

7. The polymer according to claim 3, wherein the polymer is a copolymer of, in addition to the repeating unit "a" represented by the general formula (3), a repeating unit "b" which is an adhesion group having any of a hydroxy group, a lactone ring, an ether group, an ester group, a carbonyl group, or a cyano group, with the weight-average molecular weight of 1,000 to 500,000; and $0<a<1.0$, $0<b<1.0$, and $0.05 \leq a+b \leq 0.7$.

8. The polymer according to claim 4, wherein the polymer is a copolymer of, in addition to the repeating unit "a" represented by the general formula (3), a repeating unit "b" which is an adhesion group having any of a hydroxy group, a lactone ring, an ether group, an ester group, a carbonyl group, or a cyano group, with the weight-average molecular weight of 1,000 to 500,000; and $0<a<1.0$, $0<b<1.0$, and $0.05 \leq a+b<0.7$.

9. The polymer according to claim 5, wherein the polymer is a copolymer of, in addition to the repeating unit "a" represented by the general formula (3), a repeating unit "b" which is an adhesion group having any of a hydroxy group, a lactone ring, an ether group, an ester group, a carbonyl group, or a cyano group, with the weight-average molecular weight of 1,000 to 500,000; and $0<a<1.0$, $0<b<1.0$, and $0.05 \leq a+b \leq 0.7$.

10. The polymer according to claim 6, wherein the polymer is a copolymer of, in addition to the repeating unit "a" represented by the general formula (3), a repeating unit "b" which is an adhesion group having any of a hydroxy group, a lactone ring, an ether group, an ester group, a carbonyl group, or a cyano group, with the weight-average molecular weight of 1,000 to 500,000; and $0<a<1.0$, $0<b<1.0$, and $0.05 \leq a+b \leq 0.7$.

11. A positive resist composition containing at least, as a base resin, the polymer according to claim 3.

12. A positive resist composition containing at least, as a base resin, the polymer according to claim 10.

13. The positive resist composition according to claim 11, wherein the positive resist composition is a chemically amplified type containing further an organic solvent and an acid generator.

14. The positive resist composition according to claim 12, wherein the positive resist composition is a chemically amplified type containing further an organic solvent and an acid generator.

15. The positive resist composition according to claim 11, wherein the positive resist composition contains further a dissolution inhibitor.

16. The positive resist composition according to claim 14, wherein the positive resist composition contains further a dissolution inhibitor.

17. The positive resist composition according to claim 11, wherein the positive resist composition contains further a basic compound and/or a surfactant as an additive.

18. The positive resist composition according to claim 16, wherein the positive resist composition contains further a basic compound and/or a surfactant as an additive.

19. A patterning process, comprising: at least, a step of applying the positive resist composition according to claim 11 on a substrate; a step of conducting a heat-treatment; a step of exposing a high-energy beam; and a step of developing by using a developer.

20. A patterning process, comprising: at least, a step of applying the positive resist composition according to claim 18 on a substrate; a step of conducting a heat-treatment; a step of exposing a high-energy beam; and a step of developing by using a developer.

* * * * *